(12) United States Patent
Gao et al.

(10) Patent No.: US 9,670,211 B2
(45) Date of Patent: Jun. 6, 2017

(54) AZA-OXO-INDOLES FOR THE TREATMENT AND PROPHYLAXIS OF RESPIRATORY SYNCYTIAL VIRUS INFECTION

(71) Applicant: Hoffmann-La Roche Inc., Little Falls, NJ (US)

(72) Inventors: Lu Gao, Shanghai (CN); Lei Guo, Shanghai (CN); Chungen Liang, Shanghai (CN); Baoxia Wang, Shanghai (CN); Lisha Wang, Basel (CH); Hongying Yun, Shanghai (CN); Weixing Zhang, Shanghai (CN); Xiufang Zheng, Shanghai (CN)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 15/094,642

(22) Filed: Apr. 8, 2016

(65) Prior Publication Data
US 2016/0229853 A1 Aug. 11, 2016

Related U.S. Application Data

(63) Continuation of application No. PCT/EP2014/067046, filed on Aug. 8, 2014.

(30) Foreign Application Priority Data

Aug. 12, 2013 (CN) ................ PCT/CN2013/081263

(51) Int. Cl.
*C07D 471/10* (2006.01)
*C07D 471/04* (2006.01)
*C07D 519/00* (2006.01)

(52) U.S. Cl.
CPC ......... *C07D 471/10* (2013.01); *C07D 471/04* (2013.01); *C07D 519/00* (2013.01)

(58) Field of Classification Search
None
See application file for complete search history.

(56) References Cited

FOREIGN PATENT DOCUMENTS

| WO | 2012/080450 A1 | 6/2012 |
| WO | 2013/068769 A1 | 5/2013 |
| WO | 2014060411 | * 4/2014 |
| WO | 2014/184163 A1 | 11/2014 |

OTHER PUBLICATIONS

Ansel et al., "Pharmaceutical Dosage Forms and Drug Delivery Systems" 6th Ed.:456-457 (1995).
Bastin et al., "Salt Selection and Optimisation Procedures for Pharmaceutical New Chemical Entities" Organic Process Research & Development 4:457-435 (2000).
Combrink et al., "Respiratory syncytial virus fusion inhibitors. Part 6: An examination of the effect of structural variation of the benzimidazol-2-one heterocycle moiety" Bioorganic & Medicinal Chemistry Letters 17(17):4787-4790 (Aug. 4, 2007).
DeVincenzo et al., "A randomized, double-blind, placebo-controlled study of an RNAi-based therapy directed against respiratory syncytial virus" PNAS 107(19):8800-8805 (May 11, 2010).
Feltes et al., "A Randomized Controlled Trial of Motavizumab Verus Palivizumab for the Prophylaxis of Serious Respiratory Syncytial Virus Disease in Children with Hemodynamically Significant Congenital Heart Disease" Pediatric Research 70(2):186-191 (2011).
Feltes et al., "Palivizumab prophylaxis reduces hospitalization due to respiratory syncytial virus in young children with hemodynamically significant congenital heart disease" The Journal of Pediatrics 143(4):532-540 (Oct. 2003).
International Preliminary Report on Patentability issued in PCT/EP2014/067046, issued Feb. 16, 2016, in 7 pages.
International Search Report issued in International Application No. PCT/EP2014/067046, dated Oct. 8, 2014, in 4 pages.
The IMpact-RSV Study (No authors listed), "Palivizumab, a Humanized Respiratory Syncytial Virus Monoclonal Antibody, Reduces Hospitalization From Respiratory Syncytial Virus Infection in High-risk Infants" Pediatrics 102(3):531-537 (Sep. 1998).
Written Opinion of International Searching Authority issued in International Application No. PCT/EP2014/067046, dated Oct. 8, 2014, in 6 pages.
Zamora et al., "RNA Interference Therapy in Lung Transplant Patients Infected with Respiratory Syncytial Virus" Am J Resp Crit Care 183:531-538 (2011).
Office Action issued in Japanese Patent Application No. 2016-533895, mailed Jan. 6, 2017, with English translation (total in 4 pages).

* cited by examiner

*Primary Examiner* — Karl J Puttlitz
(74) *Attorney, Agent, or Firm* — Tony Peng

(57) ABSTRACT

The invention provides novel compounds having the general formula:

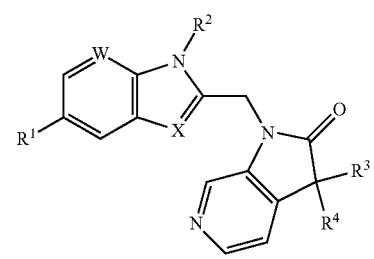

wherein $R^1$, $R^2$, $R^3$, $R^4$, W and X are as described herein, compositions including the compounds and methods of using the compounds.

10 Claims, No Drawings

AZA-OXO-INDOLES FOR THE TREATMENT AND PROPHYLAXIS OF RESPIRATORY SYNCYTIAL VIRUS INFECTION

CROSS REFERENCE TO RELATED APPLICATIONS

This application is a continuation of International Application No. PCT/EP2014/067046 having an international filing date of Aug. 8, 2014, the entire contents of which are incorporated herein by reference, and which claims benefit under 35 U.S.C. § 119 to PCT/CN2013/081263 having an international filing date of Aug. 12, 2013.

The present invention relates to organic compounds useful for therapy and/or prophylaxis in a mammal, and in particular to respiratory syncytial virus (RSV) inhibitors useful for treating RSV infection.

FIELD OF THE INVENTION

Respiratory Syncytial Virus (RSV) belongs to the family of Paramyxoviridae, subfamily of Pneumovirinae. The human RSV is a major cause of acute upper and lower respiratory tract infection in infants and children. Almost all children are infected by RSV at least once by age of three. Natural human immunity against RSV is incomplete. In normal adults and elder children, RSV infection is mainly associated with upper respiratory track symptoms. Severe case of RSV infection often leads to bronchiolitis and pneumonia, which requires hospitalization. High-risk factors for lower respiratory tract infections include premature birth, congenital heart disease, chronic pulmonary disease, and immunocompromised conditions. A severe infection at young age may lead to recurrent wheezing and asthma. For the elderly, RSV-related mortality rate becomes higher with advancing age.

RSV Fusion (F) protein is a surface glycoprotein on the viral envelope which, together with the G surface glycoprotein, mediates viral entry into host cell. The F protein initiates viral penetration by fusing viral and host cellular membranes and subsequently promotes viral spread after infection by melding infected cells to adjacent uninfected cells, resulting in characteristic syncytial formation. By inhibiting viral entry and spread, it is expected that treatment with chemicals described here will decrease the duration and severity of respiratory symptoms and subsequent risk of prolonged hospitalization and complications. It is also expected to limit the ability of individuals to transmit RSV within households, nursing homes and the hospital setting to other hosts potentially at high risk of complications.

There is no RSV vaccine available for human use, despite of many attempts in subunit vaccine and live-attenuated vaccine approaches. Virazole®, the aerosol form of ribavirin, is the only approved antiviral drug for treatment of RSV infection. However, it is rarely used clinically, due to limited efficacy and potential side effects. Two marketed prophylaxis antibodies were developed by MedImmune (CA, USA).

RSV-IGIV (brand name RespiGam) is polyclonal-concentrated RSV neutralizing antibody administered through monthly infusion of 750 mg/kg in hospital (Wandstrat T L, Ann Pharmacother. 1997 January; 31(1):83-8). Subsequently, the usage of RSV-IGIV was largely replaced by palivizumab (brand name Synagis®), a humanized monoclonal antibody against RSV fusion (F) protein approved for prophylaxis in high-risk infants in 1998. When administered intramuscularly at 15 mg/kg once a month for the duration of RSV season, palivizumab demonstrated 45-55% reduction of hospitalization rate caused by RSV infection in selected infants (Pediatrics. 1998 September; 102(3):531-7; Feltes T F et al, J Pediatr. 2003 October; 143(4):532-40). Unfortunately, palivizumab is not effective in the treatment of established RSV infection. A newer version monoclonal antibody, motavizumab, was designed as potential replacement of palivizumab but failed to show additional benefit over palivizumab in recent Phase III clinical trials (Feltes T F et al, Pediatr Res. 2011 August; 70(2):186-91).

A number of small molecule RSV inhibitors have been discovered. Among them, only a few reached Phase I or II clinical trials. Arrow Therapeutics (now a group in AstraZeneca, UK) completed a five-year Phase II trial of nucleocapsid (N) protein inhibitor, RSV-604, in stem cell transplantation patients by February 2010 (www.clinicaltrials.gov), but has not released the final results. Most of other small molecules were put on hold for various reasons.

RNAi therapeutics against RSV has also been thoroughly studied. ALN-RSV01 (Alnylam Pharmaceuticals, MA, USA) is a siRNA targeting on RSV gene. A nasal spray administered for two days before and for three days after RSV inoculation decreased infection rate among adult volunteers (DeVincenzo J. et al, Proc Natl Acad Sci USA. 2010 May 11; 107(19):8800-5). In another Phase II trial using naturally infected lung transplantation patients, results were not sufficient for conclusion of antiviral efficacy, though certain health benefits have been observed (Zamora M R et al, Am J Respir Crit Care Med. 2011 Feb. 15; 183(4):531-8). Additional Phase IIb clinical trials in similar patient population for ALN-RSV01 are on-going (www.clinicaltrials.gov).

Nevertheless, safe and effective treatment for RSV disease is needed urgently.

SUMMARY OF THE INVENTION

Objects of the present invention are novel compounds of formula I, their manufacture, medicaments based on a compound in accordance with the invention and their production as well as the use of compounds of formula I for the treatment or prophylaxis of RSV infection.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_xH_{2x}$," alone or in combination signifies a saturated, linear- or branched chain alkyl group containing 1 to 6, particularly 1 to 4 carbon atoms.

The term "cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "cycloalkyl" groups are cyclopropyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "halogen" means fluorine, chlorine, bromine or iodine. Halogen is particularly fluorine, chlorine or bromine.

The term "hydroxy" alone or in combination refers to the group —OH.

The term "carboxy" alone or in combination refers to the group —COOH.

The term "carbonyl" alone or in combination refers to the group —C(O)—.

The term "sulfonyl" alone or in combination refers to the group —S(O)$_2$—.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of RSV Fusion Protein

The present invention provides (i) novel compounds having the general formula I:

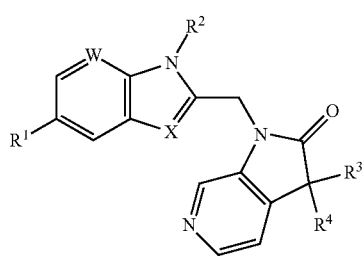

(I)

wherein $R^1$ is halogen;

$R^2$ is azetidinyl, which is unsubstituted or substituted by $C_{1-6}$alkylsulfonyl; $C_{1-6}$alkoxycarbonylpyrrolidinyl; $C_{1-6}$alkylcarbonylpyrrolidinyl; cycloalkyl, which is unsubstituted or substituted by $C_{1-6}$alkyl, $C_{1-6}$alkylsulfonyl, carboxy, halogen or hydroxy; dioxo-tetrahydrothiophenyl, which is unsubstituted or substituted by $C_{1-6}$alkyl; dioxo-tetrahydrothiopyranyl; dioxo-thietanyl; oxo-thietanyl; oxo-pyrrolidinyl, which is unsubstituted or substituted by $C_{1-6}$alkyl; oxetanyl; oxopiperidinyl; piperidinyl; tetrahydrofuranyl; tetrahydropyranyl;

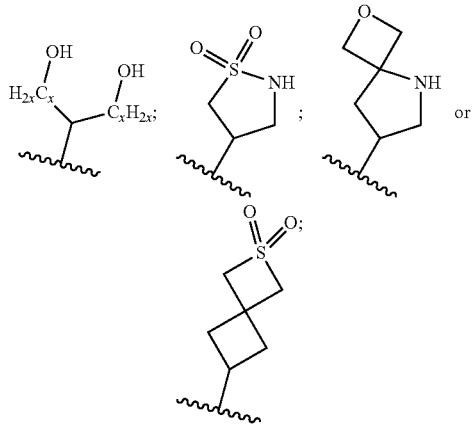

wherein x is 1-6;

$R^3$ is $C_{1-6}$alkyl;

$R^4$ is $C_{1-6}$alkyl;

or $R^3$ and $R^4$, with the carbon atom to which they are attached, form cycloalkyl;

W is nitrogen or —CR$^5$, wherein R$^5$ is hydrogen or halogen;

X is —CH or nitrogen;

or pharmaceutically acceptable salts thereof.

Further embodiment of present invention is (ii) a compound of formula I, wherein $R^1$ is chloro;

$R^2$ is azetidin-3-yl, methylsulfonylazetidin-3-yl, tert-butoxycarbonylpyrrolidinyl, isopropylcarbonylpyrrolidinyl, cyclopentyl, difluorocyclobutyl, difluorocyclopentyl, carboxycyclohexyl, hydroxycyclobutyl, hydroxycyclohexyl, hydroxycyclopentyl, methylsulfonylcyclobutyl, oxetan-3-yl, piperidin-4-yl, tetrahydrofuranyl, tetrahydropyranyl,

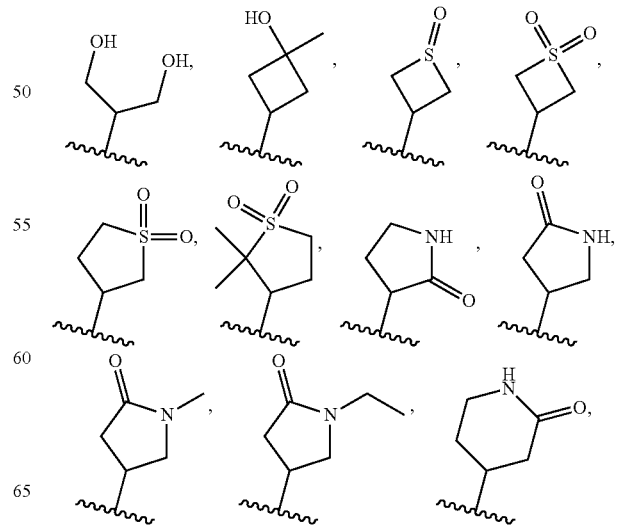

-continued

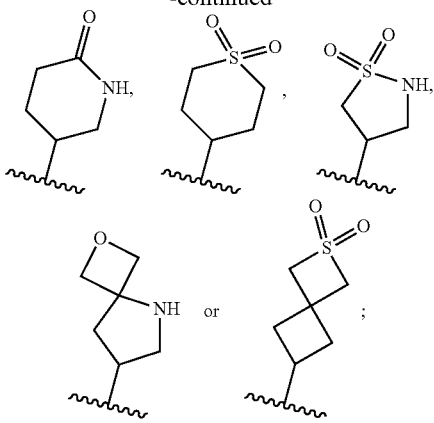

R³ is methyl or ethyl;
R⁴ is methyl or ethyl;
or R³ and R⁴, with the carbon atom to which they are attached, form cyclopropyl;
W is nitrogen, —CH or —CF;
X is —CH or nitrogen;
or pharmaceutically acceptable salts thereof.

Another embodiment of present invention is (iii) a compound of formula I or a pharmaceutically acceptable salt thereof, wherein
R¹ is halogen;
R² is azetidinyl, which is unsubstituted or substituted by $C_{1-6}$alkylsulfonyl; $C_{1-6}$alkoxycarbonylpyrrolidinyl; $C_{1-6}$alkylcarbonylpyrrolidinyl; cycloalkyl, which is unsubstituted or substituted by $C_{1-6}$alkyl, $C_{1-6}$alkylsulfonyl, carboxy, halogen or hydroxy; dioxo-tetrahydrothiophenyl, which is unsubstituted or substituted by $C_{1-6}$alkyl; dioxo-tetrahydrothiopyranyl; dioxo-thietanyl; oxo-thietanyl; oxo-pyrrolidinyl, which is unsubstituted or substituted by $C_{1-6}$alkyl; oxetanyl; oxopiperidinyl; piperidinyl; tetrahydrofuranyl; tetrahydropyranyl;

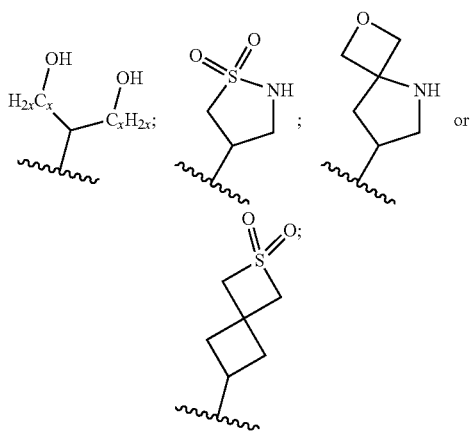

wherein x is 1-6;
R³ is $C_{1-6}$alkyl;
R⁴ is $C_{1-6}$alkyl;
or R³ and R⁴, with the carbon atom to which they are attached, form cycloalkyl;
W is —CR⁵, wherein R⁵ is hydrogen or halogen;
X is nitrogen.

Further embodiment of present invention is (iv) a compound of formula I or a pharmaceutically acceptable salt thereof, wherein
R¹ is chloro;
R² is azetidin-3-yl, methylsulfonylazetidin-3-yl, tert-butoxycarbonylpyrrolidinyl, isopropylcarbonylpyrrolidinyl, cyclopentyl, difluorocyclobutyl, difluorocyclopentyl, carboxycyclohexyl, hydroxycyclobutyl, hydroxycyclohexyl, hydroxycyclopentyl, methylsulfonylcyclobutyl, oxetan-3-yl, piperidin-4-yl, tetrahydrofuranyl, tetrahydropyranyl,

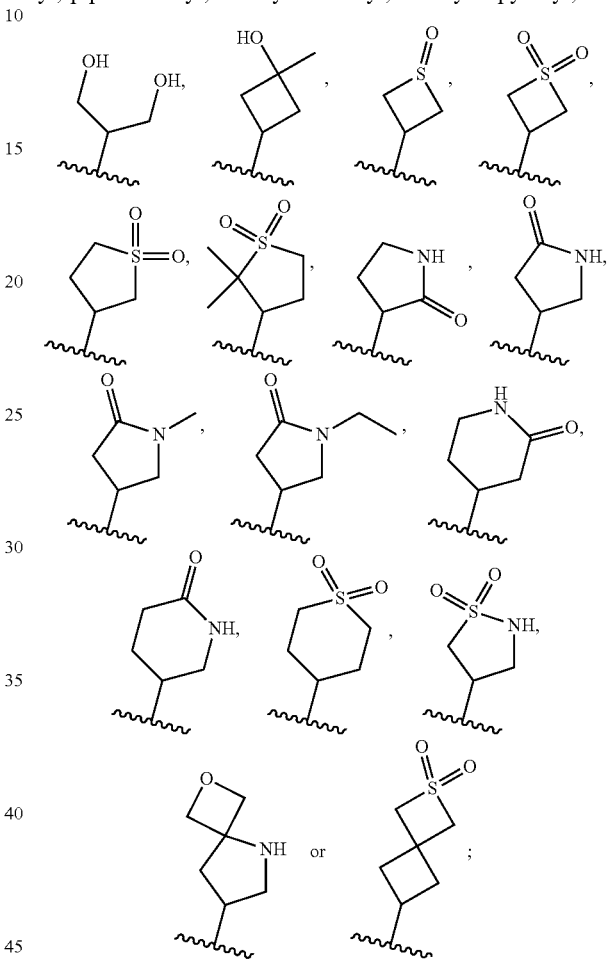

R³ is methyl or ethyl;
R⁴ is methyl or ethyl;
or R³ and R⁴, with the carbon atom to which they are attached, form cyclopropyl;
W is —CH or —CF;
X is nitrogen.

Another embodiment of present invention is (v) a compound of formula I or a pharmaceutically acceptable salt thereof, wherein
R¹ is halogen;
R² is dioxo-tetrahydrothiophenyl;
R³ and R⁴, with the carbon atom to which they are attached, form cycloalkyl;
W is nitrogen;
X is nitrogen.

Another embodiment of present invention is (vi) a compound of formula I or a pharmaceutically acceptable salt thereof, wherein
R¹ is halogen;
R² is dioxo-tetrahydrothiophenyl;
R³ and R⁴, with the carbon atom to which they are attached, form cycloalkyl;

W is nitrogen or —CR$^5$, wherein R$^5$ is hydrogen or halogen;

X is —CH.

Particular compounds of formula I, including their activity data, NMR data and MS data are summarized in the following Table 1 and 2.

TABLE 1

Structure, name and activity data of particular compounds

| Example No. | Structure | Name | CPE Long EC$_{50}$ (μM) |
|---|---|---|---|
| 1-1 | 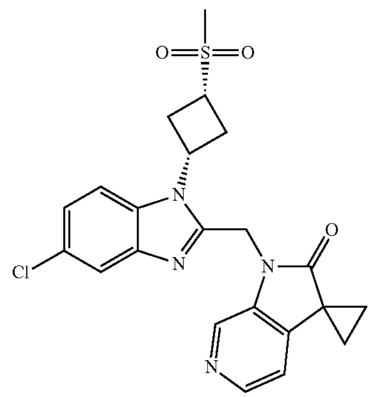 [SMILES: CS(=O)(=O)[C@H]1C[C@@H](n2c(CN3C(=O)C4(CC4)c4ccncc43)nc3cc(Cl)ccc32)C1] | 1'-({5-Chloro-1-[cis-3-(methylsulfonyl)cyclobutyl]-1H-benzimidazol-2-yl}methyl)spiro[cyclopropane-1,3'-pyrrolo[2,3-c]pyridin]-2'(1'H)-one | 0.01 |
| 1-2 | 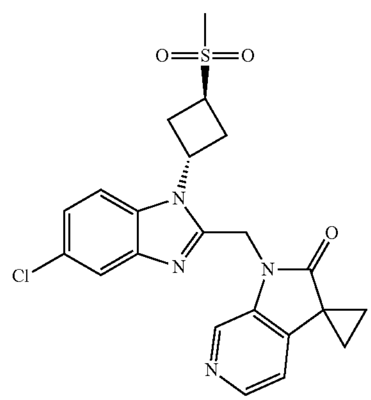 [SMILES: CS(=O)(=O)[C@H]1C[C@H](n2c(CN3C(=O)C4(CC4)c4ccncc43)nc3cc(Cl)ccc32)C1] | 1'-({5-Chloro-1-[trans-3-(methylsulfonyl)cyclobutyl]-1H-benzimidazol-2-yl}methyl)spiro[cyclopropane-1,3'-pyrrolo[2,3-c]pyridin]-2'(1'H)-one | 0.006 |
| 2-1 | 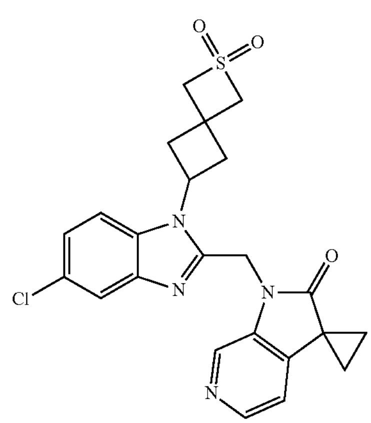 [SMILES: O=C1N(Cc2nc3cc(Cl)ccc3n2C2CC3(C2)CS(=O)(=O)C3)c2cnccc2C12CC2] | 1'-{[5-Chloro-1-(2,2-dioxido-2-thiaspiro[3.3]hept-6-yl)-1H-benzimidazol-2-yl]methyl}spiro[cyclopropane-1,3'-pyrrolo[2,3-c]pyridin]-2'(1'H)-one | 0.004 |

TABLE 1-continued

Structure, name and activity data of particular compounds

| Example No. | Structure | Name | CPE Long EC$_{50}$ (μM) |
|---|---|---|---|
| 2-2 | 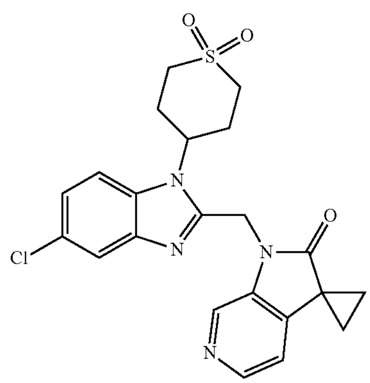 [SMILES: O=C1N(Cc2nc3cc(Cl)ccc3n2C2CCS(=O)(=O)CC2)c2cnccc2C12CC2] | 1'-{[5-Chloro-1-(1,1-dioxidotetrahydro-2H-thiopyran-4-yl)-1H-benzimidazol-2-yl]methyl}spiro[cyclopropane-1,3'-pyrrolo[2,3-c]pyridin]-2'(1'H)-one | 0.006 |
| 2-3 | 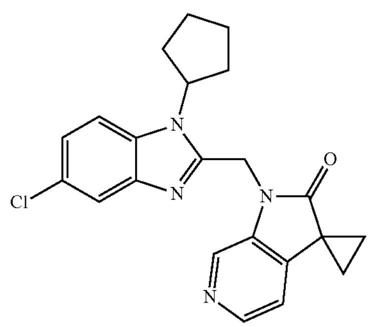 [SMILES: O=C1N(Cc2nc3cc(Cl)ccc3n2C2CCCC2)c2cnccc2C12CC2] | 1'-[(5-Chloro-1-cyclopentyl-1H-benzimidazol-2-yl)methyl]spiro[cyclopropane-1,3'-pyrrolo[2,3-c]pyridin]-2'(1'H)-one | 0.032 |
| 2-4 | 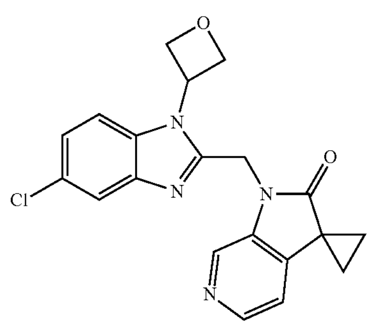 [SMILES: O=C1N(Cc2nc3cc(Cl)ccc3n2C2COC2)c2cnccc2C12CC2] | 1'-{[5-Chloro-1-(oxetan-3-yl)-1H-benzimidazol-2-yl]methyl}spiro[cyclopropane-1,3'-pyrrolo[2,3-c]pyridin]-2'(1'H)-one | 0.07 |
| 2-5 | 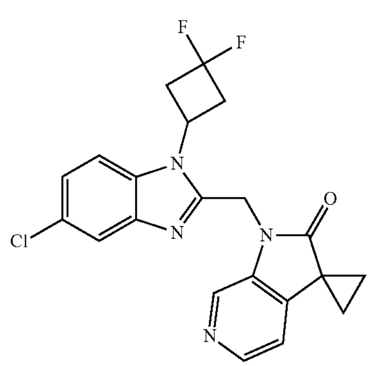 [SMILES: O=C1N(Cc2nc3cc(Cl)ccc3n2C2CC(F)(F)C2)c2cnccc2C12CC2] | 1'-{[5-Chloro-1-(3,3-difluorocyclobutyl)-1H-benzimidazol-2-yl]methyl}spiro[cyclopropane-1,3'-pyrrolo[2,3-c]pyridin]-2'(1'H)-one | 0.016 |

TABLE 1-continued

Structure, name and activity data of particular compounds

| Example No. | Structure | Name | CPE Long EC$_{50}$ (μM) |
|---|---|---|---|
| 2-6 | 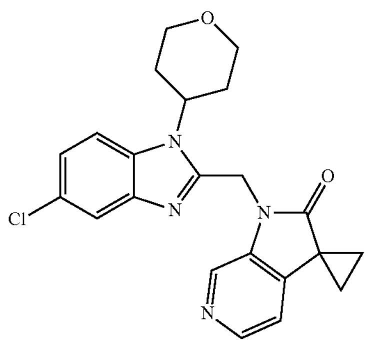 [SMILES: O=C1N(Cc2nc3cc(Cl)ccc3n2C2CCOCC2)c2cnccc2C12CC2] | 1'-{[5-Chloro-1-(tetrahydro-2H-pyran-4-yl)-1H-benzimidazol-2-yl]methyl}spiro[cyclopropane-1,3'-pyrrolo[2,3-c]pyridin]-2'(1'H)-one | 0.023 |
| 2-7 | 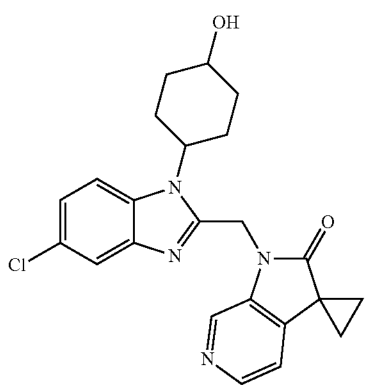 [SMILES: O=C1N(Cc2nc3cc(Cl)ccc3n2C2CCC(O)CC2)c2cnccc2C12CC2] | 1'-{[5-Chloro-1-(4-hydroxycyclohexyl)-1H-benzimidazol-2-yl]methyl}spiro[cyclopropane-1,3'-pyrrolo[2,3-c]pyridin]-2'(1'H)-one | 0.0011 |
| 2-8 | 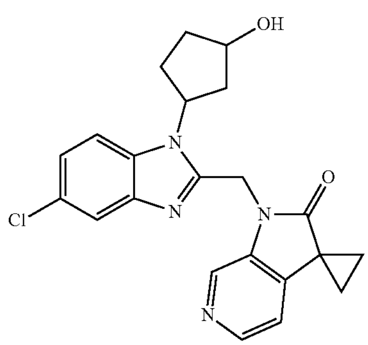 [SMILES: O=C1N(Cc2nc3cc(Cl)ccc3n2C2CCC(O)C2)c2cnccc2C12CC2] | 1'-{[5-Chloro-1-(3-hydroxy-cyclopentyl)-1H-benzimidazol-2-yl]methyl}spiro[cyclopropane-1,3'-pyrrolo[2,3-c]pyridin]-2'(1'H)-one | 0.011 |
| 2-9 | 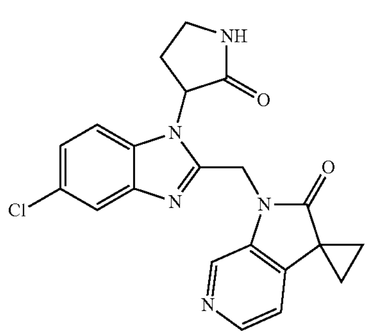 [SMILES: O=C1NCCC1n1c(CN2C(=O)C3(CC3)c3ccncc32)nc2cc(Cl)ccc21] | 1'-{[5-Chloro-1-(2-oxopyrrolidin-3-yl)-1H-benzimidazol-2-yl]methyl}spiro[cyclopropane-1,3'-pyrrolo[2,3-c]pyridin]-2'(1'H)-one | 0.164 |

TABLE 1-continued

Structure, name and activity data of particular compounds

| Example No. | Structure | Name | CPE Long EC$_{50}$ (μM) |
|---|---|---|---|
| 2-10 | 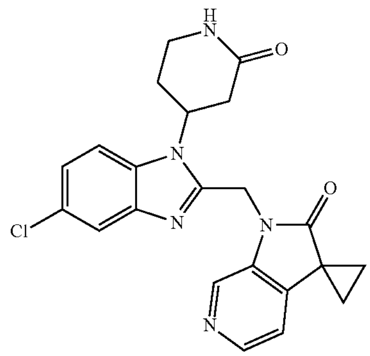 [SMILES: O=C1CC(n2c(CN3C(=O)C4(CC4)c4ccncc43)nc3cc(Cl)ccc32)CCN1] | 1'-{[5-Chloro-1-(2-oxopiperidin-4-yl)-1H-benzimidazol-2-yl]methyl}spiro[cyclopropane-1,3'-pyrrolo[2,3-c]pyridin]-2'(1'H)-one | 0.005 |
| 2-11 | 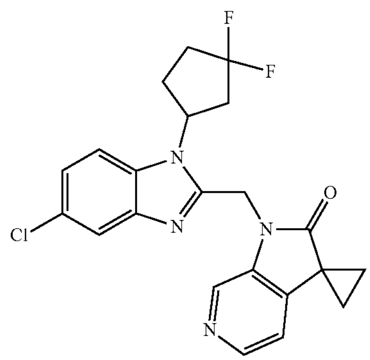 [SMILES: O=C1N(Cc2nc3cc(Cl)ccc3n2C2CCC(F)(F)C2)c2cnccc2C12CC2] | 1'-{[5-Chloro-1-(3,3-difluorocyclopentyl)-1H-benzimidazol-2-yl]methyl}spiro[cyclopropane-1,3'-pyrrolo[2,3-c]pyridin]-2'(1'H)-one | 0.017 |
| 2-12 | 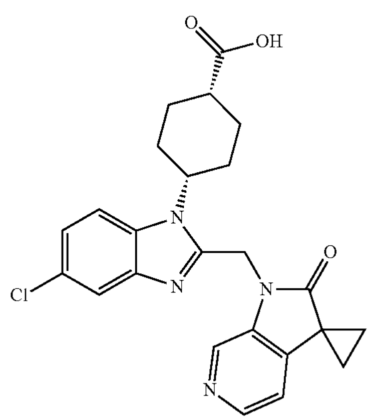 [SMILES: O=C1N(Cc2nc3cc(Cl)ccc3n2[C@H]2CC[C@@H](C(=O)O)CC2)c2cnccc2C12CC2] | cis-4-{5-Chloro-2-[(2'-oxospiro[cyclopropane-1,3'-pyrrolo[2,3-c]pyridin]-1'(2'H)-yl)methyl]-1H-benzimidazol-1-yl}cyclohexanecarboxylic acid | 0.51 |
| 2-13 | 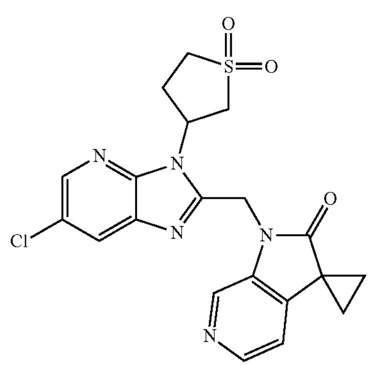 [SMILES: O=C1N(Cc2nc3cc(Cl)cnc3n2C2CCS(=O)(=O)C2)c2cnccc2C12CC2] | 1'-{[6-Chloro-3-(1,1-dioxidotetrahydrothiophen-3-yl)-3H-imidazo[4,5-b]pyridin-2-yl]methyl}spiro[cyclopropane-1,3'-pyrrolo[2,3-c]pyridin]-2'(1'H)-one | 0.015 |

TABLE 1-continued

Structure, name and activity data of particular compounds

| Example No. | Structure | Name | CPE Long EC$_{50}$ (μM) |
|---|---|---|---|
| 2-14 | 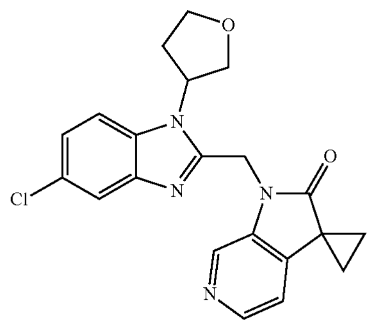 [SMILES: O=C1N(Cc2nc3cc(Cl)ccc3n2C2CCOC2)c2cnccc2C12CC2] | 1'-{[5-Chloro-1-(tetrahydrofuran-3-yl)-1H-benzimidazol-2-yl]methyl}spiro[cyclopropane-1,3'-pyrrolo[2,3-c]pyridin]-2'(1'H)-one | 0.006 |
| 2-15 | 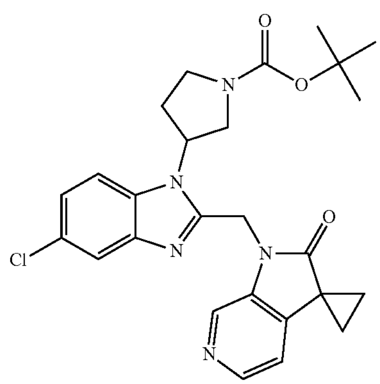 [SMILES: CC(C)(C)OC(=O)N1CCC(n2c(CN3C(=O)C4(CC4)c4ccncc43)nc3cc(Cl)ccc32)C1] | tert-Butyl 3-{5-chloro-2-[(2'-oxospiro[cyclopropane-1,3'-pyrrolo[2,3-c]pyridin]-1'(2'H)-yl)methyl]-1H-benzimidazol-1-yl}pyrrolidine-1-carboxylate | 0.031 |
| 2-16 | 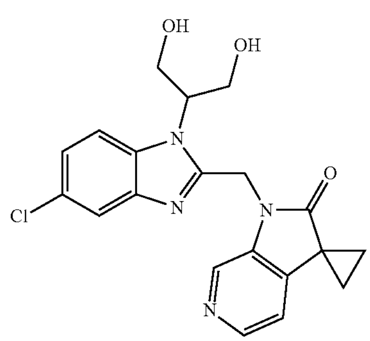 [SMILES: O=C1N(Cc2nc3cc(Cl)ccc3n2C(CO)CO)c2cnccc2C12CC2] | 1'-{[5-Chloro-1-(1,3-dihydroxypropan-2-yl)-1H-benzimidazol-2-yl]methyl}spiro[cyclopropane-1,3'-pyrrolo[2,3-c]pyridin]-2'(1'H)-one | 0.122 |
| 2-17 | 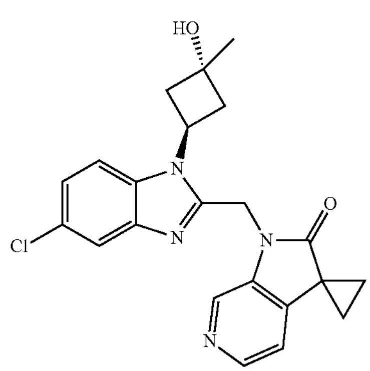 [SMILES: C[C@]1(O)C[C@H](n2c(CN3C(=O)C4(CC4)c4ccncc43)nc3cc(Cl)ccc32)C1] | 1'-{[5-Chloro-1-(trans-3-hydroxy-3-methylcyclobutyl)-1H-benzimidazol-2-yl]methyl}spiro[cyclopropane-1,3'-pyrrolo[2,3-c]pyridin]-2'(1'H)-one | 0.005 |

TABLE 1-continued

Structure, name and activity data of particular compounds

| Example No. | Structure | Name | CPE Long EC$_{50}$ (μM) |
|---|---|---|---|
| 3-1 | 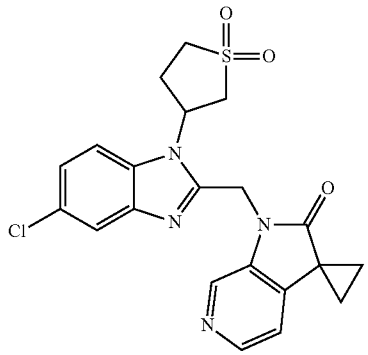 [SMILES: O=C1N(Cc2nc3cc(Cl)ccc3n2C2CCS(=O)(=O)C2)c2cnccc2C12CC2] | 1'-{[5-Chloro-1-(1,1-dioxidotetrahydrothiophen-3-yl)-1H-benzimidazol-2-yl]methyl}spiro[cyclopropane-1,3'-pyrrolo[2,3-c]pyridin]-2'(1'H)-one | 0.006 |
| 3-2 | Chiral | 1'-({5-Chloro-1-[(3S)-1,1-dioxidotetrahydrothiophen-3-yl]-1H-benzimidazol-2-yl}methyl)spiro[cyclopropane-1,3'-pyrrolo[2,3-c]pyridin]-2'(1'H)-one | 0.01 |
| 3-3 | Chiral | 1'-({5-Chloro-1-[(3R)-1,1-dioxidotetrahydrothiophen-3-yl]-1H-benzimidazol-2-yl}methyl)spiro[cyclopropane-1,3'-pyrrolo[2,3-c]pyridin]-2'(1'H)-one | 0.0016 |
| 4-1 | 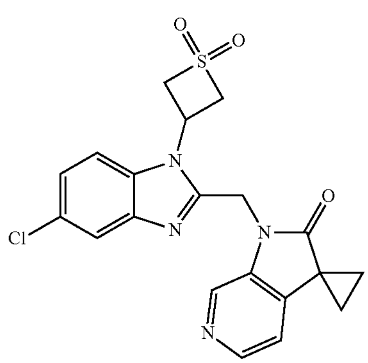 [SMILES: O=C1N(Cc2nc3cc(Cl)ccc3n2C2CS(=O)(=O)C2)c2cnccc2C12CC2] | 1'-{[5-Chloro-1-(1,1-dioxidothietan-3-yl)-1H-benzimidazol-2-yl]methyl}spiro[cyclopropane-1,3'-pyrrolo[2,3-c]pyridin]-2'(1'H)-one | 0.0065 |

TABLE 1-continued

Structure, name and activity data of particular compounds

| Example No. | Structure | Name | CPE Long EC$_{50}$ (μM) |
|---|---|---|---|
| 4-2 | 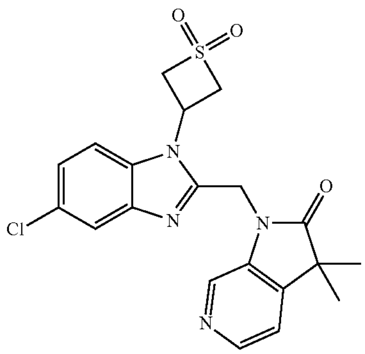 [SMILES: CC1(C)C(=O)N(Cc2nc3cc(Cl)ccc3n2C2CS(=O)(=O)C2)c2cnccc21] | 1-{[5-Chloro-1-(1,1-dioxidothietan-3-yl)-1H-benzimidazol-2-yl]methyl}-3,3-dimethyl-1,3-dihydro-2H-pyrrolo[2,3-c]pyridin-2-one | 0.095 |
| 4-3 | 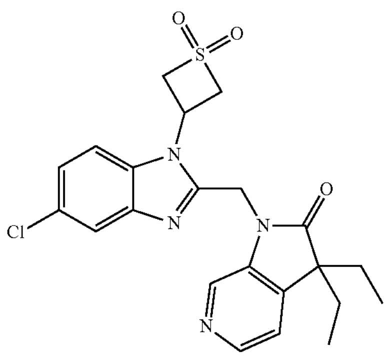 [SMILES: CCC1(CC)C(=O)N(Cc2nc3cc(Cl)ccc3n2C2CS(=O)(=O)C2)c2cnccc21] | 1-{[5-Chloro-1-(1,1-dioxidothietan-3-yl)-1H-benzimidazol-2-yl]methyl}-3,3-diethyl-1,3-dihydro-2H-pyrrolo[2,3-c]pyridin-2-one | 0.207 |
| 5 | 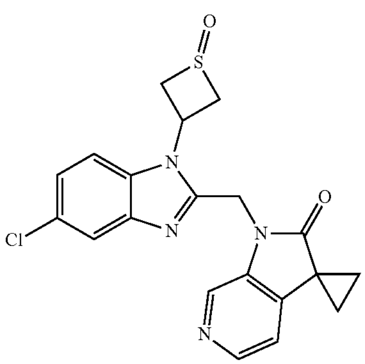 [SMILES: O=C1N(Cc2nc3cc(Cl)ccc3n2C2CS(=O)C2)c2cnccc2C12CC2] | 1'-{[5-Chloro-1-(1-oxidothietan-3-yl)-1H-benzimidazol-2-yl]methyl}spiro[cyclopropane-1,3'-pyrrolo[2,3-c]pyridin]-2'(1'H)-one | 0.005 |
| 6 | 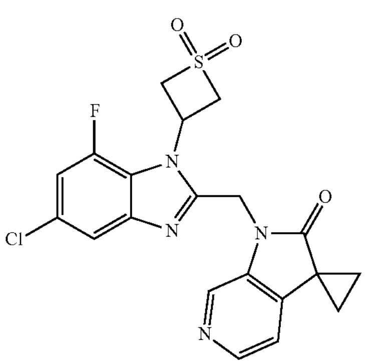 [SMILES: O=C1N(Cc2nc3cc(Cl)cc(F)c3n2C2CS(=O)(=O)C2)c2cnccc2C12CC2] | 1'-{[5-Chloro-1-(1,1-dioxidothietan-3-yl)-7-fluoro-1H-benzimidazol-2-yl]methyl}spiro[cyclopropane-1,3'-pyrrolo[2,3-c]pyridin]-2'(1'H)-one | 0.0009 |

TABLE 1-continued

Structure, name and activity data of particular compounds

| Example No. | Structure | Name | CPE Long $EC_{50}$ (μM) |
|---|---|---|---|
| 7-1 | 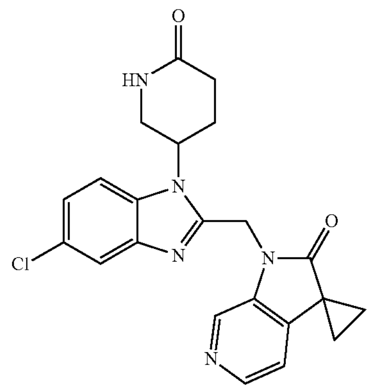 [SMILES: O=C1CCC(n2c(CN3C(=O)C4(CC4)c4ccncc43)nc3cc(Cl)ccc32)CN1] | 1'-{[5-Chloro-1-(6-oxopiperidin-3-yl)-1H-benzimidazol-2-yl]methyl}spiro[cyclopropane-1,3'-pyrrolo[2,3-c]pyridin]-2'(1'H)-one | 0.002 |
| 7-2 | 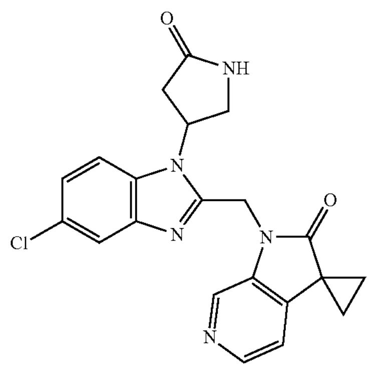 [SMILES: O=C1CC(n2c(CN3C(=O)C4(CC4)c4ccncc43)nc3cc(Cl)ccc32)CN1] | 1'-{[5-Chloro-1-(5-oxopyrrolidin-3-yl)-1H-benzimidazol-2-yl]methyl}spiro[cyclopropane-1,3'-pyrrolo[2,3-c]pyridin]-2'(1'H)-one | 0.009 |
| 8-1 | 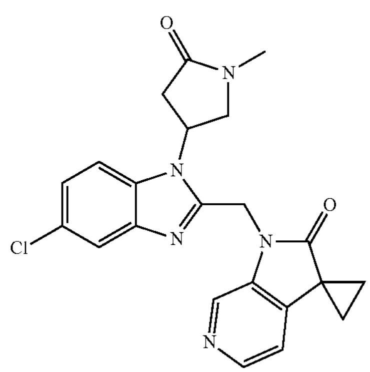 [SMILES: CN1CC(n2c(CN3C(=O)C4(CC4)c4ccncc43)nc3cc(Cl)ccc32)CC1=O] | 1'-{[5-Chloro-1-(1-methyl-5-oxopyrrolidin-3-yl)-1H-benzimidazol-2-yl]methyl}spiro[cyclopropane-1,3'-pyrrolo[2,3-c]pyridin]-2'(1'H)-one | 0.006 |
| 8-2 | 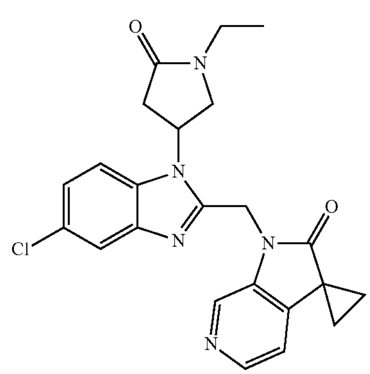 [SMILES: CCN1CC(n2c(CN3C(=O)C4(CC4)c4ccncc43)nc3cc(Cl)ccc32)CC1=O] | 1'-{[5-Chloro-1-(1-ethyl-5-oxopyrrolidin-3-yl)-1H-benzimidazol-2-yl]methyl}spiro[cyclopropane-1,3'-pyrrolo[2,3-c]pyridin]-2'(1'H)-one | 0.0011 |

TABLE 1-continued

Structure, name and activity data of particular compounds

| Example No. | Structure | Name | CPE Long EC$_{50}$ (μM) |
|---|---|---|---|
| 9-1 | Chiral | 1'-({5-Chloro-1-[(3S)-1,1-dioxidotetrahydrothiophen-3-yl]-7-fluoro-1H-benzimidazol-2-yl}methyl)spiro[cyclopropane-1,3'-pyrrolo[2,3-c]pyridin]-2'(1'H)-one | 0.013 |
| 9-2 | Chiral | 1'-({5-Chloro-1-[(3R)-1,1-dioxidotetrahydrothiophen-3-yl]-7-fluoro-1H-benzimidazol-2-yl}methyl)spiro[cyclopropane-1,3'-pyrrolo[2,3-c]pyridin]-2'(1'H)-one | 0.0007 |
| 10-1 | 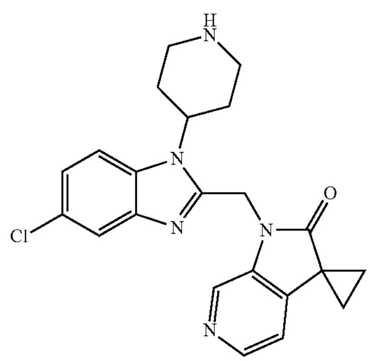 [SMILES: O=C1N(Cc2nc3cc(Cl)ccc3n2C2CCNCC2)c2cnccc2C12CC2] | 1'-{[5-Chloro-1-(piperidin-4-yl)-1H-benzimidazol-2-yl]methyl}spiro[cyclopropane-1,3'-pyrrolo[2,3-c]pyridin]-2'(1'H)-one | 0.078 |
| 10-2 | 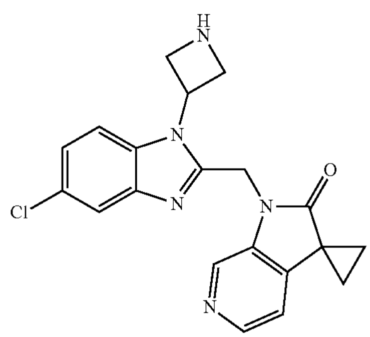 [SMILES: O=C1N(Cc2nc3cc(Cl)ccc3n2C2CNC2)c2cnccc2C12CC2] | 1'-{[1-(Azetidin-3-yl)-5-chloro-1H-benzimidazol-2-yl]methyl}spiro[cyclopropane-1,3'-pyrrolo[2,3-c]pyridin]-2'(1'H)-one | 0.138 |

TABLE 1-continued

Structure, name and activity data of particular compounds

| Example No. | Structure | | Name | CPE Long EC$_{50}$ (μM) |
|---|---|---|---|---|
| 11 | 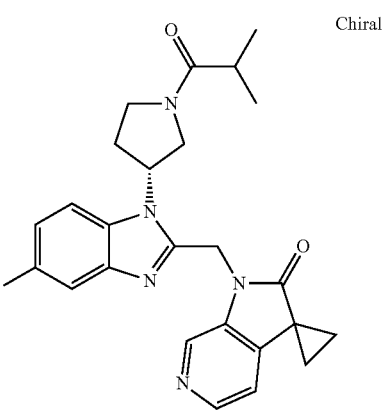 | Chiral | 1'-({5-Chloro-1-[(3R)-1-(2-methylpropanoyl)pyrrolidin-3-yl]-1H-benzimidazol-2-yl}methyl)spiro[cyclopropane-1,3'-pyrrolo[2,3-c]pyridin]-2'(1'H)-one | 0.003 |
| 12 | 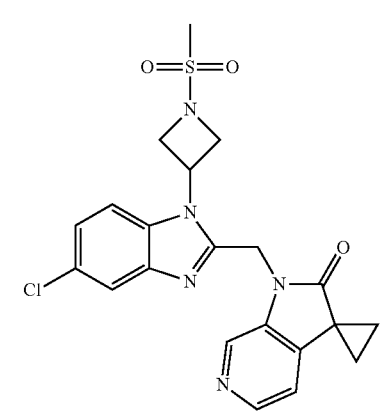 [SMILES: CS(=O)(=O)N1CC(n2c(CN3C(=O)C4(CC4)c4ccncc43)nc3cc(Cl)ccc32)C1] | | 1'-({5-Chloro-1-[1-(methylsulfonyl)azetidin-3-yl]-1H-benzimidazol-2-yl}methyl)spiro[cyclopropane-1,3'-pyrrolo[2,3-c]pyridin]-2'(1'H)-one | 0.0018 |
| 13 | 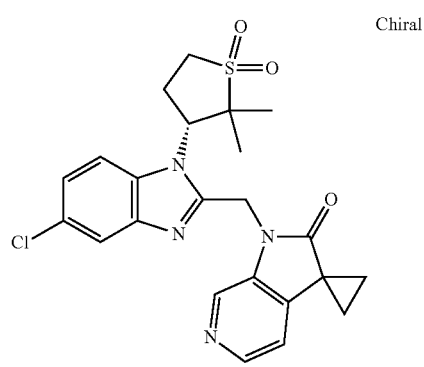 [SMILES: CC1(C)[C@H](n2c(CN3C(=O)C4(CC4)c4ccncc43)nc3cc(Cl)ccc32)CCS1(=O)=O] | Chiral | 1'-{[5-Chloro-1-(2,2-dimethyl-1,1-dioxidotetrahydrothiophen-3-yl)-1H-benzimidazol-2-yl]methyl}spiro[cyclopropane-1,3'-pyrrolo[2,3-c]pyridin]-2'(1'H)-one | 0.397 |

TABLE 1-continued

Structure, name and activity data of particular compounds

| Example No. | Structure | Name | CPE Long EC$_{50}$ (μM) |
|---|---|---|---|
| 14-1 | 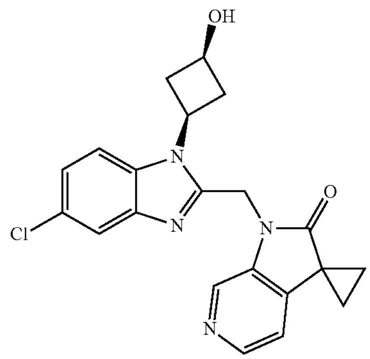 [SMILES: O=C1N(Cc2nc3cc(Cl)ccc3n2[C@H]2C[C@@H](O)C2)c2cnccc2C12CC2] | 1'-{[5-Chloro-1-(cis-3-hydroxycyclobutyl)-1H-benzimidazol-2-yl]methyl}spiro[cyclopropane-1,3'-pyrrolo[2,3-c]pyridin]-2'(1'H)-one | 0.007 |
| 14-2 | 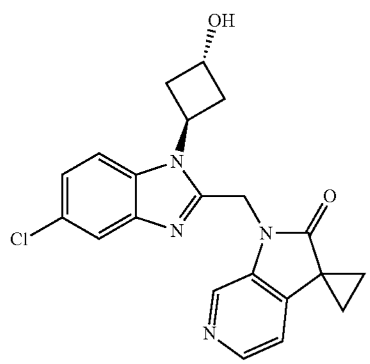 [SMILES: O=C1N(Cc2nc3cc(Cl)ccc3n2[C@H]2C[C@H](O)C2)c2cnccc2C12CC2] | 1'-{[5-Chloro-1-(trans-3-hydroxycyclobutyl)-1H-benzimidazol-2-yl]methyl}spiro[cyclopropane-1,3'-pyrrolo[2,3-c]pyridin]-2'(1'H)-one | 0.0008 |
| 15 | 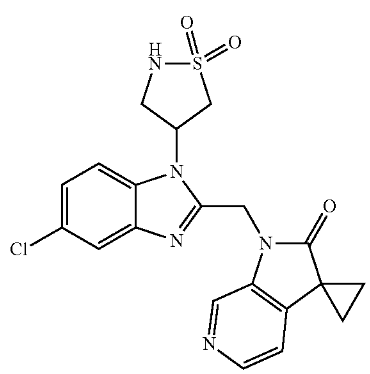 [SMILES: O=C1N(Cc2nc3cc(Cl)ccc3n2C2CNS(=O)(=O)C2)c2cnccc2C12CC2] | 1'-{[5-Chloro-1-(1,1-dioxido-1,2-thiazolidin-4-yl)-1H-benzimidazol-2-yl]methyl}spiro[cyclopropane-1,3'-pyrrolo[2,3-c]pyridin]-2'(1'H)-one | 0.0016 |
| 16 | 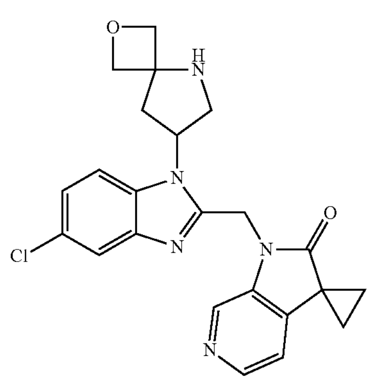 [SMILES: O=C1N(Cc2nc3cc(Cl)ccc3n2C2CNC3(COC3)C2)c2cnccc2C12CC2] | 1'-{[5-Chloro-1-(2-oxa-5-azaspiro[3.4]oct-7-yl)-1H-benzimidazol-2-yl]methyl}spiro[cyclopropane-1,3'-pyrrolo[2,3-c]pyridin]-2'(1'H)-one | 0.0022 |

TABLE 1-continued

Structure, name and activity data of particular compounds

| Example No. | Structure | Name | CPE Long EC$_{50}$ (μM) |
|---|---|---|---|
| 17 | 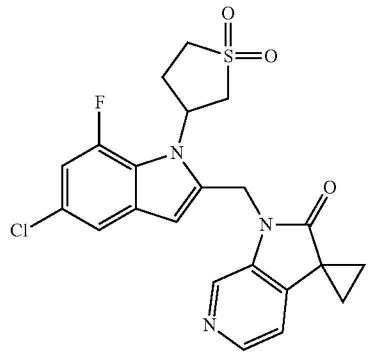 [SMILES: O=C1N(Cc2cc3cc(Cl)cc(F)c3n2C2CCS(=O)(=O)C2)c2cnccc2C12CC2] | 1'-{[5-Chloro-1-(1,1-dioxidotetrahydrothiophen-3-yl)-7-fluoro-1H-indol-2-yl]methyl}spiro[cyclopropane-1,3'-pyrrolo[2,3-c]pyridin]-2'(1'H)-one | 0.0006 |
| 18 | 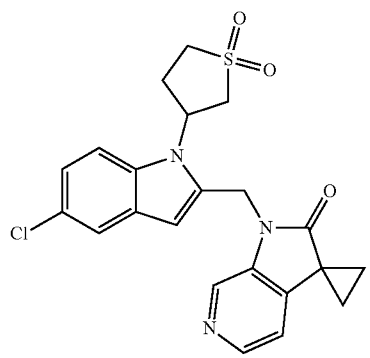 [SMILES: O=C1N(Cc2cc3cc(Cl)ccc3n2C2CCS(=O)(=O)C2)c2cnccc2C12CC2] | 1'-{[5-Chloro-1-(1,1-dioxidotetrahydrothiophen-3-yl)-1H-indol-2-yl]methyl}spiro[cyclopropane-1,3'-pyrrolo[2,3-c]pyridin]-2'(1'H)-one | 0.0019 |
| 19 | 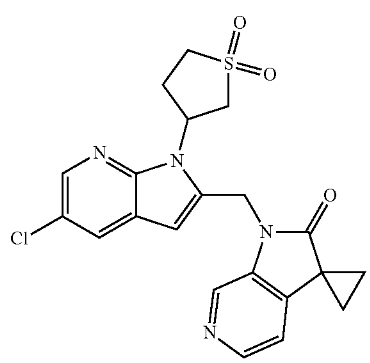 [SMILES: O=C1N(Cc2cc3cc(Cl)cnc3n2C2CCS(=O)(=O)C2)c2cnccc2C12CC2] | 1-{[5-Chloro-1-(1,1-dioxidotetrahydrothiophen-3-yl)-1H-pyrrolo[2,3-b]pyridin-2-yl]methyl}spiro[cyclopropane-1,3'-pyrrolo[2,3-c]pyridin]-2'(1'H)-one ' | 0.006 |

TABLE 2

NMR and MS data of particular compounds

| Example No. | $^1$H NMR data | MW data |
|---|---|---|
| 1-1 | $^1$H NMR (400 MHz, CD$_3$Cl) δ ppm 8.82 (s, 1 H), 8.35-8.34 (d, J = 4.8 Hz, 1 H), 8.10-8.08 (d, J = 8.8 Hz, 1 H), 7.77-7.76 (d, J = 2 Hz, 1 H), 7.32-7.30 (dd, J = 2, 2 Hz, 1 H), 6.80-6.79 (d, J = 4.8 Hz, 1 H), 5.62-5.53 (m, 1 H), 5.31 (s, 2 H), 3.75-3.67 (m, 1 H), 3.49-3.41 (m, 1 H), 2.91 (s, 3 H), 2.71-2.62 (m, 2 H), 1.91-1.88 (m, 2 H), 1.72-1.69 (m, 2 H) | MS obsd. (ESI$^+$) [(M + H)$^+$] 457 |
| 1-2 | $^1$H NMR (400 MHz, CDCl$_3$) δ ppm 8.461 (s, 1 H), 8.32-8.31 (m, 1 H), 7.80-7.79 (d, J = 2 Hz, 1 H), 7.46-7.44 (d, J = 8.8 Hz, 1 H), 7.29-7.28 (d, J = 2 Hz, 1 H), 6.82-6.81 (d, J = 4.8 Hz, 1 H), 5.62-5.58 (m, 1 H), 5.31 (s, 2 H), 3.93-3.87 (m, 1 H), 3.35-3.26 (m, 1 H), 3.01-2.94 (m, 5 H), 2.03-1.99 (m, 2 H), 1.72-1.68 (m, 2 H) | MS obsd. (ESI$^+$) [(M + H)$^+$] 457 |

TABLE 2-continued

NMR and MS data of particular compounds

| Example No. | $^1$H NMR data | MW data |
|---|---|---|
| 2-1 | $^1$H NMR (400 MHz, CDCl$_3$) δ ppm 8.76 (br. s., 5 H), 8.34 (br. s., 1 H), 7.79 (br. s., 1 H), 7.38 (d, J = 8.28 Hz, 1 H), 7.24 (br. s., 1 H), 6.80 (br. s., 1 H), 5.48 (t, J = 8.16 Hz, 1 H), 5.31 (br. s., 2 H), 4.36 (br. s., 2 H), 4.29 (br. s., 2 H), 3.30-3.13 (m, 2 H), 2.70 (br. s., 2 H), 1.91 (br. s., 2 H), 1.73 (br. s, 2 H) | MS obsd. (ESI$^+$) [(M + H)$^+$] 469 |
| 2-2 | $^1$H NMR (400 MHz, CD$_3$OD) δ ppm 8.50 (s, 1 H), 8.33-8.21 (m, 1 H), 7.74-7.62 (m, 2 H), 7.40-7.29 (m, 1 H), 7.20-7.10 (m, 1 H), 5.45 (s, 2 H), 5.20-5.05 (m, 1 H), 3.57-3.40 (m, 2 H), 3.30-3.22 (m, 2 H), 3.15-3.01 (m, 2 H), 2.35-2.21 (m, 2 H), 1.91 (s, 4 H) | MS obsd. (ESI$^+$) [(M + H)$^+$] 457 |
| 2-3 | $^1$H NMR (400 MHz, CD$_3$OD) δ ppm 8.35 (d, J = 0.76 Hz, 1 H), 8.26 (d, J = 5.05 Hz, 1 H), 7.69-7.54 (m, 2 H), 7.34-7.24 (m, 1 H), 7.21-7.12 (m, 1 H), 5.45 (s, 2 H), 5.20-5.05 (m, 1 H), 2.05 (m, 8 H), 1.91 (m, 4 H) | MS obsd. (ESI$^+$) [(M + H)$^+$] 393 |
| 2-4 | $^1$H NMR (400 MHz, CD$_3$OD) δ ppm 8.37 (s, 1 H), 8.27 (d, J = 5.05 Hz, 1 H), 8.19 (d, J = 8.59 Hz, 1 H), 7.64 (d, J = 1.77 Hz, 1 H), 7.40 (dd, J = 8.84, 2.02 Hz, 1 H), 7.16 (dd, J = 5.05, 0.76 Hz, 1 H), 6.03-5.95 (m, 1 H), 5.40 (s, 2 H), 5.31-5.16 (m, 4 H), 2.06 (s, 1 H) | MS obsd. (ESI$^+$) [(M + H)$^+$] 381 |
| 2-5 | $^1$H NMR (400 MHz, CD$_3$OD) δ ppm 8.42-8.23 (m, 2 H), 7.73-7.60 (m, 2 H), 7.42-7.30 (m, 1 H), 7.27-7.11 (m, 1 H), 5.45 (s, 2 H), 5.41-5.31 (m, 1 H), 3.69-3.48 (m, 2 H), 3.31-3.17 (m, 2 H), 1.91 (m, 4 H) | MS obsd. (ESI$^+$) [(M + H)$^+$] 415 |
| 2-6 | $^1$H NMR (400 MHz, CD$_3$OD) δ ppm 8.42 (s, 1 H), 8.26 (d, J = 4.80 Hz, 1 H), 7.74 (d, J = 8.84 Hz, 1 H), 7.65 (d, J = 1.77 Hz, 1 H), 7.30 (dd, J = 8.72, 2.15 Hz, 1 H), 7.15 (dd, J = 4.93, 0.88 Hz, 1 H), 5.49 (s, 2 H), 4.96-4.90 (m, 1 H), 4.20-4.08 (m, 2 H), 3.61 (d, J = 1.77 Hz, 2 H), 2.64-2.45 (m, 2 H), 1.90 (m, 4 H), 1.84-1.72 (m, 2 H) | MS obsd. (ESI$^+$) [(M + H)$^+$] 409 |
| 2-7 | $^1$H NMR (400 MHz, CD$_3$OD) δ ppm 8.37 (d, J = 0.76 Hz, 1 H), 8.25 (d, J = 4.80 Hz, 1 H), 7.77-7.62 (m, 2 H), 7.35-7.22 (m, 1 H), 7.19-7.11 (m, 1 H), 5.46 (s, 2 H), 4.69-4.54 (m, 1 H), 3.85-3.73 (m, 1 H), 2.44-2.28 (m, 2 H), 2.20-2.04 (m, 2 H), 1.98-1.88 (m, 4 H), 1.86-1.72 (m, 2 H), 1.62-1.45 (m, 2 H) | MS obsd. (ESI$^+$) [(M + H)$^+$] 423 |
| 2-8 | $^1$H NMR (400 MHz, CD$_3$OD) δ ppm 8.36 (s, 1 H), 8.30-8.23 (m, 1 H), 8.07 (s, 1 H), 7.63 (d, J = 2.02 Hz, 1 H), 7.36-7.21 (m, 1 H), 7.21-7.13 (m, 1 H), 5.45 (d, J = 8.84 Hz, 2 H), 5.23-5.07 (m, 1 H), 4.53-4.38 (m, 1 H), 2.60-2.40 (m, 2 H), 2.24-2.09 (m, 2 H), 2.03-1.94 (m, 2 H), 1.91 (d, J = 1.52 Hz, 4 H) | MS obsd. (ESI$^+$) [(M + H)$^+$] 409 |
| 2-9 | $^1$H NMR (400 MHz, DMSO-d$_6$) δ ppm 8.45 (br. s., 1 H), 8.36 (s, 1 H), 8.27 (d, J = 4.80 Hz, 1 H), 7.72 (d, J = 2.02 Hz, 1 H), 7.35 (s, 1 H), 7.27 (dd, J = 8.84, 2.02 Hz, 1 H), 7.18 (dd, J = 4.80, 0.76 Hz, 1 H), 5.61 (s, 1 H), 5.47-5.23 (m, 2 H), 3.52 (s, 1 H), 3.46-3.36 (m, 1 H), 2.71-2.57 (m, 1 H), 2.47-2.36 (m, 1 H), 1.86 (d, J = 4.04 Hz, 2 H), 1.78-1.66 (m, 2 H) | MS obsd. (ESI$^+$) [(M + H)$^+$] 408 |
| 2-10 | $^1$H NMR (400 MHz, DMSO-d$_6$) δ ppm 8.42 (s, 1 H), 8.26 (d, J = 4.80 Hz, 1 H), 7.87 (d, J = 8.84 Hz, 1 H), 7.81 (s, 1 H), 7.72 (d, J = 2.02 Hz, 1 H), 7.22 (dd, J = 8.72, 2.15 Hz, 1 H), 7.18 (dd, J = 4.80, 0.76 Hz, 1 H), 5.55-5.35 (m, 2 H), 5.06 (dd, J = 5.68, 3.41 Hz, 1 H), 3.30 (d, J = 7.83 Hz, 2 H), 2.94 (d, J = 16.67, 11.87 Hz, 1 H), 2.72-2.53 (m, 2 H), 1.91-1.79 (m, 2 H), 1.74-1.64 (m, 2 H) | MS obsd. (ESI$^+$) [(M + H)$^+$] 422 |
| 2-11 | $^1$H NMR (400 MHz, CD$_3$OD) δ ppm 8.41 (d, J = 0.76 Hz, 1 H), 8.27 (d, J = 5.05 Hz, 1 H), 7.68-7.57 (m, 2 H), 7.33 (dd, J = 8.84, 2.02 Hz, 1 H), 7.17 (dd, J = 4.93, 0.88 Hz, 1 H), 5.47 (d, J = 2.53 Hz, 3 H), 2.91-2.61 (m, 3 H), 2.61-2.45 (m, 2 H), 2.36-2.19 (m, 2 H), 1.91 (s, 4 H) | MS obsd. (ESI$^+$) [(M + H)$^+$] 429 |
| 2-12 | $^1$H NMR (400 MHz, DMSO-d$_6$) δ ppm 8.38 (s, 1 H), 8.24 (d, J = 4.77 Hz, 1 H), 7.76-7.69 (m, 2 H), 7.22-7.13 (m, 2 H), 5.38 (s, 2 H), 5.35-5.23 (m, 1 H), 4.56-4.38 (m, 1 H), 2.45-1.98 (m, 5 H), 1.89-1.81 (m, 2 H), 1.71 (d, J = 4.27 Hz, 2 H), 1.42 (d, J = 12.80 Hz, 3 H) | MS obsd. (ESI$^+$) [(M + H)$^+$] 451 |
| 2-13 | $^1$H NMR (400 MHz, CD$_3$OD) δ ppm 8.48 (s, 1 H), 8.40 (d, J = 2.26 Hz, 1 H), 8.29 (d, J = 4.77 Hz, 1 H), 8.05 (d, J = 2.26 Hz, 1 H), 7.17 (d, J = 5.02 Hz, 1 H), 5.71 (t, J = 8.16 Hz, 1 H), 5.60-5.45 (m, 2 H), 4.22 (dd, J = 13.05, 10.29 Hz, 1 H), 3.72 (m, 1 H), 3.59 (dd, J = 12.92, 8.16 Hz, 1 H), 3.40-3.26 (m, 1 H), 3.25-3.13 (m, 1 H), 2.69 (dd, J = 12.55, 5.27 Hz, 1 H), 1.99-1.83 (m, 4 H) | MS obsd. (ESI$^+$) [(M + H)$^+$] 444 |
| 2-14 | $^1$H NMR (400 MHz, DMSO-d$_6$) δ ppm 8.39 (s, 1 H), 8.26 (d, J = 4.8 Hz, 1 H), 7.70 (m, 2 H), 7.28 (dd, J = 8.8, 2.0 Hz, 1 H), 7.18 (d, J = 4.8 Hz, 1 H), 5.53-5.37 (m, 3 H), 427 (m, 1 H), 4.11 (m, 1 H), 3.93 (dd, J = 10.4, 7.6 Hz, 1 H), 3.70 (m, 1 H), 2.45 (m, 1 H), 2.06 (m, 1 H), 1.87 (dd, J = 8.0, 4.0 Hz, 2 H), 1.74 (dd, J = 8.0, 4.0 Hz, 2 H) | MS obsd. (ESI$^+$) [(M + H)$^+$] 395 |
| 2-15 | $^1$H NMR (400 MHz, DMSO-d$_6$) δ ppm 8.40 (s, 1 H), 8.27 (d, J = 4.8 Hz, 1 H), 7.72 (d, J = 2.0 Hz, 1 H), 7.65 (d, J = 8.4 Hz, 1 H), 7.25 (dd, J = 8.8, 2.0 Hz, 1 H), 7.18 (d, J = 4.8 Hz, 1 H), 5.52-5.37 (m, 3 H), 3.79 (m, 1 H), 3.66 (m, 2 H), 3.40 (m, 1 H), 2.5 (m, 1 H), 2.30-2.26 (m, 1 H), 1.87 (dd, J = 8.0, 4.0 Hz, 2 H), 1.74 (dd, J = 8.0, 4.0 Hz, 2 H), 1.43 (s, 9 H) | MS obsd. (ESI$^+$) [(M + H)$^+$] 494 |

TABLE 2-continued

NMR and MS data of particular compounds

| Example No. | $^1$H NMR data | MW data |
|---|---|---|
| 2-16 | $^1$H NMR (400 MHz, DMSO-d$_6$) δ ppm 8.23 (t, J = 4.0 Hz, 2 H), 7.74 (d, J = 8.0 Hz, 1 H), 7.65 (s, 1 H), 7.21-7.16 (m, 2 H), 5.37 (s, 2 H), 5.09 (s, 2 H), 4.75-4.68 (m, 1 H), 3.99 (dd, J = 12.0, 8.0 Hz, 2 H), 3.86 (dd, J = 8.0, 4.0 Hz, 2 H), 1.87 (dd, J = 8.0, 4.0 Hz, 2 H), 1.74 (dd, J = 8.0, 4.0 Hz, 2 H) | MS obsd. (ESI$^+$) [(M + H)$^+$] 399 |
| 2-17 | $^1$H NMR (400 MHz, CD$_3$OD) δ ppm 8.26 (d, J = 8.0 Hz, 1 H), 8.23 (s, 1 H), 7.65 (d, J = 8.0 Hz, 1 H), 7.58 (d, J = 4.0 Hz, 1 H), 7.31 (d, J = 8.0 Hz, 1 H), 7.18 (d, J = 4.0 Hz, 1 H), 5.38 (m, 1 H), 2.96-2.91 (m, 2 H), 2.68-2.63 (m, 2 H), 1.94-1.89 (m, 4 H), 1.56 (s, 3 H) | MS obsd. (ESI$^+$) [(M + H)$^+$] 409 |
| 3-1 | $^1$H NMR (400 MHz, CD$_3$OD) δ ppm 8.48 (d, J = 0.76 Hz, 1 H), 8.29 (d, J = 5.05 Hz, 1 H), 7.83 (d, J = 8.84 Hz, 1 H), 7.66 (d, J = 2.02 Hz, 1 H), 7.37 (d, J = 2.02 Hz, 1 H), 7.17 (dd, J = 4.93, 0.88 Hz, 1 H), 5.74-5.91 (m, 1 H), 5.50 (d, J = 12.13 Hz, 2 H), 3.60-3.78 (m, 2 H), 3.47-3.60 (m, 1 H), 3.27-3.39 (m, 1 H), 2.82-3.01 (m, 1 H), 2.61-2.74 (m, 1 H), 1.86-1.98 (m, 4 H) | MS obsd. (ESI$^+$) [(M + H)$^+$] 443 |
| 3-2 | $^1$H NMR (400 MHz, DMSO-d$_6$) δ ppm 8.42-8.38 (m, 1 H), 8.29-8.24 (m, 1 H), 7.76-7.69 (m, 2 H), 7.37-7.31 (m, 1 H), 7.20-7.15 (m, 1 H), 5.78-5.64 (m, 1 H), 5.56-5.40 (m, 2 H), 3.86-3.75 (m, 1 H), 3.68-3.56 (m, 2 H), 3.32-3.20 (m, 1 H), 2.75-2.64 (m, 2 H), 1.90-1.83 (m, 2 H), 1.75-1.69 (m, 2 H) | MS obsd. (ESI$^+$) [(M + H)$^+$] 443 |
| 3-3 | $^1$H NMR (400 MHz, DMSO-d$_6$) δ ppm 8.43-8.39 (m, 1 H), 8.30-8.25 (m, 1 H), 7.76-7.69 (m, 2 H), 7.37-7.29 (m, 1 H), 7.20-7.14 (m, 1 H), 5.78-5.62 (m, 1 H), 5.56-5.39 (m, 2 H), 3.88-3.76 (m, 1 H), 3.69-3.55 (m, 2 H), 3.32-3.20 (m, 1 H), 2.77-2.63 (m, 2 H), 1.90-1.81 (m, 2 H), 1.78-1.69 (m, 2 H) | MS obsd. (ESI$^+$) [(M + H)$^+$] 443 |
| 4-1 | $^1$H NMR (400 MHz, DMSO-d$_6$) δ ppm 8.38 (s, 1 H), 8.27 (d, J = 4.0 Hz, 1 H), 7.88 (d, J = 8.0 Hz, 1 H), 7.76 (s, 1 H), 7.41 (dd, J = 8.0, 4.0 Hz, 1 H), 7.19 (d, J = 4.0 Hz, 1 H), 5.96-5.87 (m, 1 H), 5.49 (s, 2 H), 5.03 (dd, J = 16.0, 4.0 Hz, 2 H), 4.83 (dd, J = 16.0, 4.0 Hz, 2 H), 1.87 (dd, J = 8.0, 4.0 Hz, 2 H), 1.74 (dd, J = 8.0, 4.0 Hz, 2 H) | MS obsd. (ESI$^+$) [(M + H)$^+$] 429 |
| 4-2 | $^1$H NMR (400 MHz, DMSO-d$_6$) δ ppm 8.43 (br. s., 1 H), 8.33 (br. s., 1 H), 7.88 (d, J = 6.78 Hz, 1 H), 7.72 (br. s., 1 H), 7.49 (br. s., 1 H), 7.42 (br. s., 1 H), 5.90 (br. s., 1 H), 5.41 (br. s., 2 H), 5.01 (br. s., 2 H), 4.80 (br. s., 2 H), 1.38 (br. s., 6 H) | MS obsd. (ESI$^+$) [(M + H)$^+$] 431 |
| 4-3 | MS obsd. (ESI$^+$) [(M + H)$^+$] 459, $^1$H NMR (400 MHz, DMSO-d$_6$) δ ppm 8.40 (s, 1 H), 8.37 (d, J = 4.77 Hz, 1 H), 7.89 (d, J = 8.78 Hz, 1 H), 7.62 (d, J = 2.01 Hz, 1 H), 7.45-7.37 (m, 2 H), 6.01-5.87 (m, 1 H), 5.44 (s, 2 H), 5.04 (dd, J = 16.06, 6.78 Hz, 2 H), 4.85 (dd, J = 15.94, 10.42 Hz, 2 H), 1.95-1.76 (m, 4 H), 0.58 (t, J = 7.40 Hz, 6 H) | MS obsd. (ESI$^+$) [(M + H)$^+$] 459 |
| 5 | $^1$H NMR (400 MHz, DMSO-d$_6$) δ ppm 8.35 (s, 1 H), 8.26 (d, J = 4.0 Hz, 1 H), 7.93 (d, J = 8.0 Hz, 1 H), 7.72 (d, J = 4.0 Hz, 1 H), 7.29 (dd, J = 8.0, 4.0 Hz, 1 H), 7.18 (d, J = 4.0 Hz, 1 H), 6.50 (m, 1 H), 5.48 (s, 2 H), 4.28-4.22 (m, 2 H), 3.61-3.55 (m, 2 H), 1.87 (dd, J = 8.0, 4.0 Hz, 2 H), 1.74 (dd, J = 8.0, 4.0 Hz, 2 H) | MS obsd. (ESI$^+$) [(M + H)$^+$] 413 |
| 6 | $^1$H NMR (400 MHz, DMSO-d$_6$) δ ppm 8.38 (s, 1 H), 8.27 (d, J = 4.0 Hz, 1 H), 7.64 (s, 1 H), 7.43 (d, J = 12.0 Hz, 1 H), 7.18 (d, J = 8.0 Hz, 1 H), 5.91-5.84 (m, 1 H), 5.59 (s, 2 H), 4.84 (m, 2 H), 4.67 (m, 2 H), 1.87 (dd, J = 8.0, 4.0 Hz, 2 H), 1.74 (dd, J = 8.0, 4.0 Hz, 2 H) | MS obsd. (ESI$^+$) [(M + H)$^+$] 447 |
| 7-1 | $^1$H NMR (400 MHz, DMSO-d$^6$) δ ppm 8.41 (s, 1 H), 8.27-8.25 (d, J = 5.2 Hz, 1 H), 7.89-7.87 (d, J = 8.8 Hz, 1 H), 7.73-7.71 (m, 2 H), 7.23-7.18 (m, 2 H), 5.56-5.41 (m, 2 H), 5.05-5.03 (m, 1 H), 3.35-3.34 (m, 1 H), 2.76-2.67 (m, 1 H), 2.44-2.38 (m, 2 H), 1.92-1.86 (m, 3 H), 1.72-1.70 (m, 2 H) | MS obsd. (ESI$^+$) [(M + Na)$^+$] 444 |
| 7-2 | $^1$H NMR (400 MHz, CDCl$_3$) δ ppm 8.54 (s, 1 H), 8.16-8.15 (d, J = 4.4 Hz, 1 H), 7.58 (s, 1 H), 7.35 (s, 1 H), 7.16-7.14 (m, 1 H), 7.06-7.04 (m, 1 H), 6.68-6.67 (d, J = 4 Hz, 1 H), 5.61 (m, 1 H), 5.23-5.13 (dd, J$_1$ = 15.2 Hz, J$_2$ = 28.8 Hz, 2 H), 3.70-3.67 (m, 1 H), 3.46-3.43 (m, 1 H), 2.47 (m, 2 H), 1.73 (s, 2 H), 1.57 (s, 2 H) | MS obsd. (ESI$^+$) [(M + H)$^+$] 408 |
| 8-1 | $^1$H NMR (400 MHz, CDCl$_3$) δ ppm 8.76 (s, 1 H), 8.35 (s, 1 H), 7.79 (s, 1 H), 7.26-7.21 (m, 1 H), 7.06-7.04 (d, J = 8 Hz, 1 H), 6.81 (s, 1 H), 5.73 (s, 1 H), 5.42-5.38 (b, J = 14.8 Hz, 1 H), 5.29 (b, J = 15.2, 1 H), 3.86-3.81 (m, 1 H), 3.65-3.63 (b, J = 8.4 Hz, 1 H), 2.98 (s, 3 H), 2.86-2.68 (m, 2 H), 1.91 (s, 2 H), 1.72 (s, 2 H | MS obsd. (ESI$^+$) [(M + H)$^+$] 422 |
| 8-2 | $^1$H NMR (400 MHz, CDCl$_3$) δ ppm 8.77 (s, 1 H), 8.36-8.35 (d, J = 4.8 Hz, 1 H), 7.8 (d, J = 1.6 Hz, 1 H), 7.24-7.22 (m, 1 H), 7.11-7.09 (d, J = 8.8 Hz, 1 H), 6.82-6.81 (d, J = 4.8 Hz, 1 H), 5.76-5.71 (m, 1 H), 5.42-5.26 (dd, J = 15.2, 46.8 Hz, 2 H), 3.87-3.82 (m, 1 H), 3.65-3.62 (m, 1 H), 3.57-3.50 (m, 1 H), 3.46-3.41 (m, 1 H), 1.93-1.90 (m, 2 H), 1.74-1.70 (m, 2 H), 1.21-1.17 (t, J = 7.6 Hz, 3 H) | MS obsd. (ESI$^+$) [(M + H)$^+$] 436 |
| 9-1 | $^1$H NMR (400 MHz, DMSO-d$^6$) δ ppm 8.38 (s, 1 H), 8.25 (d, J = 4.8 Hz, 1 H), 7.62 (s, 1 H), 7.36 (dd, J = 11.6, 1.2 Hz, 1 H), 7.17 (d, J = 4.4 Hz, 1 H), 5.56 (m, 3 H), 3.87 (m, 1 H), 3.56 (m, 1 H), 3.44 (m, 1 H), 3.35 (m, 1 H), 2.61 (m, 2 H), 1.85 (m, 2 H), 1.72 (m, 2 H) | MS obsd. (ESI$^+$) [(M + H)$^+$] 461 |

TABLE 2-continued

NMR and MS data of particular compounds

| Example No. | $^1$H NMR data | MW data |
|---|---|---|
| 9-2 | $^1$H NMR (400 MHz, DMSO-d$^6$) δ ppm 8.38 (s, 1 H), 8.25 (d, J = 4.8 Hz, 1 H), 7.62 (s, 1 H), 7.38 (dd, J = 11.6, 1.2 Hz, 1 H), 7.17 (d, J = 4.8 Hz, 1 H), 5.56 (m, 3 H), 3.87 (m, 1 H), 3.56 (m, 1 H), 3.44 (m, 1 H), 3.35 (m, 1 H), 2.70 (m, 1 H), 2.55 (m, 1 H), 1.85 (m, 2 H), 1.72 (m, 2 H). | MS obsd. (ESI$^+$) [(M + H)$^+$] 461 |
| 10-1 | $^1$H NMR (400 MHz, CD$_3$OD) δ ppm 8.44-8.37 (m, 1 H), 8.32-8.20 (m, 1 H), 7.88-7.76 (m, 1 H), 7.73-7.61 (m, 1 H), 7.37-7.24 (m, 1 H), 7.20-7.11 (m, 1 H), 5.47 (s, 2 H), 4.82-4.70 (m, 1 H), 3.28-3.15 (m, 2 H), 2.87-2.69 (m, 2 H), 2.52-2.34 (m, 2 H), 1.91 (s, 4 H), 1.85-1.73 (m, 2 H) | MS obsd. (ESI$^+$) [(M + H)$^+$] 408 |
| 10-2 | $^1$H NMR (400 MHz, CD$_3$OD) δ ppm 8.40-8.34 (m, 1 H) 8.29-8.23 (m, 1 H) 8.05-7.94 (m, 1 H) 7.70-7.57 (m, 1 H) 7.42-7.30 (m, 1 H) 7.20-7.12 (m, 1 H) 5.47-5.39 (m, 2 H) 4.51-4.27 (m, 5 H) 2.02-1.85 (m, 4 H) | MS obsd. (ESI$^+$) [(M + H)$^+$] 380 |
| 11 | $^1$H NMR (400 MHz, CDCl$_3$) δ ppm 8.75-8.74 (m, 1 H), 8.34-8.32 (m, 1 H), 7.78-7.76 (m, 1 H), 7.26-7.19 (m, 2 H), 6.81-6.79 (m, 1 H), 5.66-5.49 (m, 1 H), 5.44-5.25 (m, 2 H), 3.99-3.78 (m, 2 H), 3.66-3.51 (m, 1 H), 2.73-2.46 (m, 2 H), 2.37-2.12 (m, 2 H), 1.92-1.84 (m, 2 H), 1.74-1.68 (m, 2 H), 1.21-1.12 (m, 6 H) | MS obsd. (ESI$^+$) [(M + Na)$^+$] 486 |
| 12 | $^1$H NMR (400 MHz, CD$_3$OD) δ ppm 8.42 (s, 1 H), 8.28 (d, J = 5.02 Hz, 1 H), 8.18 (d, J = 8.78 Hz, 1 H), 7.65 (d, J = 1.76 Hz, 1 H), 7.40 (dd, J = 8.78, 2.01 Hz, 1 H), 7.16 (d, J = 4.77 Hz, 1 H), 5.88-5.76 (m, 1 H), 5.43 (s, 2 H), 4.63-4.48 (m, 4 H), 3.14 (s, 3 H), 1.91 (s, 4 H) | MS obsd. (ESI$^+$) [(M + H)$^+$] 458 |
| 13 | $^1$H NMR (400 MHz, DMSO-d$^6$) δ ppm 8.37 (s, 1 H), 8.30-8.28 (d, J = 4.8 Hz, 1 H), 7.92-7.90 (d, J = 8.8 Hz, 1 H), 7.71 (s, 1 H), 7.30-7.28 (d, J = 8.8 Hz, 1 H), 7.22-7.21 (d, J = 4.4 Hz, 1 H), 5.59-5.54 (m, 1 H), 5.31-5.26 (m, 1 H), 3.71-3.66 (m, 1 H), 2.98-2.93 (m, 1 H), 2.69-2.59 (m, 1 H), 2.46-2.45 (m, 1 H), 1.90-1.85 (m, 1 H), 1.73-1.70 (m, 2H), 1.55 (s, 3 H), 1.15 (s, 3 H) | MS obsd. (ESI$^+$) [(M + H)$^+$] 471 |
| 14-1 | $^1$H NMR (400 MHz, CDCl$_3$) δ ppm 8.73 (s, 1 H), 8.34 (d, J = 4.77 Hz, 1 H), 7.83 (d, J = 8.78 Hz, 1 H), 7.78 (d, J = 1.76 Hz, 1 H), 7.26 (d, J = 2.01 Hz, 1 H), 6.81 (d, J = 4.77 Hz, 1 H), 5.33 (s, 2 H), 4.93 (quin, J = 8.70 Hz, 1 H), 4.35 (quin, J = 6.90 Hz, 1 H), 2.95-2.78 (m, 4 H), 1.93 (q, J = 3.93 Hz, 2 H), 1.71 (q, J = 4.00 Hz, 2 H) | MS obsd. (ESI$^+$) [(M + H)$^+$] 395 |
| 14-2 | $^1$H NMR (400 MHz, CD$_3$OD) δ ppm 8.29-8.22 (m, 2 H), 7.77 (d, J = 8.78 Hz, 1 H), 7.60 (d, J = 2.01 Hz, 1 H), 7.32 (dd, J = 8.78, 2.01 Hz, 1 H), 7.17 (d, J = 5.02 Hz, 1 H), 5.56 (quin, J = 8.53 Hz, 1 H), 5.42 (s, 2 H), 4.71 (t, J = 6.90 Hz, 1 H), 3.21-3.10 (m, 2 H), 2.57 (td, J = 11.29, 2.26 Hz, 2 H), 1.96-1.88 (m, 4 H) | MS obsd. (ESI$^+$) [(M + H)$^+$] 395 |
| 15 | $^1$H NMR (400 MHz, DMSO-d$^6$) δ ppm 8.41 (s, 1 H), 8.24-8.29 (m, 1 H), 7.85 (d, J = 8.53 Hz, 1 H), 7.73 (d, J = 1.76 Hz, 1 H), 7.36-7.30 (m, 1 H), 7.18 (d, J = 4.77 Hz, 1 H), 5.76 (t, J = 8.78 Hz, 1 H), 5.49 (s, 2 H), 3.85-3.75 (m, 1 H), 3.72-3.60 (m, 1 H), 3.54-3.37 (m, 2 H), 1.86 (d, J = 5.27 Hz, 2 H), 1.73 (d, J = 7.28 Hz, 2 H) | MS obsd. (ESI$^+$) [(M + H)$^+$] 444 |
| 16 | $^1$H NMR (400 MHz, CDCl$_3$) δ ppm 8.73-8.81 (m, 1 H), 8.36 (d, J = 4.52 Hz, 1 H), 7.82-7.70 (m, 2 H), 7.29 (s, 1 H), 7.26-7.18 (m, 1 H), 6.83 (d, J = 4.52 Hz, 1 H), 5.57-5.40 (m, 2 H), 5.21 (d, J = 15.31 Hz, 1 H), 4.85 (d, J = 6.53 Hz, 1 H), 4.71 (dd, J = 8.91, 6.90 Hz, 2 H), 4.61 (d, J = 6.53 Hz, 1 H), 3.52-3.38 (m, 2 H), 2.43 (dd, J = 13.05, 8.78 Hz, 1 H), 2.30 (dd, J = 12.92, 8.66 Hz, 1 H), 1.97-1.80 (m, 4 H) | MS obsd. (ESI$^+$) [(M + H)$^+$] 436 |
| 17 | $^1$H NMR (400 MHz, DMSO-d$^6$) δ ppm 8.44 (s, 1 H), 8.28 (d, J = 4.80 Hz, 1 H), 7.51 (d, J = 1.77 Hz, 1 H), 7.23-7.20 (m, 1 H), 7.19 (s, 1 H), 6.60 (d, J = 2.02 Hz, 1 H), 5.58-5.51 (m, 1 H), 5.42 (q, J = 1.00 Hz, 2 H), 3.79-3.68 (m, 1 H), 3.56 (dd, J = 12.88, 7.07 Hz, 1 H), 3.44 (t, J = 12.13 Hz, 1 H), 3.26-3.15 (m, 1 H), 2.64-2.54 (m, 1 H), 2.08 (s, 1 H), 1.92-1.83 (m, 1 H), 1.80-1.70 (m, 2 H) | MS obsd. (ESI$^+$) [(M + H)$^+$] 460 |
| 18 | $^1$H NMR (400 MHz, DMSO-d$_6$) δ ppm 8.22 (s, 1 H), 8.14 (s, 1 H), 7.80 (d, J = 2.0 Hz, 1 H), 7.48 (s, 4 H), 7.27 (dd, J = 4.4, 13.2 Hz, 1 H), 7.14 (s, 1 H), 7.12 (m, 2 H), 5.26 (d, J = 4.0 Hz, 2 H), 4.14 (q, J = 7.2 Hz, 2 H), 3.80 (s, 2 H), 1.74 (m, 2 H), 1.54 (m, 2 H), 1.24 (t, J = 7.2 Hz, 3 H) | MS obsd. (ESI$^+$) [(M + H)$^+$] 442 |
| 19 | $^1$H NMR (400 MHz, DMSO-d$_6$) δ ppm 8.46 (s, 1 H), 8.30-8.26 (m, 2 H), 8.10-8.08 (d, J = 2.3 Hz, 1 H), 7.21-7.19 (d, J = 8.0 Hz, 1 H), 6.49 (s, 1 H), 5.51-5.36 (m, 3 H), 4.14 (t, J = 12.0 Hz, 2 H), 3.68-3.60 (m, 2 H), 3.25-3.17 (m, 1 H), 3.12-3.01 (m, 1 H), 1.90-1.85 (m, 2 H), 1.79-1.72 (m, 2 H) | MS obsd. (ESI$^+$) [(M + H)$^+$] 443 |

More particular compounds of formula I include the following:

1'-({5-Chloro-1-[cis-3-(methylsulfonyl)cyclobutyl]-1H-benzimidazol-2-yl}methyl)spiro[cyclopropane-1,3'-pyrrolo[2,3-c]pyridin]-2'(1'H)-one;

1'-({5-Chloro-1-[trans-3-(methylsulfonyl)cyclobutyl]-1H-benzimidazol-2-yl}methyl)spiro[cyclopropane-1,3'-pyrrolo[2,3-c]pyridin]-2'(1'H)-one;

1'-{[5-Chloro-1-(2,2-dioxido-2-thiaspiro[3.3]hept-6-yl)-1H-benzimidazol-2-yl]methyl}spiro[cyclopropane-1,3'-pyrrolo[2,3-c]pyridin]-2'(1'H)-one;

1'-{[5-Chloro-1-(1,1-dioxidotetrahydro-2H-thiopyran-4-yl)-1H-benzimidazol-2-yl]methyl}spiro[cyclopropane-1,3'-pyrrolo[2,3-c]pyridin]-2'(1'H)-one;

1'-{[5-Chloro-1-(4-hydroxycyclohexyl)-1H-benzimidazol-2-yl]methyl}spiro[cyclopropane-1,3'-pyrrolo[2,3-c]pyridin]-2'(1'H)-one;

1'-{[5-Chloro-1-(3-hydroxycyclopentyl)-1H-benzimidazol-2-yl]methyl}spiro[cyclopropane-1,3'-pyrrolo[2,3-c]pyridin]-2'(1'H)-one;

1'-{[5-Chloro-1-(2-oxopiperidin-4-yl)-1H-benzimidazol-2-yl]methyl}spiro[cyclopropane-1,3'-pyrrolo[2,3-c]pyridin]-2'(1'H)-one;

1'-{[5-Chloro-1-(3,3-difluorocyclopentyl)-1H-benzimidazol-2-yl]methyl}spiro[cyclopropane-1,3'-pyrrolo[2,3-c]pyridin]-2'(1'H)-one;

1'-{[6-Chloro-3-(1,1-dioxidotetrahydrothiophen-3-yl)-3H-imidazo[4,5-b]pyridin-2-yl]methyl}spiro[cyclopropane-1,3'-pyrrolo[2,3-c]pyridin]-2'(1'H)-one;

1'-{[5-Chloro-1-(tetrahydrofuran-3-yl)-1H-benzimidazol-2-yl]methyl}spiro[cyclopropane-1,3'-pyrrolo[2,3-c]pyridin]-2'(1'H)-one;

1'-{[5-Chloro-1-(trans-3-hydroxy-3-methylcyclobutyl)-1H-benzimidazol-2-yl]methyl}spiro[cyclopropane-1,3'-pyrrolo[2,3-c]pyridin]-2'(1'H)-one;

1'-{[5-Chloro-1-(1,1-dioxidotetrahydrothiophen-3-yl)-1H-benzimidazol-2-yl]methyl}spiro[cyclopropane-1,3'-pyrrolo[2,3-c]pyridin]-2'(1'H)-one;

1'-({5-Chloro-1-[(3S)-1,1-dioxidotetrahydrothiophen-3-yl]-1H-benzimidazol-2-yl}methyl)spiro[cyclopropane-1,3'-pyrrolo[2,3-c]pyridin]-2'(1'H)-one;

1'-({5-Chloro-1-[(3R)-1,1-dioxidotetrahydrothiophen-3-yl]-1H-benzimidazol-2-yl}methyl)spiro[cyclopropane-1,3'-pyrrolo[2,3-c]pyridin]-2'(1'H)-one;

1'-{[5-Chloro-1-(1,1-dioxidothietan-3-yl)-1H-benzimidazol-2-yl]methyl}spiro[cyclopropane-1,3'-pyrrolo[2,3-c]pyridin]-2'(1'H)-one;

1-{[5-Chloro-1-(1,1-dioxidothietan-3-yl)-1H-benzimidazol-2-yl]methyl}-3,3-dimethyl-1,3-dihydro-2H-pyrrolo[2,3-c]pyridin-2-one;

1'-{[5-Chloro-1-(1-oxidothietan-3-yl)-1H-benzimidazol-2-yl]methyl}spiro[cyclopropane-1,3'-pyrrolo[2,3-c]pyridin]-2'(1'H)-one;

1'-{[5-Chloro-1-(1,1-dioxidothietan-3-yl)-7-fluoro-1H-benzimidazol-2-yl]methyl}spiro[cyclopropane-1,3'-pyrrolo[2,3-c]pyridin]-2'(1'H)-one;

1'-{[5-Chloro-1-(6-oxopiperidin-3-yl)-1H-benzimidazol-2-yl]methyl}spiro[cyclopropane-1,3'-pyrrolo[2,3-c]pyridin]-2'(1'H)-one;

1'-{[5-Chloro-1-(5-oxopyrrolidin-3-yl)-1H-benzimidazol-2-yl]methyl}spiro[cyclopropane-1,3'-pyrrolo[2,3-c]pyridin]-2'(1'H)-one;

1'-{[5-Chloro-1-(1-methyl-5-oxopyrrolidin-3-yl)-1H-benzimidazol-2-yl]methyl}spiro[cyclopropane-1,3'-pyrrolo[2,3-c]pyridin]-2'(1'H)-one;

1'-{[5-Chloro-1-(1-ethyl-5-oxopyrrolidin-3-yl)-1H-benzimidazol-2-yl]methyl}spiro[cyclopropane-1,3'-pyrrolo[2,3-c]pyridin]-2'(1'H)-one;

1'-({5-Chloro-1-[(3S)-1,1-dioxidotetrahydrothiophen-3-yl]-7-fluoro-1H-benzimidazol-2-yl}methyl)spiro[cyclopropane-1,3'-pyrrolo[2,3-c]pyridin]-2'(1'H)-one;

1'-({5-Chloro-1-[(3R)-1,1-dioxidotetrahydrothiophen-3-yl]-7-fluoro-1H-benzimidazol-2-yl}methyl)spiro[cyclopropane-1,3'-pyrrolo[2,3-c]pyridin]-2'(1'H)-one;

1'-({5-Chloro-1-[(3R)-1-(2-methylpropanoyl)pyrrolidin-3-yl]-1H-benzimidazol-2-yl}methyl)spiro[cyclopropane-1,3'-pyrrolo[2,3-c]pyridin]-2'(1'H)-one;

1'-({5-Chloro-1-[1-(methylsulfonyl)azetidin-3-yl]-1H-benzimidazol-2-yl}methyl)spiro[cyclopropane-1,3'-pyrrolo[2,3-c]pyridin]-2'(1'H)-one;

1'-{[5-Chloro-1-(cis-3-hydroxycyclobutyl)-1H-benzimidazol-2-yl]methyl}spiro[cyclopropane-1,3'-pyrrolo[2,3-c]pyridin]-2'(1'H)-one;

1'-{[5-Chloro-1-(trans-3-hydroxycyclobutyl)-1H-benzimidazol-2-yl]methyl}spiro[cyclopropane-1,3'-pyrrolo[2,3-c]pyridin]-2'(1'H)-one;

1'-{[5-Chloro-1-(1,1-dioxido-1,2-thiazolidin-4-yl)-1H-benzimidazol-2-yl]methyl}spiro[cyclopropane-1,3'-pyrrolo[2,3-c]pyridin]-2'(1'H)-one;

1'-{[5-Chloro-1-(2-oxa-5-azaspiro[3.4]oct-7-yl)-1H-benzimidazol-2-yl]methyl}spiro[cyclopropane-1,3'-pyrrolo[2,3-c]pyridin]-2'(1'H)-one;

1'-{[5-Chloro-1-(1,1-dioxidotetrahydrothiophen-3-yl)-7-fluoro-1H-indol-2-yl]methyl}spiro[cyclopropane-1,3'-pyrrolo[2,3-c]pyridin]-2'(1'H)-one;

1'-{[5-Chloro-1-(1,1-dioxidotetrahydrothiophen-3-yl)-1H-indol-2-yl]methyl}spiro[cyclopropane-1,3'-pyrrolo[2,3-c]pyridin]-2'(1'H)-one; and 1'-{[5-Chloro-1-(1,1-dioxidotetrahydrothiophen-3-yl)-1H-pyrrolo[2,3-b]pyridin-2-yl]methyl}spiro[cyclopropane-1,3'-pyrrolo[2,3-c]pyridin]-2'(1'H)-one.

Synthesis

The compounds of the present invention can be prepared by any conventional means. Suitable processes for synthesizing these compounds as well as their starting materials are provided in the schemes below and in the examples. All substituents, in particular, $R^1$ to $R^4$, W and X are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Compound Ia (Scheme 1)

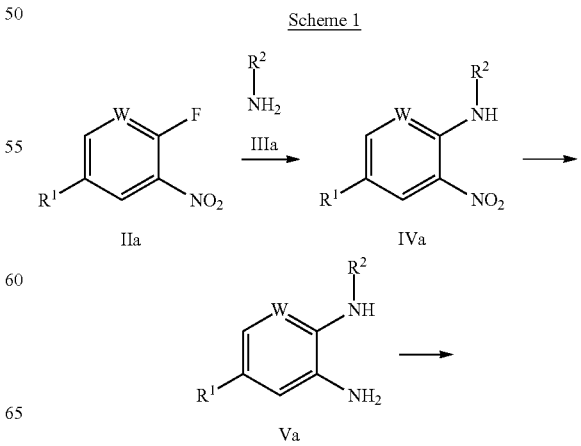

-continued

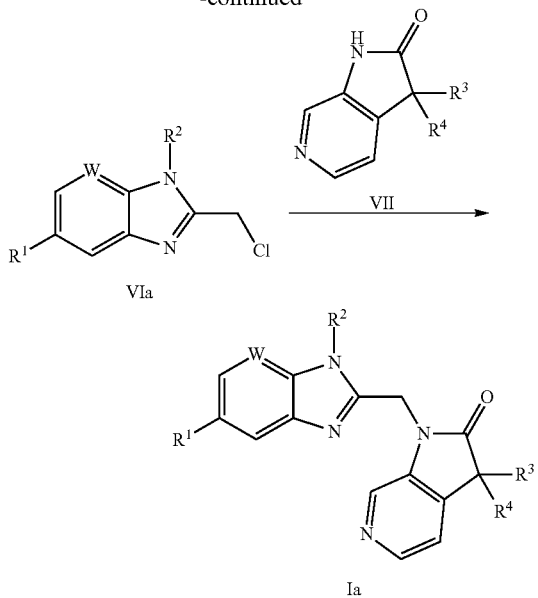

Compound Ia can be prepared according to Scheme 1.

o-Nitro-N-substituted aniline IVa can be generated by reaction of fluorobenzene IIa with amine IIIa. The reaction can be carried out in the presence of a suitable base such as potassium carbonate, cesium carbonate or triethylamine in a suitable organic solvent such as acetonitrile or N,N-dimethylformamide at a temperature between 50° C. and 120° C. for several hours to several days.

Diamine Va can be prepared by reduction of nitro group of o-nitro-N-substituted aniline IVa. The reaction can be carried out in the presence of Raney nickel with hydrazine hydrate in an organic solvent such as methanol or ethanol at a temperature between room temperature and 80° C. for several minutes to several hours. The reaction can also be carried out in the presence of Raney nickel under hydrogen atmosphere at room temperature overnight.

2-(Chloromethyl)benzimidazole VIa can be prepared by reaction of diamine Va with bromoacetic acid. The reaction can be carried out in an aqueous solution of hydrochloric acid at a concentration between 4 N and 12 N at a temperature between 100° C. and 150° C. for several hours to several days. 2-(Chloromethyl)benzimidazole VIa can also be prepared by reaction of diamine Va with 2-chloro-1,1,1-trimethoxyethane or 2-chloro-1,1,1-triethoxyethane. The reaction can be carried out by heating diamine with 2-chloro-1,1,1-trimethoxyethane or 2-chloro-1,1,1-triethoxyethane in the presence or absence of 4-methylbenzenesulfonic acid with or without ethanol at a temperature between 50° C. and 80° C. for several hours. The reaction can also be carried out by heating diamine with 2-chloro-1,1,1-trimethoxyethane or 2-chloro-1,1,1-triethoxyethane with or without ethanol at a temperature between 100° C. and 120° C. for one to several hours under microwave irradiation.

Compound Ia can be prepared by reaction of 2-(chloromethyl)benzimidazole VIa with amide VII. The reaction can be carried out in the presence of a suitable base such as cesium carbonate, sodium hydride or sodium tert-butoxide in an organic solvent such as acetonitrile or N,N-dimethylformamide at a temperature between 0° C. and 100° C. for one to several hours.

General Synthetic Route for Compound Ib (Scheme 2)

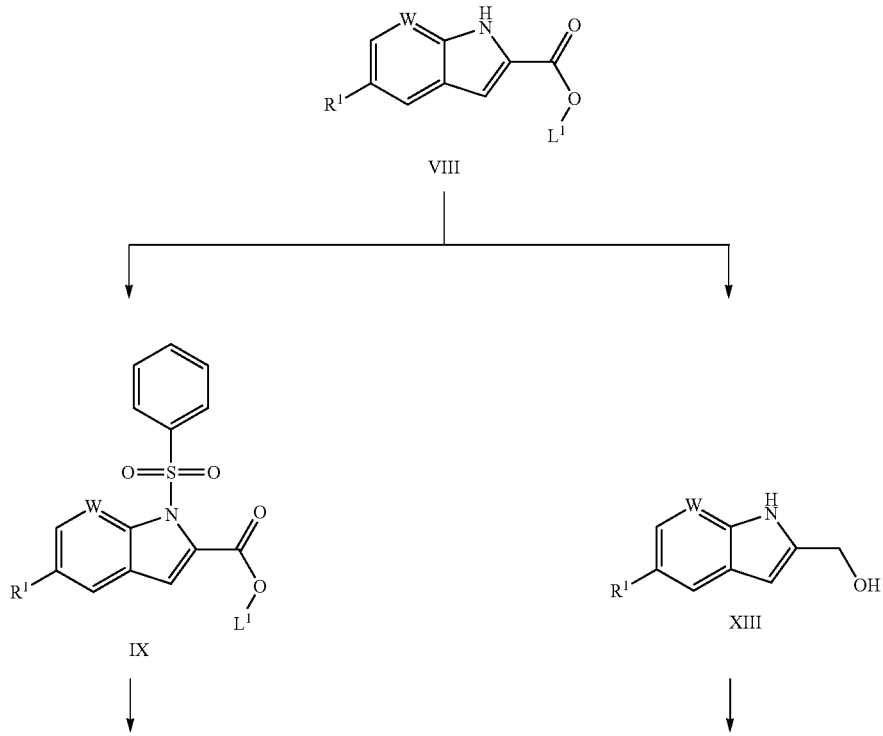

-continued
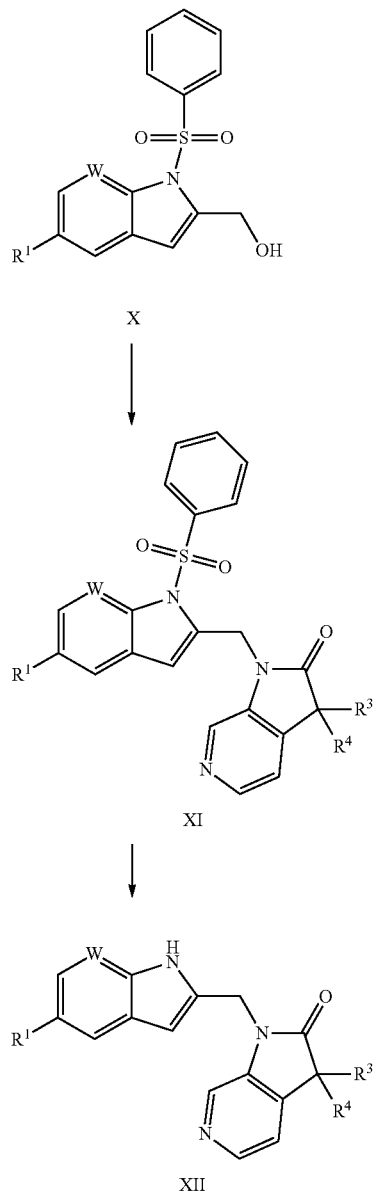
X
XI
XII
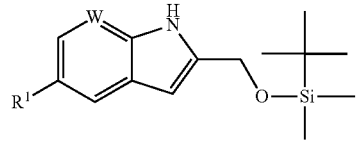
XIV
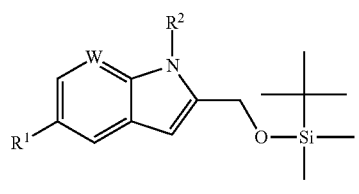
XV
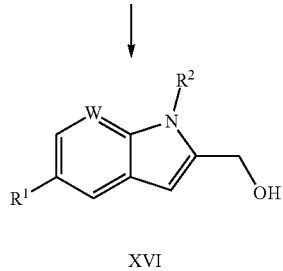
XVI
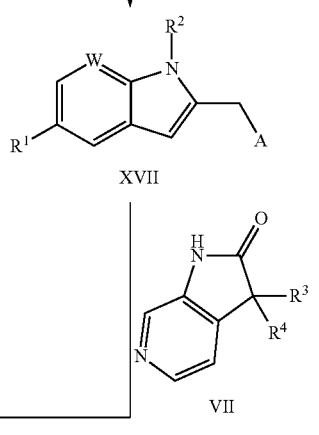
XVII
VII

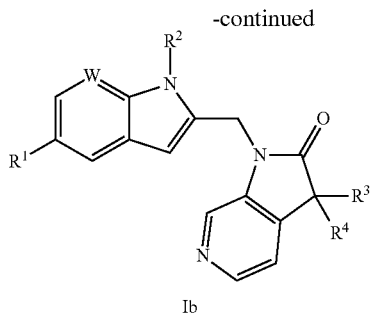

Ib $L^1$ is $C_{1-6}$alkyl;
A is methanesulfonate or chloro;
Y is trifluoromethanesulfonate or bromo.

Compound Ib can be prepared according to Scheme 2.

N-Protected indole IX can be prepared by reaction of indole VIII with benzenesulfonyl chloride. The reaction can be carried out in the presence of sodium hydride in N,N-dimethylformamide at a temperature between 0° C. and room temperature for one to several hours.

Hydroxy X or XIII can be prepared by reduction of ester IX or VIII respectively. The reaction can be carried out by treating ester IX or VIII with lithium aluminum hydride in tetrahydrofuran at a temperature between 0° C. and room temperature for several hours.

Compound XI can be prepared by treating hydroxy X with thionyl chloride or methanesulfonyl chloride and then followed by the reaction with amide VII. Reaction of hydroxy X with thionyl chloride can be carried out in dichloromethane at a temperature between room temperature and 60° C. for 30 minutes to several hours. Reaction of X with methanesulfonyl chloride can be carried out in the presence of trietylamine in dichloromethane at a temperature between 0° C. and room temperature for several hours. The reaction with amide VII can be carried out in the presence of a suitable base such as cesium carbonate, sodium hydride or sodium tert-butoxide in an organic solvent such as acetonitrile or N,N-dimethylformamide at a temperature between 0° C. and 100° C. for one to several hours.

Compound XII can be prepared by deprotection of benzenesulfonyl XI. The reaction can be carried out in the presence of tetrabutylammonium fluoride in tetrahydrofuran at room temperature for several hours.

tert-Butyl(dimethyl)silyloxy XIV can be prepared by reaction of hydroxy XIII with tert-butyl-chloro-dimethylsilane in the presence of imidazole in N,N-dimethylformamide at room temperature for one to several hours.

Compound XV can be prepared by reaction of XIV with intermediate IIIc. The reaction can be carried out in the presence of a base such as cesium carbonate in an organic solvent such as acetonitrile at a temperature between room temperature and 80° C. for several hours or overnight.

Hydroxy XVI can be prepared by cleavage of tert-butyl (dimethyl)silyl of XV. The reaction can be carried out by treating tert-butyl(dimethyl)silyloxy XV with a solution of tetrabutylammonium fluoride in tetrahydrofuran at room temperature for several hours.

Compound XVII can be prepared by treating hydroxy XVI with thionyl chloride or methanesulfonyl chloride.

Compound Ib can be prepared by treating XVII with amide VII. The reaction can be carried out in the presence of a suitable base such as cesium carbonate, sodium hydride or sodium tert-butoxide in an organic solvent such as acetonitrile or N,N-dimethylformamide at a temperature between 0° C. and 100° C. for one to several hours.

Compound Ib can also be prepared by reaction XII with intermediate IIIc. The reaction can be carried out in the presence of a base such as cesium carbonate in an organic solvent such as acetonitrile at a temperature between room temperature and 80° C. for several hours or overnight.

General Synthetic Route for Intermediate IVb (Scheme 3)

Scheme 3

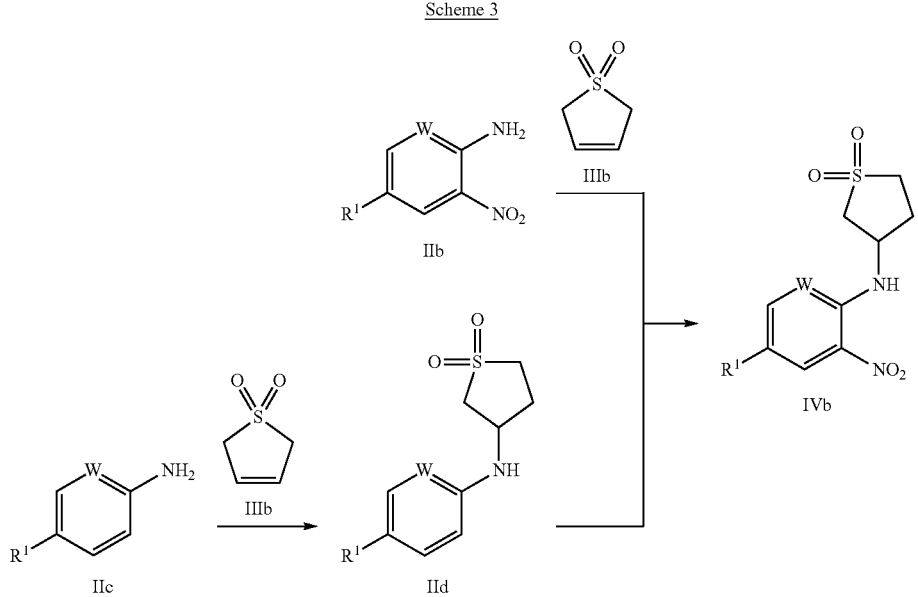

N-substituted aniline IId and o-nitro-N-substituted aniline IVb can be prepared by Michael addition of aniline IIc or IIb with 2,5-dihydro-thiophene 1,1-dioxide IIIb respectively. Michael addition can be carried out in the presence of a base such as cesium carbonate in an organic solvent such as acetonitrile at about 80° C. for several hours or overnight.

o-Nitro-N-substituted aniline IVb can also be prepared by nitrification of N-substituted aniline IId. The conversion can be achieved by treating IId with sulfuric acid and nitric acid at 0° C. for one to several hours.

This invention also relates to a process for the preparation of a compound of formula I comprising the reaction of
(a) a compound of formula (A)

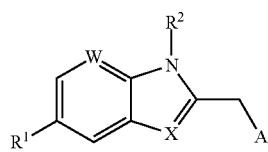

(A)

with

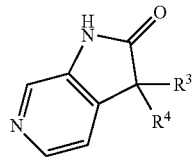

in the presence of a base;
(b) a compound of formula (B)

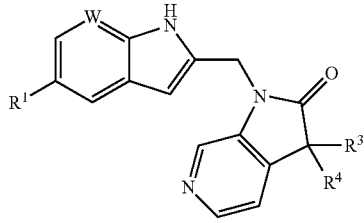

(B)

with Y—$R^2$ in the presence of a base;
wherein $R^1$ to $R^4$, W and X are defined above unless otherwise indicated; A is methanesulfonate or chloro; Y is trifluoromethanesulfonate or bromo.

In step (a), the base can be for example cesium carbonate, sodium hydride or sodium tert-butoxide;

In step (b), the base can be for example cesium carbonate.

A compound of formula I when manufactured according to the above process is also an object of the invention.

Pharmaceutical Compositions and Administration

The invention also relates to a compound of formula I for use as therapeutically active sub stance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit RSV fusion protein. For example, such amount may be below the amount that is toxic to normal cells, or the mammal as a whole.

In one example, the pharmaceutically effective amount of the compound of the invention administered parenterally per dose will be in the range of about 0.1 to about 50 mg/kg, alternatively about 0.1 to about 20 mg/kg of patient body weight per day, with the typical initial range of compound used being about 0.3 to about 15 mg/kg/day. In another embodiment, oral unit dosage forms, such as tablets and capsules, preferably contain from about 25 to about 100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg to about 500 mg of the compound of the invention compounded with about 90 to about 30 mg anhydrous lactose, about 5 to about 40 mg sodium croscarmellose, about 5 to about 30 mg polyvinylpyrrolidone (PVP) K30, and about 1 to about 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg), of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Indications and Methods of Treatment

The compounds of the invention can be utilized to inhibit RSV fusion protein, therefore prevent the virus cell syncytial function. Accordingly, the compounds of the invention are useful for the treatment or prophylaxis of RSV infection.

The invention relates to the use of a compound of formula I for the treatment or prophylaxis of respiratory syncytial virus infection.

The use of a compound of formula I for the preparation of medicaments useful in the treatment or prophylaxis diseases that are related to RSV infection is an object of the invention.

The invention relates in particular to the use of a compound of formula I for the preparation of a medicament for the treatment or prophylaxis of RSV infection.

Another embodiment includes a method of treating or preventing RSV infection in a mammal in need of such treatment, wherein the method comprises administering to said mammal a therapeutically effective amount of a compound of Formula I, a stereoisomer, tautomer, prodrug or pharmaceutically acceptable salt thereof.

Combination Therapy

The compounds of the invention can be used in combination with other antiviral ingredients for the treatment or prophylaxis of RSV infection.

EXAMPLES

The invention will be more fully understood by reference to the following examples. They should not, however, be construed as limiting the scope of the invention.

Abbreviations used herein are as follows:
μL: microliter
μm: micrometer
μM: micromoles per liter
AUC: area under the curve
$CD_3OD$: deuterated methanol
$CDCl_3$: deuterated chloroform
DMSO-$d_6$: deuterated dimethylsulfoxide
$EC_{50}$: the concentration of a compound where 50% of its maximal protection effect against viral induced CPE is observed
g: gram
HPLC: high performance liquid chromatography
Hz: Hertz
ICR: imprinting control region
J: coupling constants
LC/MS: Liquid chromatography/mass spectrometry
LongStrain: an A subtype RSV strain obtained from ATCC with catalog number VR-26
mg: milligram
MHz: megahertz
mL: milliliter
mm: millimeter
mmol: millimole
MS (ESI): mass spectroscopy (electron spray ionization)
NMR: nuclear magnetic resonance
obsd.: observed
Ph: phenyl
PK: Pharmacokinetics
SDPK: single dose pharmacokinetics
Prep HPLC: preparative high performance liquid chromatography
TEA: triethylamine
TLC: thin layer chromatography
δ: chemical shift
ppm: parts per million General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

LC/MS spectra were obtained using a MicroMass Plateform LC (Waters™ alliance 2795-ZQ2000). Standard LC/MS conditions were as follows (running time 6 minutes):

Acidic condition: A: 0.1% formic acid in $H_2O$; B: 0.1% formic acid in acetonitrile;
Basic condition: A: 0.01% $NH_3.H_2O$ in $H_2O$; B: acetonitrile;
Neutral condition: A: $H_2O$; B: acetonitrile.

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty.

NMR Spectra were obtained using Bruker Avance 400 MHz.

All reactions involving air-sensitive reagents were performed under an argon atmosphere. Reagents were used as received from commercial suppliers without further purification unless otherwise noted.

The following examples were prepared by the general methods outlined in the schemes above. They are intended to illustrate the meaning of the present invention but should by no means represent a limitation within the meaning of the present invention.

Preparative Examples

Example 1-1

1'-({5-Chloro-1-[cis-3-(methylsulfonyl)cyclobutyl]-1H-benzimidazol-2-yl}methyl)spiro[cyclopropane-1,3'-pyrrolo[2,3-c]pyridin]-2'(1'H)-one

Step 1: Preparation of 4-chloro-N-[cis-3-(methylsulfonyl)cyclobutyl]-2-nitroaniline

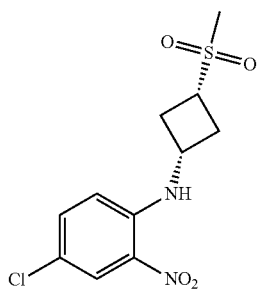 [SMILES: CS(=O)(=O)[C@H]1C[C@@H](Nc2ccc(Cl)cc2[N+](=O)[O-])C1]

A mixture of 4-chloro-1-fluoro-2-nitrobenzene (3.0 g, 17.1 mmol), cesium carbonate (3.25 g, 10.0 mmol) and cis-3-(methylsulfonyl)cyclobutanamine (1.5 g, 10.0 mmol, CAS No: 1363382-80-2) in acetonitrile (10 mL) was heated with stirring at 60° C. overnight. After being cooled to room temperature, the reaction mixture was filtered and the filtrate was concentrated in vacuo to afford 1.40 g of 4-chloro-N-[cis-3-(methylsulfonyl)cyclobutyl]-2-nitroaniline (yield was 45.9%).

Step 2: Preparation of 4-chloro-$N^1$-[cis-3-(methylsulfonyl)cyclobutyl]benzene-1,2-diamine

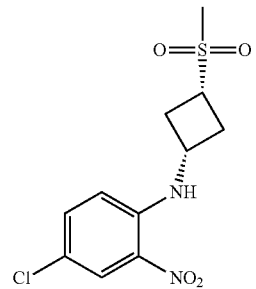 [SMILES: CS(=O)(=O)[C@H]1C[C@@H](Nc2ccc(Cl)cc2[N+](=O)[O-])C1]

A solution of 4-chloro-N-[cis-3-(methylsulfonyl)cyclobutyl]-2-nitroaniline (700 mg, 2.30 mmol) in methanol (20 mL) was stirred with Raney nickel (100 mg) under hydrogen atmosphere overnight. The resulting mixture was filtered and the filtrate was concentrated in vacuo to afford 300 mg of the crude 4-chloro-$N^1$-[cis-3-(methylsulfonyl)cyclobutyl] benzene-1,2-diamine (yield was 47.5%).

Step 3: Preparation of 5-chloro-2-(chloromethyl)-1-[cis-3-(methylsulfonyl)cyclobutyl]-1H-benzimidazole

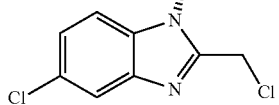

A mixture of 4-chloro-$N^1$-[cis-3-(methylsulfonyl)cyclobutyl]benzene-1,2-diamine (300 mg, 1.09 mmol) and 2-chloro-1,1,1-trimethoxyethane (900 mg, 5.82 mmol, CAS No. 74974-54-2) in ethanol (10 mL) was heated under reflux overnight. The reaction mixture was then cooled to room temperature and the precipitate was collected by filtration to afford 100 mg of 5-chloro-2-(chloromethyl)-1-[cis-3-(methylsulfonyl)cyclobutyl]-1H-benzimidazole (yield was 27.5%).

Step 4: Preparation of dimethyl 2-(3-nitro-4-pyridyl)propanedioate

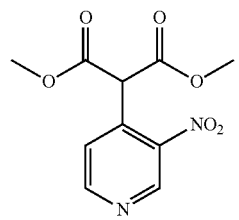

To a cooled suspension of sodium hydride (22.5 g, 0.56 mol) in dry toluene (1500 mL) was added dimethyl malonate (92 g, 0.7 mol) dropwise while stirring at a temperature between 0° C. and 10° C. under $N_2$. After the addition, the mixture was stirred for 30 minutes. Then to the resulting mixture was added a solution of 4-chloro-3-nitro-pyridine (75.0 g, 0.47 mmol, CAS No: 13091-23-1) in dry toluene (1000 mL) dropwise at room temperature and then the resulting mixture was heated under reflux overnight. After the reaction was completed, the mixture was cooled to room temperature and then poured into ice-water and then extracted with EtOAc (500 mL×3). The combined organic layers were dried over sodium sulphate and then concentrated in vacuo. The residue was purified by flash chromatography to afford 55 g of dimethyl 2-(3-nitro-4-pyridyl)propanedioate (yield was 38.6%).

Step 5: Preparation of methyl 2-(3-nitro-4-pyridyl)acetate

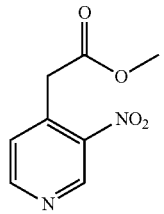

A mixture of dimethyl 2-(3-nitro-4-pyridyl)propanedioate (5.1 g, 20 mmol), lithium chloride (1.59 g, 37.6 mmol), water (0.36 g, 20 mmol) and dimethyl sulfoxide (100 mL) was heated at 100° C. for 8 hours. The reaction mixture was cooled, and then diluted with ethyl acetate (150 mL) and then washed successively with water (100 mL) and brine (100 mL). The combined aqueous layers were extracted with ethyl acetate (100 mL×2). The organic layer was combined, and then dried over sodium sulphate, then filtered and concentrated in vacuo. The residue was purified by flash chromatography to give 2.4 g of methyl 2-(3-nitro-4-pyridyl)acetate (yield was 61.2%).

Step 6: Preparation of methyl 2-(3-nitro-4-pyridyl)prop-2-enoate

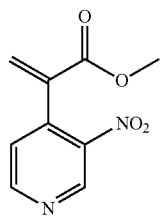

A mixture of methyl 2-(3-nitro-4-pyridyl)acetate (37 g, 0.189 mol), benzyl(triethyl)ammonium chloride (86 g, 1.233 mol) and potassium carbonate (53 g, 0.378 mol), in dry toluene (1500 mL) was degassed and then paraformaldehyde (37 g, 1.233 mol) was added in portions to the mixture. The reaction mixture was heated with stirring at 80° C. for 1 hour. The resulting mixture was cooled to room temperature and the solvent was removed. The residue was dissolved in ice-water (1000 mL), and then extracted with ethyl acetate (500 mL×2). The combined organic layer was washed with brine (500 mL), and then dried over sodium sulphate and then concentrated in vacuo. The residue was purified by flash column to afford 21.6 g of methyl 2-(3-nitro-4-pyridyl)prop-2-enoate as a brown solid (yield was 55%).

Step 7: Preparation of methyl 1-(3-nitro-4-pyridyl)cyclopropanecarboxylate

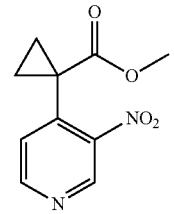 [SMILES: COC(=O)C1(c2ccncc2[N+](=O)[O-])CC1]

To a degassed solution of trimethyl sulfoxonium chloride (11.6 g, 0.072 mol, CAS No.: 47987-92-8) in dry tetrahydrofuran (200 mL) was added potassium tert-butoxide (5.9 g, 0.072 mol) at 0° C. The resulting mixture was stirred at room temperature for 1 hour. Then to the resulting mixture was added dropwise a solution of methyl 2-(3-nitro-4-pyridyl)prop-2-enoate (10 g, 0.048 mol) in dry tetrahydrofuran (200 mL). The reaction mixture was stirred at room temperature for 5 hours, and then poured into ice-water, then extracted with ethyl acetate (500 mL×2). The combined organic layer was washed with brine (500 mL), and then dried over sodium sulphate and then concentrated in vacuo. The residue was purified by flash chromatography to afford 3.5 g of methyl 1-(3-nitro-4-pyridyl)cyclopropanecarboxylate as a brown solid (yield was 33%).

Step 8: Preparation of methyl 1-(3-amino-4-pyridyl)cyclopropanecarboxylate

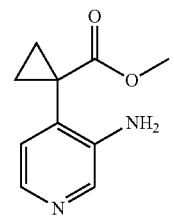

A solution of methyl 1-(3-nitro-4-pyridyl)cyclopropanecarboxylate (3.5 g, 15.7 mmol) in 200 mL of ethanol was stirred under hydrogen (50 psi) at room temperature for 6 hours in the presence of 10% palladium on carbon (350 mg). The resulting mixture was filtered and the filtrate was concentrated in vacuo to afford 2.9 g of methyl 1-(3-amino-4-pyridyl)cyclopropanecarboxylate (yield was 96%), which was used for the next step reaction without further purification.

Step 9: Preparation of spiro[cyclopropane-1,3'-pyrrolo[2,3-c]pyridin]-2'(1'H)-one

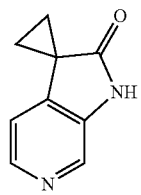 [SMILES: O=C1Nc2cnccc2C12CC2]

To a solution of methyl 1-(3-amino-4-pyridyl)cyclopropanecarboxylate (2.9 g, 15 mmol) in 100 mL of water was added tetrafluoroboric acid (6.6 mL, 50 wt % in water). The mixture was heated under reflux for 30 minutes and then cooled to room temperature. The mixture was then adjusted to pH 8 by addition of sodium bicarbonate, and then extracted with ethyl acetate (100 mL×5). The combined organic layer was dried over sodium sulphate and then concentrated in vacuo to afford 0.6 g of spiro[cyclopropane-1,3'-pyrrolo[2,3-c]pyridin]-2'(1'H)-one (yield was 25%).

Step 10: Preparation of 1'-({5-chloro-1-[cis-3-(methylsulfonyl)cyclobutyl]-1H-benzimidazol-2-yl}methyl)spiro[cyclopropane-1,3'-pyrrolo[2,3-c]pyridin]-2'(1'H)-one A mixture of spiro[cyclopropane-1,3'-pyrrolo[2,3-c]pyridin]-2'(1'H)-one (48 mg, 0.30 mmol) and sodium tert-butoxide (30 mg, 0.32 mmol) was stirred in N,N-dimethylformamide (4 mL) at room temperature for 30 minutes. Then the mixture was added to a cooled solution of 5-chloro-2-(chloromethyl)-1-[cis-3-(methylsulfonyl)cyclobutyl]-1H-benzimidazole (100 mg, 0.30 mmol) in N,N-dimethylformamide (6 mL) dropwise over 3 minutes at 0° C. The reaction mixture was stirred for about 5 minutes and then purified by preparative HPLC to afford 10.5 mg of the title product.

Example 1-2

1'-({5-Chloro-1-[trans-3-(methylsulfonyl)cyclobutyl]-1H-benzimidazol-2-yl}methyl)spiro[cyclopropane-1,3'-pyrrolo[2,3-c]pyridin]-2'(1'H)-one The title compound was prepared in analogy to Example 1-1 by using trans-3-(methylsulfonyl)cyclobutanamine (CAS No.: 1363381-54-7) instead of cis-3-(methylsulfonyl)cyclobutanamine.

Example 2-1

1'-{[5-Chloro-1-(2,2-dioxido-2-thiaspiro[3.3]hept-6-yl)-1H-benzimidazol-2-yl]methyl}spiro[cyclopropane-1,3'-pyrrolo[2,3-c]pyridin]-2'(1'H)-one Step 1: Preparation of dipropan-2-yl 3-hydroxycyclobutane-1,1-dicarboxylate

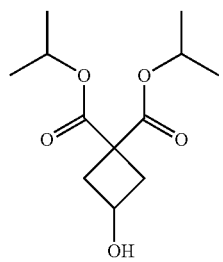 [SMILES: CC(C)OC(=O)C1(C(=O)OC(C)C)CC(O)C1]

A solution of dipropan-2-yl 3-(benzyloxy)cyclobutane-1,1-dicarboxylate (10.3 g, 30 mmol, CAS No.: 869109-30-8) in ethanol (100 mL) was shaken with palladium (II) hydroxide on carbon (2.0 g, 20% on carbon) under 50 psi of hydrogen at room temperature for 2 hours. The resulting mixture was filtered and the filtrate was concentrated in vacuo to afford dipropan-2-yl 3-hydroxycyclobutane-1,1-dicarboxylate as viscous oil which was used directly into next step.

Step 2: Preparation of dipropan-2-yl 3-oxocyclobutane-1,1-dicarboxylate

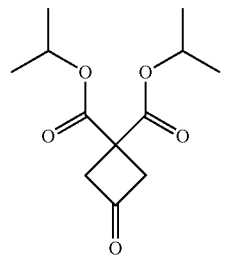 [SMILES: CC(C)OC(=O)C1(C(=O)OC(C)C)CC(=O)C1]

To a cooled solution of dipropan-2-yl 3-hydroxycyclobutane-1,1-dicarboxylate in dichloromethane (100 mL) in an ice-water bath was added 1,1,1-triacetoxy-1,1-dihydro-1,2-benziodoxol-3(1H)-one (Dess-Martin periodinane, 12.7 g, 30.0 mmol). The mixture was then warmed naturally to room temperature and stirred at room temperature for 2 hours. The reaction was quenched by addition of a saturated aqueous solution of disodium dithionite (20 mL). After being stirred at room temperature for 20 minutes, a saturated aqueous solution of sodium bicarbonate (100 mL) was added to the mixture. The separated aqueous layer was extracted with dichloromethane (150 mL×2). The combined organic layer was dried over sodium sulfate and then concentrated in vacuo to afford 7.5 g of dipropan-2-yl 3-oxocyclobutane-1,1-dicarboxylate as viscous oil.

Step 3: Preparation of dipropan-2-yl 3-(hydroxyimino)cyclobutane-1,1-dicarboxylate

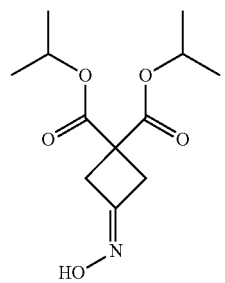 [SMILES: CC(C)OC(=O)C1(C(=O)OC(C)C)CC(=NO)C1]

A mixture of crude dipropan-2-yl 3-oxocyclobutane-1,1-dicarboxylate (4.56 g, about 18.8 mmol) and hydroxylamine hydrochloride (3.27 g, 47.0 mmol) in pyridine was stirred at 35° C. for 2 hours. The resulting mixture was concentrated in vacuo to remove the organic solvent. The residue was dissolved in diethyl ether (50 mL) and the solution was washed with water (50 mL×2), and then dried over sodium sulfate and then concentrated in vacuo to afford the crude dipropan-2-yl 3-(hydroxyimino)cyclobutane-1,1-dicarboxylate, which was used directly into next step without any purification.

Step 4: Preparation of dipropan-2-yl 3-aminocyclobutane-1,1-dicarboxylate

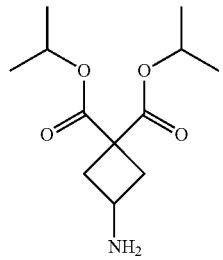

A solution of crude dipropan-2-yl 3-(hydroxyimino)cyclobutane-1,1-dicarboxylate in ethanol (150 mL) was stirred with palladium (II) hydroxide on carbon (640 mg, 20% on carbon) under hydrogen atmosphere at room temperature for 64 hours. The resulting mixture was concentrated in vacuo after filtration to afford 4.7 g of the crude dipropan-2-yl 3-aminocyclobutane-1,1-dicarboxylate as viscous oil.

Step 5: Preparation of dipropan-2-yl 3-{[(benzyloxy)carbonyl]amino}cyclobutane-1,1-dicarboxylate

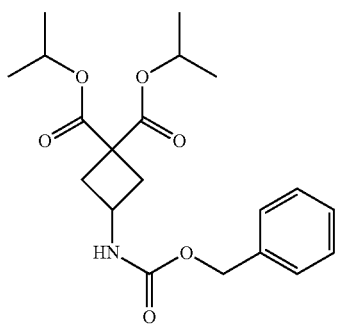 [SMILES: CC(C)OC(=O)C1(C(=O)OC(C)C)CC(NC(=O)OCc2ccccc2)C1]

A mixture of crude dipropan-2-yl 3-aminocyclobutane-1,1-dicarboxylate (4.7 g), benzyl carbonochloridate (2.82 mL, 20.0 mmol) and triethylamine (4.82 mL, 35 mmol) in dichloromethane (40 mL) was stirred at room temperature overnight. The resulting mixture was washed with a saturated aqueous solution of sodium bicarbonate (40 mL×2) and brine (40 mL). The organic layer was dried over sodium sulfate and then concentrated in vacuo. The residue was purified by flash column to afford 1.25 g of dipropan-2-yl 3-{[(benzyloxy)carbonyl]amino}cyclobutane-1,1-dicarboxylate as light viscous oil (yield of three steps was 17.6%).

Step 6: Preparation of benzyl [3,3-bis(hydroxymethyl)cyclobutyl]carbamate

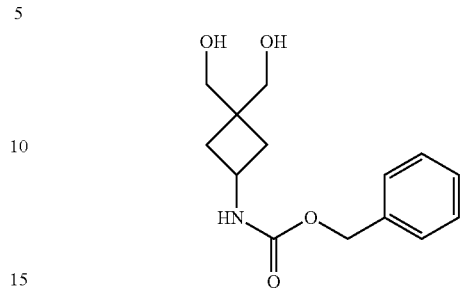

To a cooled solution of lithium aluminium hydride in tetrahydrofuran (1 M, 3.5 mL) was added a solution of dipropan-2-yl 3-{[(benzyloxy)carbonyl]amino}cyclobutane-1,1-dicarboxylate (1.25 g, 3.3 mmol) in anhydrous tetrahydrofuran (10 mL) dropwise in an ice-water bath. The resulting mixture was stirred at 0° C. for 1 hour and the reaction was quenched by addition of water (1 mL). After being stirred for 30 minutes, the mixture was filtered and the filtrate was concentrated in vacuo. The residue was dissolved in dichloromethane (50 mL) and then washed with brine (50 mL). The separated aqueous layer was extracted with dichloromethane (50 mL). The combined organic layer was dried over sodium sulfate and then concentrated in vacuo to afford the crude benzyl [3,3-bis(hydroxymethyl)cyclobutyl]carbamate.

Step 7: Preparation of (3-{[(benzyloxy)carbonyl]amino}cyclobutane-1,1-diyl)dimethanediyl dimethanesulfonate

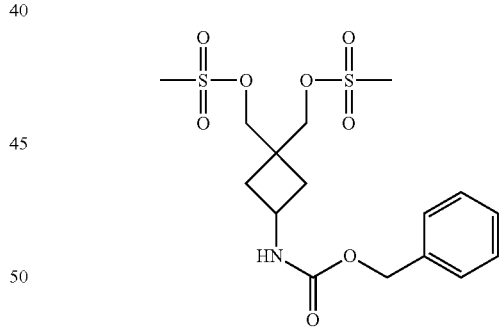

To a cooled solution of benzyl [3,3-bis(hydroxymethyl)cyclobutyl]carbamate in dichloromethane (20 mL) was added triethylamine (2.05 mL, 14.7 mmol) and methanesulfonyl chloride (0.63 mL, 8.3 mmol) at 0° C. After being stirred at 0° C. for 1 hour, the resulting mixture was washed with a saturated aqueous solution of sodium bicarbonate (30 mL). The aqueous layer was extracted with dichloromethane (30 mL×2). The combined organic layer was washed with saturated aqueous solution of sodium bicarbonate (50 mL) and brine (50 mL), and then dried over sodium sulfate and then concentrated in vacuo. The residue was used directly into next step without any purification.

Step 8: Preparation of benzyl 2-thiaspiro[3.3]hept-6-ylcarbamate

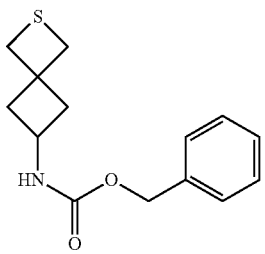 [SMILES: O=C(NC1CC2(CSC2)C1)OCc1ccccc1]

A solution of (3-{[(benzyloxy)carbonyl]amino}cyclobutane-1,1-diyl)dimethanediyl dimethanesulfonate in ethanol (6 mL) was heated with sodium sulfide nonahydrate (792 mg, 3.3 mmol) at 60° C. for 2 hours. The cooled reaction mixture was concentrated in vacuo. The residue was stirred with water (10 mL), and then extracted with diethyl ether (15 mL×2). The combined organic layer was washed with brine (25 mL), and then dried over sodium sulfate and then concentrated in vacuo. The residue was used directly into next step without any purification.

Step 9: Preparation of benzyl (2,2-dioxido-2-thiaspiro[3.3]hept-6-yl)carbamate

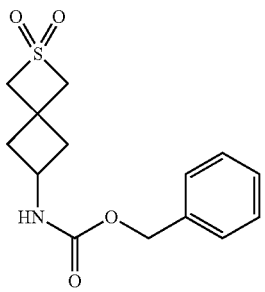 [SMILES: O=C(NC1CC2(C1)CS(=O)(=O)C2)OCc1ccccc1]

To a cooled solution of potassium peroxysulfate (3.69 g, 6.0 mmol) in water (5 mL) was added a solution of benzyl 2-thiaspiro[3.3]hept-6-ylcarbamate in methanol (10 mL) dropwise at 0° C. The resulting mixture was stirred in an ice-water bath for 3 hours. The resulting mixture was concentrated in vacuo to remove methanol. The aqueous layer was extracted with dichloromethane (20 mL×2). The combined organic layer was dried over sodium sulfate and then concentrated in vacuo. The residue was purified by flash column (eluting with 0-50% ethyl acetate in petroleum ether) to afford 380 mg of benzyl (2,2-dioxido-2-thiaspiro[3.3]hept-6-yl)carbamate (yield of 4 steps was 39.0%).

Step 10: Preparation of 2-thiaspiro[3.3]heptan-6-amine 2,2-dioxide

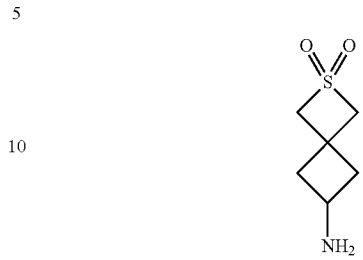

To a cooled solution of benzyl (2,2-dioxido-2-thiaspiro[3.3]hept-6-yl)carbamate (380 mg, 1.29 mmol) in dichloromethane (3.0 mL) at −10° C. was added 1M of boron trichloride solution in 1,4-dimethylbenzene (3.0 mL, 3.0 mmol) dropwise. The resulting mixture was stirred at −10° C. for 1 hour, then warmed naturally to room temperature and stirred at room temperature for 3 hours. The reaction was quenched by addition of brine (20 mL). The resulting mixture was extracted with dichloromethane (30 mL×3). The combined organic layer was dried over sodium sulfate and then concentrated in vacuo. The residue was used directly into next step without any purification.

Step 11: Preparation of N-(4-chloro-2-nitrophenyl)-2-thiaspiro[3.3]heptan-6-amine 2,2-dioxide

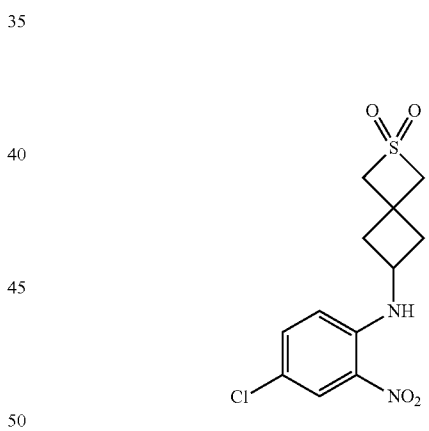

A mixture of 2-thiaspiro[3.3]heptan-6-amine 2,2-dioxide, 4-chloro-1-fluoro-2-nitrobenzene (525 mg, 3.0 mmol), potassium carbonate (828 mg, 6.0 mmol) and triethylamine (0.83 mL, 6.0 mmol) in N,N-dimethylformamide (10 mL) was heated at 120° C. for 4 hours. The resulting mixture was diluted with water (20 mL) and then extracted with ethyl acetate (25 mL×3). The combined organic layer was washed with brine (30 mL×2), and then dried over sodium sulfate and then concentrated in vacuo. The residue was purified by flash chromatography on silica gel (eluting with 0-8% methanol in dichloromethane) to afford 80.0 mg of N-(4-chloro-2-nitrophenyl)-2-thiaspiro[3.3]heptan-6-amine 2,2-dioxide as an orange solid (yield of 2 steps was 19.6%).

Step 12: Preparation of 4-chloro-N¹-(2,2-dioxido-2-thiaspiro[3.3]hept-6-yl)benzene-1,2-diamine

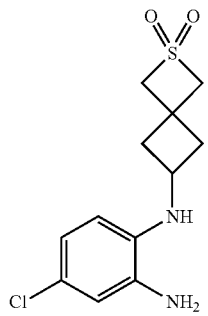 [SMILES: Nc1cc(Cl)ccc1NC1CC2(C1)CS(=O)(=O)C2]

A mixture of N-(4-chloro-2-nitrophenyl)-2-thiaspiro[3.3]heptan-6-amine 2,2-dioxide (80 mg, 0.25 mmol), Raney nickel (200 mg of suspension in water) and hydrazine hydrate (0.20 mL, 85% aqueous solution) in ethanol (20 mL) was stirred at room temperature overnight. The resulting mixture was filtered and the filtrate was concentrated in vacuo. The residue was dissolved in dichloromethane (20 mL) and the solution was washed with brine (15 mL). The organic layer was dried over sodium sulfate and then concentrated in vacuo to afford a semisolid, which was used directly into next step without any purification.

Step 13: Preparation of 5-cloro-2-(chloromethyl)-1-(2,2-dioxido-2-thiaspiro[3.3]hept-6-yl)-1H-benzimidazole

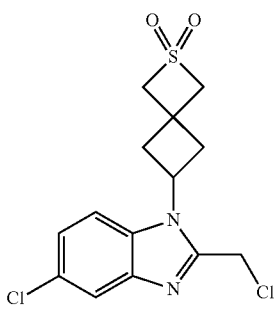 [SMILES: O=S1(=O)CC2(CC(n3c(CCl)nc4cc(Cl)ccc43)C2)C1]

A mixture of 4-cloro-N¹-(2,2-dioxido-2-thiaspiro[3.3]hept-6-yl)benzene-1,2-diamine and 2-chloro-1,1,1-triethoxyethane (1.5 mL) was heated at 120° C. for 1 hour under microwave irradiation. The resulting mixture was concentrated in vacuo and the residue was stirred with petroleum ether (40 mL). The precipitate was collected by filtration to afford 50.0 mg of a brown solid.

Step 14: Preparation of 1'-{[5-chloro-1-(2,2-dioxido-2-thiaspiro[3.3]hept-6-yl)-1H-benzimidazol-2-yl]methyl}spiro[cyclopropane-1,3'-pyrrolo[2,3-c]pyridin]-2'(1'H)-one A mixture 5-cloro-2-(chloromethyl)-1-(2,2-dioxido-2-thiaspiro[3.3]hept-6-yl)-1H-benzimidazole (50.0 mg, 0.145 mmol), spiro[cyclopropane-1,3'-pyrrolo[2,3-c]pyridin]-2'(1'H)-one (24 mg, 0.150 mmol) and cesium carbonate (81.0 mg, 0.250 mmol) in acetonitrile (4 mL) was stirred at room temperature for 4 hours. The resulting mixture was purified by preparative HPLC to afford 6.3 mg of the title product as a white solid.

Example 2-2

1'-{[5-Chloro-1-(1,1-dioxidotetrahydro-2H-thiopyran-4-yl)-1H-benzimidazol-2-yl]methyl}spiro[cyclopropane-1,3'-pyrrolo[2,3-c]pyridin]-2'(1'H)-one The title compound was prepared in analogy to Example 2-1 by using tetrahydro-2H-thiopyran-4-amine 1,1-dioxide (CAS No.: 210240-20-3) instead of 2-thiaspiro[3.3]heptan-6-amine 2,2-dioxide.

Example 2-3

1'-[(5-Chloro-1-cyclopentyl-1H-benzimidazol-2-yl)methyl]spiro[cyclopropane-1,3'-pyrrolo[2,3-c]pyridin]-2'(1'H)-one The title compound was prepared in analogy to Example 2-1 by using cyclopentanamine (CAS No.: 1003-03-8) instead of 2-thiaspiro[3.3]heptan-6-amine 2,2-dioxide.

Example 2-4

1'-{[5-Chloro-1-(oxetan-3-yl)-1H-benzimidazol-2-yl]methyl}spiro[cyclopropane-1,3'-pyrrolo[2,3-c]pyridin]-2'(1'H)-one The title compound was prepared in analogy to Example 2-1 by using oxetan-3-amine (CAS No.: 21635-88-1) instead of 2-thiaspiro[3.3]heptan-6-amine 2,2-dioxide.

Example 2-5

1'-{[5-Chloro-1-(3,3-difluorocyclobutyl)-1H-benzimidazol-2-yl]methyl}spiro[cyclopropane-1,3'-pyrrolo[2,3-c]pyridin]-2'(1'H)-one The title compound was prepared in analogy to Example 2-1 by using 3,3-difluorocyclobutanamine (CAS No.: 637031-93-7) instead of 2-thiaspiro[3.3]heptan-6-amine 2,2-dioxide.

Example 2-6

1'-{[5-Chloro-1-(tetrahydro-2H-pyran-4-yl)-1H-benzimidazol-2-yl]methyl}spiro[cyclopropane-1,3'-pyrrolo[2,3-c]pyridin]-2'(1'H)-one The title compound was prepared in analogy to Example 2-1 by using tetrahydro-2H-pyran-4-amine (CAS No.: 38041-19-9) instead of 2-thiaspiro[3.3]heptan-6-amine 2,2-dioxide.

Example 2-7

1'-{[5-Chloro-1-(4-hydroxycyclohexyl)-1H-benzimidazol-2-yl]methyl}spiro[cyclopropane-1,3'-pyrrolo[2,3-c]pyridin]-2'(1'H)-one The title compound was prepared in analogy to Example 2-1 by using 4-aminocyclohexanol (CAS No.: 6850-65-3) instead of 2-thiaspiro[3.3]heptan-6-amine 2,2-dioxide.

Example 2-8

1'-{[5-Chloro-1-(3-hydroxycyclopentyl)-1H-benzimidazol-2-yl]methyl}spiro[cyclopropane-1,3'-pyrrolo[2,3-c]pyridin]-2'(1'H)-one The title compound was prepared in analogy to Example 2-1 by using 3-aminocyclopentanol (CAS No.: 13725-38-7) instead of 2-thiaspiro[3.3]heptan-6-amine 2,2-dioxide.

Example 2-9

1'-{[5-Chloro-1-(2-oxopyrrolidin-3-yl)-1H-benzimidazol-2-yl]methyl}spiro[cyclopropane-1,3'-pyrrolo[2,3-c]pyridin]-2'(1'H)-one The title compound was prepared in analogy to Example 2-1 by using 3-aminopyrrolidin-2-one (CAS No.: 2483-65-0) instead of 2-thiaspiro[3.3]heptan-6-amine 2,2-dioxide.

Example 2-10

1'-{[5-Chloro-1-(2-oxopiperidin-4-yl)-1H-benzimidazol-2-yl]methyl}spiro[cyclopropane-1,3'-pyrrolo[2,3-c]pyridin]-2'(1'H)-one The title compound was prepared in analogy to Example 2-1 by using 4-aminopiperidin-2-one (CAS No.: 5513-66-6) instead of 2-thiaspiro[3.3]heptan-6-amine 2,2-dioxide.

Example 2-11

1'-{[5-Chloro-1-(3,3-difluorocyclopentyl)-1H-benzimidazol-2-yl]methyl}spiro[cyclopropane-1,3'-pyrrolo[2,3-c]pyridin]-2'(1'H)-one The title compound was prepared in analogy to Example 2-1 by using 3,3-difluorocyclopentanamine (CAS No.: 939525-61-8) instead of 2-thiaspiro[3.3]heptan-6-amine 2,2-dioxide.

Example 2-12 cis-4-{5-Chloro-2-[(2'-oxospiro[cyclopropane-1,3'-pyrrolo[2,3-c]pyridin]-1'(2'H)-yl)methyl]-1H-benzimidazol-1-yl}cyclohexanecarboxylic acid The title compound was prepared in analogy to Example 2-1 by using cis-4-aminocyclohexanecarboxylic acid (CAS No.: 3685-23-2) instead of 2-thiaspiro[3.3]heptan-6-amine 2,2-dioxide.

Example 2-13

1'-{[6-Chloro-3-(1,1-dioxidotetrahydrothiophen-3-yl)-3H-imidazo[4,5-b]pyridin-2-yl]methyl}spiro[cyclopropane-1,3'-pyrrolo[2,3-c]pyridin]-2'(1'H)-one The title compound was prepared in analogy to Example 2-1 by using tetrahydrothiophen-3-amine 1,1-dioxide (CAS No.: 6338-70-1) instead of 2-thiaspiro[3.3]heptan-6-amine 2,2-dioxide.

Example 2-14

1'-{[5-Chloro-1-(tetrahydrofuran-3-yl)-1H-benzimidazol-2-yl]methyl}spiro[cyclopropane-1,3'-pyrrolo[2,3-c]pyridin]-2'(1'H)-one The title compound was prepared in analogy to Example 2-1 by using tetrahydrofuran-3-amine (CAS No.: 88675-24-5) instead of 2-thiaspiro[3.3]heptan-6-amine 2,2-dioxide.

Example 2-15 tert-Butyl 3-{5-chloro-2-[(2'-oxospiro[cyclopropane-1,3'-pyrrolo[2,3-c]pyridin]-1'(2'H)-yl)methyl]-1H-benzimidazol-1-yl}pyrrolidine-1-carboxylate The title compound was prepared in analogy to Example 2-1 by using tert-butyl 3-aminopyrrolidine-1-carboxylate (CAS No.: 186550-13-0) instead of 2-thiaspiro[3.3]heptan-6-amine 2,2-dioxide.

Example 2-16

1'-{[5-Chloro-1-(1,3-dihydroxypropan-2-yl)-1H-benzimidazol-2-yl]methyl}spiro[cyclopropane-1,3'-pyrrolo[2,3-c]pyridin]-2'(1'H)-one The title compound was prepared in analogy to Example 2-1 by using 2-aminopropane-1,3-diol (CAS No.: 534-03-2) instead of 2-thiaspiro[3.3]heptan-6-amine 2,2-dioxide.

Example 2-17

1'-{[5-Chloro-1-(trans-3-hydroxy-3-methylcyclobutyl)-1H-benzimidazol-2-yl]methyl}spiro[cyclopropane-1,3'-pyrrolo[2,3-c]pyridin]-2'(1'H)-one The title compound was prepared in analogy to Example 2-1 by using trans-3-amino-1-methylcyclobutanol (CAS No.: 1363381-26-3) instead of 2-thiaspiro[3.3]heptan-6-amine 2,2-dioxide.

Example 3-1

1'-{[5-Chloro-1-(1,1-dioxidotetrahydrothiophen-3-yl)-1H-benzimidazol-2-yl]methyl}spiro[cyclopropane-1,3'-pyrrolo[2,3-c]pyridin]-2'(1'H)-one Step 1: Preparation of N-(4-chloro-2-nitrophenyl)tetrahydrothiophen-3-amine 1,1-dioxide

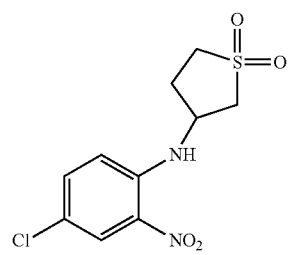 [SMILES: O=[N+]([O-])c1cc(Cl)ccc1NC1CCS(=O)(=O)C1]

A mixture of 4-chloro-2-nitroaniline (1.72 g, 10.0 mmol, CAS No.: 89-63-4), 2,5-dihydrothiophene 1,1-dioxide (1.18 g, 10.0 mmol, CAS No.: 77-79-2) and cesium carbonate (6.50 g, 20.0 mmol) in N,N-dimethylformamide (50 mL) was heated with stirring at 80° C. for 16 hours. The resulting mixture was then poured into water and extracted with ethyl acetate. The organic layer was washed with brine, and then dried over sodium sulfate and concentrated in vacuo. The residue was purified by flash column (eluting with 25% ethyl acetate in petroleum ether) to afford N-(4-chloro-2-nitrophenyl)tetrahydrothiophen-3-amine 1,1-dioxide.

Step 2: Preparation of 1'-{[5-chloro-1-(1,1-dioxido-tetrahydrothiophen-3-yl)-1H-benzimidazol-2-yl]methyl}spiro[cyclopropane-1,3'-pyrrolo[2,3-c]pyridin]-2'(1'H)-one The title compound was prepared in analogy to Example 2-1 by using N-(4-chloro-2-nitrophenyl)tetrahydrothiophen-3-amine 1,1-dioxide instead of N-(4-chloro-2-nitrophenyl)-2-thiaspiro[3.3]heptan-6-amine 2,2-dioxide.

Example 3-2 and Example 3-3

1'-({5-Chloro-1-[(3S)-1,1-dioxidotetrahydrothiophen-3-yl]-1H-benzimidazol-2-yl}methyl)spiro[cyclopropane-1,3'-pyrrolo[2,3-c]pyridin]-2'(1'H)-one and 1'-({5-Chloro-1-[(3R)-1,1-dioxidotetrahydrothiophen-3-yl]-1H-benzimidazol-2-yl}methyl)spiro[cyclopropane-1,3'-pyrrolo[2,3-c]pyridin]-2'(1'H)-one The title compounds were prepared by chiral separation of 1'-{[5-chloro-1-(1,1-dioxidotetrahydrothiophen-3-yl)-1H-benzimidazol-2-yl]methyl}spiro[cyclopropane-1,3'-pyrrolo[2,3-c]pyridin]-2'(1'H)-one.

Example 4-1

1'-{[5-Chloro-1-(1,1-dioxidothietan-3-yl)-1H-benzimidazol-2-yl]methyl}spiro[cyclopropane-1,3'-pyrrolo[2,3-c]pyridin]-2'(1'H)-one Step 1: Preparation of N-(4-chloro-2-nitrophenyl)thietan-3-amine

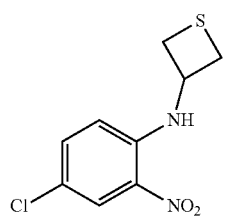 [SMILES: O=[N+]([O-])c1cc(Cl)ccc1NC1CSC1]

A mixture of 4-chloro-1-fluoro-2-nitrobenzene (2.55 g, 14.5 mmol, CAS No.: 345-18-6), thietan-3-amine (1.30 g, 14.5 mmol, CAS No.: 128861-76-7) and potassium carbonate (4.0 g, 29.0 mmol) in N,N-dimethylformamide (50 mL) was heated with stirring at 50° C. for 4 hours. After being cooled to room temperature, the reaction mixture was diluted with ethyl acetate (50 mL) and washed with water (50 mL). The organic layer was dried over sodium sulfate and concentrated in vacuo to afford 1.20 g of N-(4-chloro-2-nitrophenyl)thietan-3-amine as an orange powder.

Step 2: Preparation of N-(4-chloro-2-nitrophenyl)thietan-3-amine 1,1-dioxide

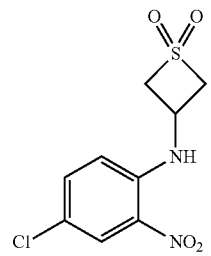 [SMILES: O=[N+]([O-])c1cc(Cl)ccc1NC1CS(=O)(=O)C1]

To the slurry of N-(4-chloro-2-nitrophenyl)thietan-3-amine (1.20 g, 4.90 mmol) in methanol (25 mL) was added a solution of oxone (6.03 g, 9.80 mmol) in water (25 mL) dropwise at a temperature between 10° C. and 15° C. After being stirred at room temperature overnight, the resulting mixture was diluted with dichloromethane (50 mL) and then washed with water (50 mL). The organic layer was dried over sodium sulfate and concentrated in vacuo. The precipitate was collected by filtration and then dried in vacuo to afford 1.2 g of N-(4-chloro-2-nitrophenyl)thietan-3-amine 1,1-dioxide as an orange powder.

Step 3: Preparation of 1'-{[5-chloro-1-(1,1-dioxidothietan-3-yl)-1H-benzimidazol-2-yl]methyl}spiro[cyclopropane-1,3'-pyrrolo[2,3-c]pyridin]-2'(1'H)-one The title compound was prepared in analogy to Example 2-1 by using N-(4-chloro-2-nitrophenyl)thietan-3-amine 1,1-dioxide instead of N-(4-chloro-2-nitrophenyl)-2-thiaspiro[3.3]heptan-6-amine 2,2-dioxide.

Example 4-2

1-{[5-Chloro-1-(1,1-dioxidothietan-3-yl)-1H-benzimidazol-2-yl]methyl}-3,3-dimethyl-1,3-dihydro-2H-pyrrolo[2,3-c]pyridin-2-one Step 1: Preparation of 3,3-dimethyl-1,3-dihydro-2H-pyrrolo[2,3-c]pyridin-2-one

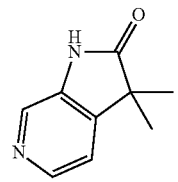

A mixture of ethyl 2-(3-bromopyridin-4-yl)-2-methylpropanoate (544 mg, 2.0 mmol, CAS No.: 1069115-10-1), 28% of ammonium hydroxide (5 mL), copper(I) oxide (14.6 mg, 0.10 mmol), N,N'-dimethylethane-1,2-diamine (0.20 mL) and potassium carbonate (56 mg, 0.40 mmol) in ethane-1,2-diol (2 mL) was heated at 120° C. for 2 hours under microwave irradiation and then heated at 120° C. in an oil bath overnight. The resulting mixture was concentrated in vacuo and the residue was purified by flash column to afford 200 mg of 3,3-dimethyl-1,3-dihydro-2H-pyrrolo[2,3-c]pyridin-2-one (yield was 61.7%).

Step 2: Preparation of 1-{[5-chloro-1-(1,1-dioxi-dothietan-3-yl)-1H-benzimidazol-2-yl]methyl}-3,3-dimethyl-1,3-dihydro-2H-pyrrolo[2,3-c]pyridin-2-one The title compound was prepared in analogy to Example 4-1 by using 3,3-dimethyl-1,3-dihydro-2H-pyrrolo[2,3-c]pyridin-2-one instead of spiro[cyclopropane-1,3'-pyrrolo[2,3-c]pyridin]-2'(1'H)-one.

Example 4-3

1-{[5-Chloro-1-(1,1-dioxidothietan-3-yl)-1H-benzimidazol-2-yl]methyl}-3,3-diethyl-1,3-dihydro-2H-pyrrolo[2,3-c]pyridin-2-one Step 1: Preparation of 3,3-diethyl-1,3-dihydro-2H-pyrrolo[2,3-c]pyridin-2-one

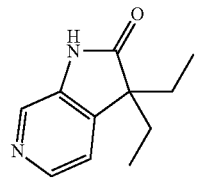

3,3-Diethyl-1,3-dihydro-2H-pyrrolo[2,3-c]pyridin-2-one was prepared in analogy to 3,3-dimethyl-1,3-dihydro-2H-pyrrolo[2,3-c]pyridin-2-one in Example 4-2 by using ethyl 2-(3-bromopyridin-4-yl)-2-ethylbutanoate instead of ethyl 2-(3-bromopyridin-4-yl)-2-methylpropanoate.

Step 2: Preparation of 1-{[5-Chloro-1-(1,1-dioxi-dothietan-3-yl)-1H-benzimidazol-2-yl]methyl}-3,3-diethyl-1,3-dihydro-2H-pyrrolo[2,3-c]pyridin-2-one The title compound was prepared in analogy to Example 4-1 by using 3,3-diethyl-1,3-dihydro-2H-pyrrolo[2,3-c]pyridin-2-one instead of spiro[cyclopropane-1,3'-pyrrolo[2,3-c]pyridin]-2'(1'H)-one.

Example 5

1'-{[5-Chloro-1-(1-oxidothietan-3-yl)-1H-benzimidazol-2-yl]methyl}spiro[cyclopropane-1,3'-pyrrolo[2,3-c]pyridin]-2'(1'H)-one Step 1: Preparation of N-(4-chloro-2-nitrophenyl)thietan-3-amine 1-oxide

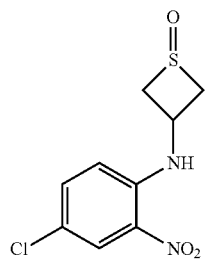 [SMILES: O=[N+]([O-])c1cc(Cl)ccc1NC1CS(=O)C1]

To a slurry of N-(4-chloro-2-nitrophenyl)thietan-3-amine (2.0 g, 8.2 mmol) in methanol (25 mL) was added a solution of oxone (5.0 g, 8.1 mmol) in water (25 mL) dropwise at a temperature between 10° C. and 15° C. After being stirred at room temperature overnight, the resulting mixture was diluted with dichloromethane (50 mL) and then washed with water (50 mL). The organic layer was dried over sodium sulfate and then concentrated in vacuo. The precipitate was collected by filtration and dried in vacuo to afford the crude N-(4-chloro-2-nitrophenyl)thietan-3-amine 1-oxide as an orange powder which was used for next step without purification.

Step 2: Preparation of 1'-{[5-chloro-1-(1-oxidothi-etan-3-yl)-1H-benzimidazol-2-yl]methyl}spiro[cy-clopropane-1,3'-pyrrolo[2,3-c]pyridin]-2'(1'H)-one The title compound was prepared in analogy to Example 4-1 by using N-(4-chloro-2-nitrophenyl)thietan-3-amine 1-oxide instead of N-(4-chloro-2-nitrophenyl)thietan-3-amine 1,1-dioxide.

Example 6

1'-{[5-Chloro-1-(1,1-dioxidothietan-3-yl)-7-fluoro-1H-benzimidazol-2-yl]methyl}spiro[cyclopropane-1,3'-pyrrolo[2,3-c]pyridin]-2'(1'H)-one Step 1: Preparation of N-(4-chloro-2-fluorophenyl)thietan-3-amine

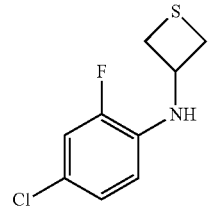 [SMILES: Fc1cc(Cl)ccc1NC1CSC1]

To a solution of 4-chloro-2-fluoroaniline (2.0 g, 13.7 mmol, CAS No.: 57946-56-2) in dichloromethane (20 mL) was added thietan-3-one (2.42 g, 27.4 mmol, CAS No.: 22131-92-6), sodium triacetoxyborohydride (5.8 g, 27.4 mmol) and acetic acid (2.47 g, 41.1 mmol). The resulting mixture was stirred at room temperature for 7 days. The reaction mixture was washed with saturated aqueous solution of sodium bicarbonate (20 mL). The organic layer was dried over sodium sulfate and then concentrated in vacuo. The residue was purified by column chromatography to give 500 mg of N-(4-chloro-2-fluorophenyl)thietan-3-amine.

Step 2: Preparation of N-(4-chloro-2-fluorophenyl)thietan-3-amine 1,1-dioxide

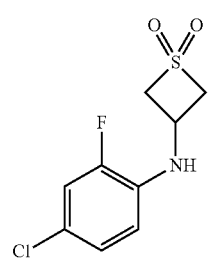 [SMILES: O=S1(=O)CC(Nc2ccc(Cl)cc2F)C1]

N-(4-Chloro-2-fluorophenyl)thietan-3-amine 1,1-dioxide was prepared in analogy to N-(4-chloro-2-nitrophenyl)thietan-3-amine 1,1-dioxide in Example 4-1 by using N-(4- chloro-2-fluorophenyl)thietan-3-amine instead of N-(4-chloro-2-nitrophenyl)thietan-3-amine.

Step 3: Preparation of N-(4-chloro-2-fluoro-6-nitrophenyl)thietan-3-amine 1,1-dioxide

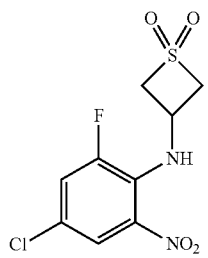 [SMILES: O=[N+]([O-])c1cc(Cl)cc(F)c1NC1CS(=O)(=O)C1]

To a mixture of N-(4-chloro-2-fluorophenyl)thietan-3-amine 1,1-dioxide (500 mg, 2.0 mmol) in conc. sulfuric acid (10 mL) was added nitric acid fuming (1 mL) at 0° C. slowly. The resulting mixture was stirred at 0° C. for one hour. The resulting reaction mixture was poured into ice-water (20 mL) and then extracted with ethyl acetate (20 mL). The organic layer was dried over sodium sulfate and then concentrated in vacuo to afford the crude N-(4-chloro-2-fluoro-6-nitrophenyl)thietan-3-amine 1,1-dioxide which was used for next step directly without purification.

Step 4: Preparation of 1'-{[5-Chloro-1-(1,1-dioxidothietan-3-yl)-7-fluoro-1H-benzimidazol-2-yl]methyl}spiro[cyclopropane-1,3'-pyrrolo[2,3-c]pyridin]-2'(1'H)-one The title compound was prepared in analogy to Example 4-1 by using N-(4-chloro-2-fluoro-6-nitrophenyl)thietan-3-amine 1,1-dioxide instead of N-(4-chloro-2-nitrophenyl)thietan-3-amine 1,1-dioxide.

Example 7-1

1'-{[5-Chloro-1-(6-oxopiperidin-3-yl)-1H-benzimidazol-2-yl]methyl}spiro[cyclopropane-1,3'-pyrrolo[2,3-c]pyridin]-2'(1'H)-one Step 1: Preparation of methyl (2E)-3-[(4-methoxybenzyl)amino]prop-2-enoate

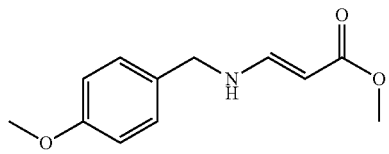

To a cooled solution of methyl prop-2-enoate (1.68 g, 21.0 mmol) in tert-butyl methyl ether (20 mL) at 0° C. was added (4-methoxyphenyl)methanamine (2.74 g, 20.0 mmol, CAS No.: 2393-23-9). The resulting mixture was then allowed to be warmed naturally to room temperature and stirred at room temperature for 12 hours. The resulting reaction mixture was concentrated in vacuo to afford the crude methyl (2E)-3-[(4-methoxybenzyl)amino]prop-2-enoate which was used directly into the next step.

Step 2: Preparation of methyl 1-(4-methoxybenzyl)-6-oxo-1,4,5,6-tetrahydropyridine-3-carboxylate

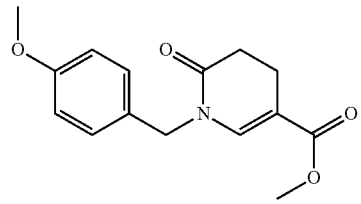 [SMILES: COC(=O)C1=CN(Cc2ccc(OC)cc2)C(=O)CC1]

To a solution of methyl (2E)-3-[(4-methoxybenzyl)amino]prop-2-enoate in tetrahydrofuran (1.0 L) was added acryloyl chloride (20.0 g, 221 mmol, CAS No.: 814-68-6). After being heated under reflux for 16 hours, the resulting mixture was concentrated in vacuo and the residue was purified by column (eluting with 50% ethyl acetate in petroleum ether) to afford 20.0 g of methyl 1-(4-methoxybenzyl)-6-oxo-1,4,5,6-tetrahydropyridine-3-carboxylate as a white solid (yield of two steps was 36.3%).

Step 3: Preparation of methyl 1-(4-methoxybenzyl)-6-oxopiperidine-3-carboxylate

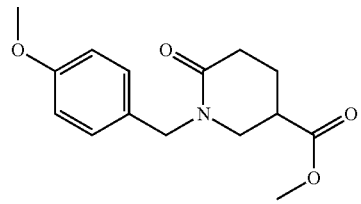 [SMILES: COC(=O)C1CCC(=O)N(Cc2ccc(OC)cc2)C1]

A solution of methyl 1-(4-methoxybenzyl)-6-oxo-1,4,5,6-tetrahydropyridine-3-carboxylate (20.0 g, 72.6 mmol) in ethanol (500 mL) was stirred with 10% palladium on carbon (5.0 g) under 50 psi of hydrogen at room temperature for 16 hours. The resulting mixture was filtered and the filtrate was concentrated in vacuo to afford 20.0 g of methyl 1-(4-methoxybenzyl)-6-oxopiperidine-3-carboxylate as colorless oil (yield was 99.3%).

Step 4: Preparation of 1-(4-methoxybenzyl)-6-oxopiperidine-3-carboxamide

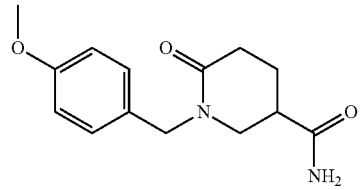 [SMILES: COc1ccc(CN2CC(C(N)=O)CCC2=O)cc1]

Ammonia gas was passed through a cooled solution of methyl 1-(4-methoxybenzyl)-6-oxopiperidine-3-carboxylate (5.40 g, 19.5 mmol) in methanol (300 mL) at −10° C. for 30 minutes. The resulting mixture was allowed to be warmed to room temperature and stirred at the temperature for 16 hours. The reaction mixture was concentrated in vacuo to afford 5.10 g of 1-(4-methoxybenzyl)-6-oxopiperidine-3-carboxamide as a white powder (yield was 99.7%).

Step 5: Preparation of 5-amino-1-(4-methoxybenzyl)piperidin-2-one

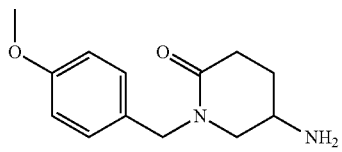 [SMILES: COc1ccc(CN2CC(N)CCC2=O)cc1]

To a solution of 1-(4-methoxybenzyl)-6-oxopiperidine-3-carboxamide (5.10 g, 19.5 mmol) in acetonitrile (50 mL) and water (50 mL) was added bis(acetyloxy)(phenyl)-λ³-iodane (8.17 g, 25.4 mmol, CAS No.: 3240-34-4). After being stirred at room temperature for 16 hours, the resulting mixture was acidified to pH1 by addition of 1N hydrochloric acid and then extracted with dichloromethane (200 mL×2). The aqueous layer was then basified by 10% aqueous solution of sodium hydroxide to pH10 and then extracted with dichloromethane (200 mL×2). The combined organic layer was dried over sodium sulfate and then concentrated in vacuo to afford 3.5 g of 5-amino-1-(4-methoxybenzyl)piperidin-2-one as colorless oil (yield was 76.6%).

Step 6: Preparation of 5-[(4-chloro-2-nitrophenyl)amino]-1-(4-methoxybenzyl)piperidin-2-one

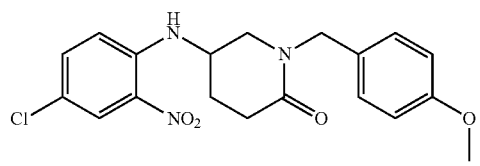 [SMILES: COc1ccc(CN2CC(Nc3ccc(Cl)cc3[N+](=O)[O-])CCC2=O)cc1]

A mixture of 5-amino-1-(4-methoxybenzyl)piperidin-2-one (600 mg, 2.56 mmol), 4-chloro-1-fluoro-2-nitrobenzene (450 mg, 2.56 mmol) and potassium carbonate (710 mg, 5.12 mmol) in acetonitrile (50 mL) was stirred at room temperature for 72 hours. The resulting mixture was concentrated in vacuo and the residue was purified by silica column (eluting with ethyl acetate) to afford 400 mg of 5-[(4-chloro-2-nitrophenyl)amino]-1-(4-methoxybenzyl)piperidin-2-one as a powder (yield was 40.1%).

Step 7: Preparation of 5-[5-chloro-2-(chloromethyl)-1H-benzimidazol-1-yl]-1-(4-methoxybenzyl)piperidin-2-one

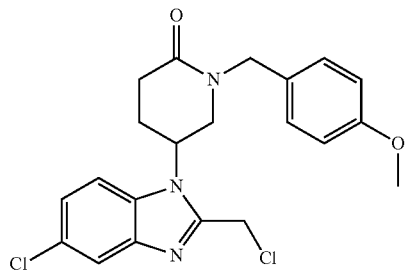 [SMILES: COc1ccc(CN2CC(n3c(CCl)nc4cc(Cl)ccc43)CCC2=O)cc1]

5-[5-Chloro-2-(chloromethyl)-1H-benzimidazol-1-yl]-1-(4-methoxybenzyl)piperidin-2-one was prepared in analogy to 5-chloro-2-(chloromethyl)-1-[cis-3-(methylsulfonyl)cyclobutyl]-1H-benzimidazole in Example 1 by using 5-[(4-chloro-2-nitrophenyl)amino]-1-(4-methoxybenzyl)piperidin-2-one instead of 4-chloro-N-[cis-3-(methylsulfonyl)cyclobutyl]-2-nitroaniline.

Step 8: Preparation of 1'-({5-chloro-1-[1-(4-methoxybenzyl)-6-oxopiperidin-3-yl]-1H-benzimidazol-2-yl}methyl)spiro[cyclopropane-1,3'-pyrrolo[2,3-c]pyridin]-2'(1'H)-one

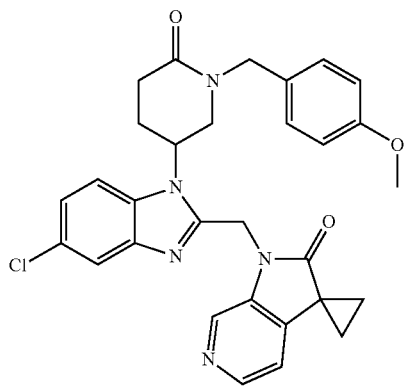 [SMILES: COc1ccc(CN2CC(n3c(CN4C(=O)C5(CC5)c5ccncc54)nc4cc(Cl)ccc43)CCC2=O)cc1]

A mixture of 5-[5-chloro-2-(chloromethyl)-1H-benzimidazol-1-yl]-1-(4-methoxybenzyl)piperidin-2-one (418 mg, 1.00 mmol), spiro[cyclopropane-1,3'-pyrrolo[2,3-c]pyridin]-2'(1'H)-one (192 mg, 1.20 mmol) and cesium carbonate (390 mg, 1.20 mmol) in N,N-dimethylformamide (20 mL) was stirred at room temperature for 16 hours. The resulting mixture was concentrated and the residue was purified by silica column (eluting with 5% methanol in ethyl acetate) to afford 300 mg of 1'-({5-chloro-1-[1-(4-methoxybenzyl)-6-oxopiperidin-3-yl]-1H-benzimidazol-2-yl}methyl)spiro[cyclopropane-1,3'-pyrrolo[2,3-c]pyridin]-2'(1'H)-one (yield was 55.3%).

Step 9: Preparation of 1'-{[5-chloro-1-(6-oxopiperidin-3-yl)-1H-benzimidazol-2-yl]methyl}spiro[cyclopropane-1,3'-pyrrolo[2,3-c]pyridin]-2'(1'H)-one To a cooled solution of 1'-({5-chloro-1-[1-(4-methoxybenzyl)-6-oxopiperidin-3-yl]-1H-benzimidazol-2-yl}methyl)spiro[cyclopropane-1,3'-pyrrolo[2,3-c]pyridin]-2'(1'H)-one (270 mg, 0.498 mmol) in acetonitrile (5 mL) was added a solution of diammonium cerium(IV) nitrate (820 mg, 1.50 mmol) in water (5 mL) dropwise at 0° C. After being stirred at room temperature for 16 hours, the resulting mixture was concentrated in vacuo. The residue was purified by preparative HPLC to afford 10 mg of the title product.

Example 7-2

1'-{[5-Chloro-1-(5-oxopyrrolidin-3-yl)-1H-benzimidazol-2-yl]methyl}spiro[cyclopropane-1,3'-pyrrolo[2,3-c]pyridin]-2'(1'H)-one Step 1: Preparation of methyl 1-(4-methoxybenzyl)-5-oxopyrrolidine-3-carboxylate

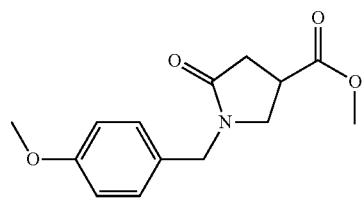

A mixture of dimethyl 2-methylidenebutanedioate (47.5 g, 300 mmol, CAS No.: 617-52-7) and 1-(4-methoxyphenyl)methanamine (41.2 g, 300 mmol) in methanol (400 mL) was stirred at room temperature overnight. The resulting reaction mixture was concentrated in vacuo to remove methanol. The residual brown oil was stirred with ethyl acetate (40 mL) and hexane (400 mL) vigorously. The white precipitate was collected by filtration and washed with hexane (40 mL×2) to afford 68.0 g of methyl 1-(4-methoxybenzyl)-5-oxopyrrolidine-3-carboxylate (yield was 86.1%).

Step 2: Preparation of 4-amino-1-(4-methoxybenzyl)pyrrolidin-2-one

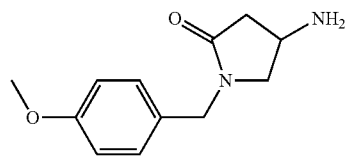 [SMILES: COc1ccc(CN2CC(N)CC2=O)cc1]

4-Amino-1-(4-methoxybenzyl)pyrrolidin-2-one was prepared in analogy to 5-amino-1-(4-methoxybenzyl)piperidin-2-one in Example 7-1 by using methyl 1-(4-methoxybenzyl)-5-oxopyrrolidine-3-carboxylate instead of methyl 1-(4-methoxybenzyl)-6-oxopiperidine-3-carboxylate.

Step 3: Preparation of 1'-{[5-chloro-1-(5-oxopyrrolidin-3-yl)-1H-benzimidazol-2-yl]methyl}spiro[cyclopropane-1,3'-pyrrolo[2,3-c]pyridin]-2'(1'H)-one The title compound was prepared in analogy to Example 7-1 by using 4-amino-1-(4-methoxybenzyl)pyrrolidin-2-one instead of 5-amino-1-(4-methoxybenzyl)piperidin-2-one.

Example 8-1

1'-{[5-Chloro-1-(1-methyl-5-oxopyrrolidin-3-yl)-1H-benzimidazol-2-yl]methyl}spiro[cyclopropane-1,3'-pyrrolo[2,3-c]pyridin]-2'(1'H)-one To a cooled solution of 1'-{[5-chloro-1-(5-oxopyrrolidin-3-yl)-1H-benzimidazol-2-yl]methyl}spiro[cyclopropane-1,3'-pyrrolo[2,3-c]pyridin]-2'(1'H)-one (100 mg, 0.246 mmol) in N,N-dimethylfromamide (5 mL) was added sodium hydride (10.0 mg, 0.246 mmol) in an ice-water bath. The mixture was stirred at 0° C. for 10 minute, and then iodomethane (35 mg, 0.246 mmol) was added to the mixture dropwise at 0° C. After being stirred at 0° C. for 30 minutes, the reaction mixture was purified by preparative HPLC to afford 15.0 mg of the title product.

Example 8-2

1'-{[5-Chloro-1-(1-ethyl-5-oxopyrrolidin-3-yl)-1H-benzimidazol-2-yl]methyl}spiro[cyclopropane-1,3'-pyrrolo[2,3-c]pyridin]-2'(1'H)-one The title compound was prepared in analogy to Example 8-1 by using iodoethane instead of iodomethane.

Example 9-1 and Example 9-2

1'-({5-Chloro-1-[(3S)-1,1-dioxidotetrahydrothiophen-3-yl]-7-fluoro-1H-benzimidazol-2-yl}methyl)spiro[cyclopropane-1,3'-pyrrolo[2,3-c]pyridin]-2'(1'H)-one and 1'-({5-Chloro-1-[(3R)-1,1-dioxidotetrahydrothiophen-3-yl]-7-fluoro-1H-benzimidazol-2-yl}methyl)spiro[cyclopropane-1,3'-pyrrolo[2,3-c]pyridin]-2'(1'H)-one Step 1: Preparation of N-(4-chloro-2-fluorophenyl)tetrahydrothiophen-3-amine 1,1-dioxide

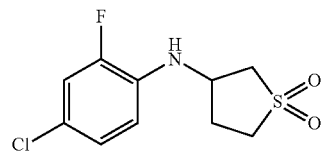 [SMILES: O=S1(=O)CCC(Nc2ccc(Cl)cc2F)C1]

A mixture of 4-chloro-2-fluoroaniline (50 g, 344 mmol), 2,5-dihydrothiophene 1,1-dioxide (40.8 g, 345 mmol) and cesium carbonate (225 g, 692 mmol) in N,N-dimethylformamide (400 mL) was heated with stirring at 80° C. for 16 hours. The resulting mixture was then poured into water (2 L) and then extracted with ethyl acetate (1 L×3). The organic layer was washed with brine (1 L×2), and then dried over sodium sulfate and concentrated in vacuo. The residue was purified by flash column (eluting with 25% ethyl acetate in petroleum ether) to afford 15.0 g of N-(4-chloro-2-fluorophenyl)tetrahydrothiophen-3-amine 1,1-dioxide (yield was 16.5%).

Step 2: Preparation of N-(4-chloro-2-fluoro-6-nitrophenyl)tetrahydrothiophen-3-amine 1,1-dioxide

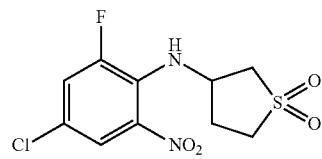 [SMILES: O=[N+]([O-])c1cc(Cl)cc(F)c1NC1CCS(=O)(=O)C1]

To a three necked bottle which containing cooled concentrated sulfuric acid (80 mL) at 0° C. was added N-(4-chloro-2-fluorophenyl)tetrahydrothiophen-3-amine 1,1-dioxide (10.0 g, 37.9 mmol) slowly and then followed by addition of nitric acid (3 mL) dropwise. The resulting mixture was stirred at 0° C. for 1 hour, and then poured into ice-water (200 g) and extracted with ethyl acetate (150 mL×3). The organic layer was washed with water (200 mL) and brine (200 mL), and then dried over sodium sulfate and concentrated in vacuo. The residue was purified by flash column (eluting with 25% ethyl acetate in petroleum ether) to afford 5.3 g of N-(4-chloro-2-fluoro-6-nitrophenyl)tetrahydrothiophen-3-amine 1,1-dioxide containing 40% of the starting material.

Step 3: Preparation of 5-chloro-$N^2$-(1,1-dioxidotetrahydrothiophen-3-yl)-3-fluorobenzene-1,2-diamine

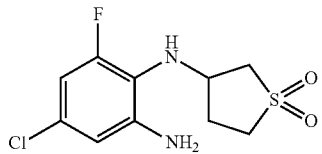

A mixture of N-(4-chloro-2-fluoro-6-nitrophenyl)tetrahydrothiophen-3-amine 1,1-dioxide (8.0 g, 15.5 mmol, 60% purity) and Raney nickel (2.0 g) in methanol (100 mL) was stirred at room temperature under hydrogen atmosphere for 4 hours. The resulting reaction mixture was filtered through silica gel and the filtrate was concentrated in vacuo. The residue was purified by column flash column (eluting with 25% ethyl acetate in petroleum ether) to afford 2.8 g of 5-chloro-$N^2$-(1,1-dioxidotetrahydrothiophen-3-yl)-3-fluorobenzene-1,2-diamine (80% purity, yield was 51.8%).

Step 4: Preparation of 5-chloro-2-(chloromethyl)-1-(1,1-dioxidotetrahydrothiophen-3-yl)-7-fluoro-1H-benzimidazole

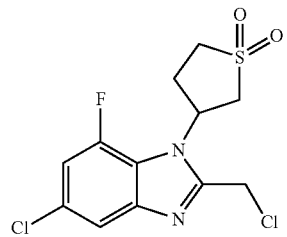 [SMILES: O=S1(=O)CCC(n2c(CCl)nc3cc(Cl)cc(F)c32)C1]

A mixture of 5-chloro-$N^2$-(1,1-dioxidotetrahydrothiophen-3-yl)-3-fluorobenzene-1,2-diamine (1.4 g, 4.0 mmol, 80% purity), 2-chloro-1,1,1-trimethoxy-ethane (4.6 g, 29.8 mmol) and methyl 4-methylbenzenesulfonate (1.7 g, 9.87 mmol) in dichloromethane (50 mL) was heated under reflux for 1 hour. The resulting reaction mixture was concentrated in vacuo and the residue was eluted through flash column with methanol and the elutriant was concentrated in vacuo. The residue was dissolved in ethyl acetate (50 mL) and the solution was washed with saturated aqueous solution of sodium bicarbonate (50 mL×3), and then dried over sodium sulfate and concentrated in vacuo to afford 1.3 g of 5-chloro-2-(chloromethyl)-1-(1,1-dioxidotetrahydrothiophen-3-yl)-7-fluoro-1H-benzimidazole (90% purity, yield was 86.7%).

Step 5: Preparation of 1'-({5-chloro-1-[(3S)-1,1-dioxidotetrahydrothiophen-3-yl]-7-fluoro-1H-benzimidazol-2-yl}methyl)spiro[cyclopropane-1,3'-pyrrolo[2,3-c]pyridin]-2'(1'H)-one and 1'-({5-chloro-1-[(3R)-1,1-dioxidotetrahydrothiophen-3-yl]-7-fluoro-1H-benzimidazol-2-yl}methyl)spiro[cyclopropane-1,3'-pyrrolo[2,3-c]pyridin]-2'(1'H)-one A mixture of spiro[cyclopropane-1,3'-pyrrolo[2,3-c]pyridin]-2'(1'H)-one (618 mg, 3.86 mmol) and sodium tert-butoxide (389 mg, 4.05 mmol) was stirred in N,N-dimethylformamide (4 mL) at room temperature for 30 minutes. Then the mixture was added dropwise over 10 minutes at 0° C. to a cooled solution of 5-chloro-2-(chloromethyl)-1-(1,1-dioxidotetrahydrothiophen-3-yl)-7-fluoro-1H-benzimidazole (1.3 g, 3.86 mmol) in N,N-dimethylformamide (10 mL). The reaction mixture was stirred for more 5 minutes, and then diluted with water (150 mL). The resulting mixture was stirred for 15 minutes. The precipitate was collected by filtration and washed with ethyl acetate, methanol and petroleum ether to afford 650 mg of racemic 1'-{[5-chloro-1-(1,1-dioxidotetrahydrothiophen-3-yl)-7-fluoro-1H-benzimidazol-2-yl]methyl}spiro[cyclopropane-1,3'-pyrrolo[2,3-c]pyridin]-2'(1'H)-one. The racemate was separated by chiral separation. The elutriant of each enantiomer was concentrated in vacuo respectively and the residue was washed with 17% ethyl acetate in petroleum ether respectively to afford 139.5 mg of 1'-({5-chloro-1-[(3S)-1,1-dioxidotetrahydrothiophen-3-yl]-7-fluoro-1H-benzimidazol-2-yl}methyl)spiro[cyclopropane-1,3'-pyrrolo[2,3-c]pyridin]-2'(1'H)-one and 182.9 mg of 1'-({5-chloro-1-[(3R)-1,1-dioxidotetrahydrothiophen-3-yl]-7-fluoro-1H-benzimidazol-2-yl}methyl)spiro[cyclopropane-1,3'-pyrrolo[2,3-c]pyridin]-2'(1'H)-one.

Example 10-1

1'-{[5-Chloro-1-(piperidin-4-yl)-1H-benzimidazol-2-yl]methyl}spiro[cyclopropane-1,3'-pyrrolo[2,3-c]pyridin]-2'(1'H)-one Step 1: Preparation of tert-butyl 4-{5-chloro-2-[(2'-oxospiro[cyclopropane-1,3'-pyrrolo[2,3-c]pyridin]-1'(2'H)-yl)methyl]-1H-benzimidazol-1-yl}piperidine-1-carboxylate

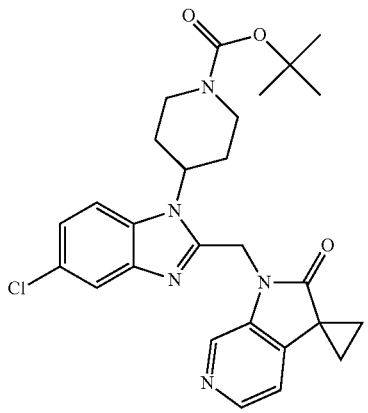 [SMILES: CC(C)(C)OC(=O)N1CCC(n2c(CN3C(=O)C4(CC4)c4ccncc43)nc3cc(Cl)ccc32)CC1]

tert-Butyl 4-{5-chloro-2-[(2'-oxospiro[cyclopropane-1,3'-pyrrolo[2,3-c]pyridin]-1'(2'H)-yl)methyl]-1H-benzimidazol-1-yl}piperidine-1-carboxylate was prepared in analogy to Example 2-1 by using tert-butyl 4-aminopiperidine-1-carboxylate (CAS No.: 87120-72-7) instead of cis-3-(methylsulfonyl)cyclobutanamine.

Step 2: Preparation of 1'-{[5-chloro-1-(piperidin-4-yl)-1H-benzimidazol-2-yl]methyl}spiro[cyclopropane-1,3'-pyrrolo[2,3-c]pyridin]-2'(1'H)-one A mixture of tert-butyl 4-{5-chloro-2-[(2'-oxospiro[cyclopropane-1,3'-pyrrolo[2,3-c]pyridin]-1'(2'H)-yl)methyl]-1H-benzimidazol-1-yl}piperidine-1-carboxylate (100 mg) and 1N hydrochloric acid solution in methanol (5 mL) was stirred at room temperature for 2 hours. The resulting mixture was basified with saturated aqueous solution of sodium carbonate and then extracted with dichloromethane. The organic layer was concentrated in vacuo and the residue was purified by flash column to afford 12 mg of the title product.

Example 10-2

1'-{[1-(Azetidin-3-yl)-5-chloro-1H-benzimidazol-2-yl]methyl}spiro[cyclopropane-1,3'-pyrrolo[2,3-c]pyridin]-2'(1'H)-one The title compound was prepared in analogy to Example 10-1 by using tert-butyl 3-aminoazetidine-1-carboxylate (CAS No.: 193269-78-2) instead of tert-butyl 4-aminopiperidine-1-carboxylate.

Example 11

1'-({5-Chloro-1-[(3R)-1-(2-methylpropanoyl)pyrrolidin-3-yl]-1H-benzimidazol-2-yl}methyl)spiro[cyclopropane-1,3'-pyrrolo[2,3-c]pyridin]-2'(1'H)-one Step 1: Preparation of tert-butyl (3R)-3-[(4-chloro-2-nitrophenyl)amino]pyrrolidine-1-carboxylate

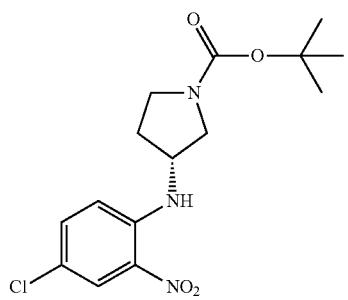

A mixture of tert-butyl (3R)-3-aminopyrrolidine-1-carboxylate (3.0 g, 16.1 mmol, CAS No.: 147081-49-0), 4-chloro-1-fluoro-2-nitrobenzene (4.24 g, 24.2 mmol) and potassium carbonate (4.44 g, 32.3 mmol) in acetonitrile (300 mL) was heated with stirring at 50° C. for 16 hours. The resulting mixture was filtered and the filtrate was concentrated in vacuo. The residue was purified by flash column (eluting with 25% ethyl acetate in petroleum ether) to afford 4.0 g of tert-butyl (3R)-3-[(4-chloro-2-nitrophenyl)amino] pyrrolidine-1-carboxylate as a white solid (yield was 72.7%).

Step 2: Preparation of tert-butyl (3R)-3-[(2-amino-4-chlorophenyl)amino]pyrrolidine-1-carboxylate

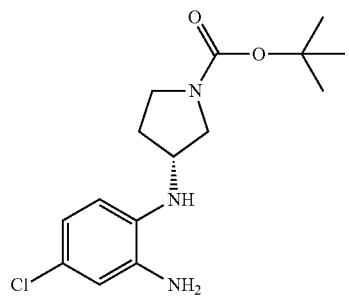 [SMILES: CC(C)(C)OC(=O)N1CC[C@@H](Nc2ccc(Cl)cc2N)C1]

A mixture of N-(4-chloro-2-fluoro-6-nitrophenyl)tetrahydrothiophen-3-amine 1,1-dioxide (4.0 g, 11.7 mmol) and Raney nickel (400 mg) in ethanol (150 mL) was stirred at room temperature under hydrogen atmosphere for 16 hours. The resulting reaction mixture was filtered through silica gel and the filtrate was concentrated in vacuo to afford 3.5 g of tert-butyl (3R)-3-[(2-amino-4-chlorophenyl)amino]pyrrolidine-1-carboxylate (yield was 95.9%).

Step 3: Preparation of tert-butyl (3R)-3-[5-chloro-2-(chloromethyl)-1H-benzimidazol-1-yl]pyrrolidine-1-carboxylate

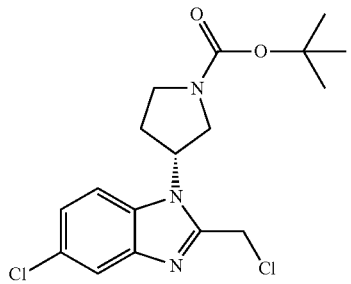 [SMILES: CC(C)(C)OC(=O)N1CC[C@@H](n2c(CCl)nc3cc(Cl)ccc32)C1]

A mixture of tert-butyl (3R)-3-[(2-amino-4-chlorophenyl) amino]pyrrolidine-1-carboxylate (1.00 g, 3.21 mmol) and 2-chloro-1,1,1-trimethoxyethane (2.50 g, 16.2 mmol) in ethanol (30 mL) was heated under reflux for 2 hours. The resulting mixture was concentrated in vacuo and the residue was purified by column (eluting with 50% ethyl acetate in petroleum ether) to afford 1.10 g of tert-butyl (3R)-3-[5-chloro-2-(chloromethyl)-1H-benzimidazol-1-yl]pyrrolidine-1-carboxylate as a white powder (yield was 92.5%).

Step 4: Preparation of 5-chloro-2-(chloromethyl)-1-[(3R)-pyrrolidin-3-yl]-1H-benzimidazole hydrochloride

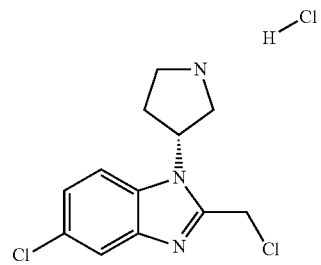 [SMILES: Cl ; ClCc1nc2cc(Cl)ccc2n1[C@@H]1CCNC1]

To a cooled 4 N hydrochloride solution in ethyl acetate (100 mL) was added tert-butyl (3R)-3-[5-chloro-2-(chloromethyl)-1H-benzimidazol-1-yl]pyrrolidine-1-carboxylate (1.10 g, 2.97 mmol) at 0° C. The resulting mixture was stirred for 16 hours while being warmed naturally to room temperature. The resulting reaction mixture was filtered and the filter cake was washed with ethyl acetate (20 mL) to afford 800 mg of 5-chloro-2-(chloromethyl)-1-[(3R)-pyrrolidin-3-yl]-1H-benzimidazole hydrochloride as a white powder (yield was 87.9%).

Step 5: Preparation of 1-{(3R)-3-[5-chloro-2-(chloromethyl)-1H-benzimidazol-1-yl]pyrrolidin-1-yl}-2-methylpropan-1-one

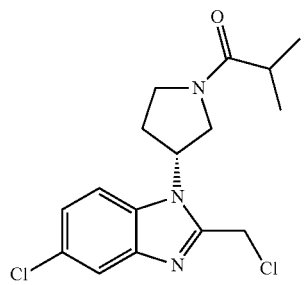 [SMILES: CC(C)C(=O)N1CC[C@@H](n2c(CCl)nc3cc(Cl)ccc32)C1]

A mixture of 5-chloro-2-(chloromethyl)-1-[(3R)-pyrrolidin-3-yl]-1H-benzimidazole hydrochloride (307 mg, 1.00 mmol), isobutyryl chloride (530 mg, 5.0 mmol) and N-ethyl-N-isopropylpropan-2-amine (390 g, 3.02 mmol) in acetonitrile (10 mL) was stirred at room temperature for 3 hours. The resulting mixture was concentrated in vacuo and the residue was purified by flash column (eluting with 100% ethyl acetate) to afford 100 mg of 1-{(3R)-3-[5-chloro-2-(chloromethyl)-1H-benzimidazol-1-yl]pyrrolidin-1-yl}-2-methylpropan-1-one as a white powder (yield was 29.4%).

Step 6: Preparation of 1'-({5-chloro-1-[(3R)-1-(2-methylpropanoyl)pyrrolidin-3-yl]-1H-benzimidazol-2-yl}methyl)spiro[cyclopropane-1,3'-pyrrolo[2,3-c]pyridin]-2'(1'H)-one A mixture of 1-{(3R)-3-[5-chloro-2-(chloromethyl)-1H-benzimidazol-1-yl]pyrrolidin-1-yl}-2-methylpropan-1-one (120 mg, 0.353 mmol), spiro[cyclopropane-1,3'-pyrrolo[2,3-c]pyridin]-2'(1'H)-one (57 mg, 0.354 mmol) and cesium carbonate (138 mg, 0.425 mmol) in N,N-dimethylformamide (3 mL) was stirred at room temperature for 16 hours. The resulting mixture was concentrated in vacuo and the residue was purified by preparative HPLC to afford 50 mg of the title product as a white powder.

Example 12

1'-({5-Chloro-1-11-(methylsulfonyl)azetidin-3-yl1-1H-benzimidazol-2-yl}methyl)spiro[cyclopropane-1,3'-pyrrolo[2,3-c]pyridin]-2'(1'H)-one Step 1: Preparation of tert-butyl 3-[(4-chloro-2-nitrophenyl)amino]azetidine-1-carboxylate

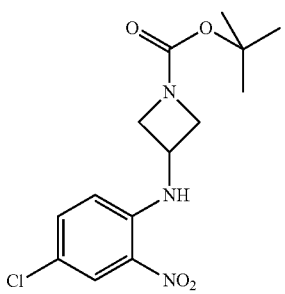 [SMILES: CC(C)(C)OC(=O)N1CC(Nc2ccc(Cl)cc2[N+](=O)[O-])C1]

tert-Butyl 3-[(4-chloro-2-nitrophenyl)amino]azetidine-1-carboxylate was prepared in analogy to tert-butyl (3R)-3-[(4-chloro-2-nitrophenyl)amino]pyrrolidine-1-carboxylate in Example 11 by using tert-butyl 3-aminoazetidine-1-carboxylate instead of tert-butyl (3R)-3-aminopyrrolidine-1-carboxylate.

Step 2: Preparation of N-(4-Chloro-2-nitrophenyl)azetidin-3-amine

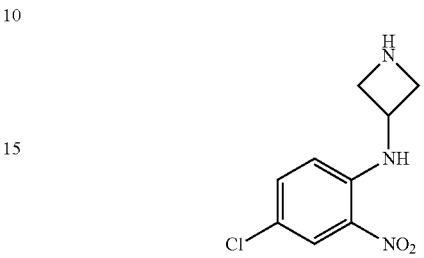

A solution of tert-butyl 3-[(4-chloro-2-nitrophenyl)amino]azetidine-1-carboxylate (2.40 g, 7.32 mmol) in dichloromethane (15 mL) was stirred with trifluoroacetic acid (3.0 mL) at room temperature overnight. The resulting mixture was diluted with dichloromethane (50 mL) and then washed with saturated aqueous solution of sodium carbonate (40 mL). The organic layer was dried over sodium sulfate and then concentrated in vacuo to afford 1.8 g of the crude N-(4-Chloro-2-nitrophenyl)azetidin-3-amine.

Step 3: Preparation of N-(4-Chloro-2-nitrophenyl)-1-(methylsulfonyl)azetidin-3-amine

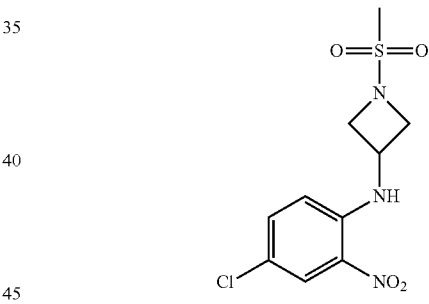

To a cooled solution of N-(4-chloro-2-nitrophenyl)azetidin-3-amine (1.80 g) in dichloromethane (20 mL) was added methanesulfonyl chloride (0.64 mL, 7.9 mmol) slowly and then followed by the addition of triethylamine (2.2 mL, 15.8 mmol) at 0° C. The resulting mixture was warmed naturally to room temperature and then stirred at the temperature for 3 hours. The reaction mixture was then concentrated in vacuo and the residue was purified by flash column to afford 1.62 g of N-(4-Chloro-2-nitrophenyl)-1-(methylsulfonyl)azetidin-3-amine as an orange solid (yield of two steps was 72.4%).

Step 4: Preparation of 1'-({5-chloro-1-[1-(methylsulfonyl)azetidin-3-yl]-1H-benzimidazol-2-yl}methyl)spiro[cyclopropane-1,3'-pyrrolo[2,3-c]pyridin]-2'(1'H)-one The title compound was prepared in analogy to Example 2-1 by using N-(4-chloro-2-nitrophenyl)-1-(methylsulfonyl)azetidin-3-amine instead of N-(4-chloro-2-nitrophenyl)-2-thiaspiro[3.3]heptan-6-amine 2,2-dioxide.

Example 13

1'-{[5-Chloro-1-(2,2-dimethyl-1,1-dioxidotetrahydrothiophen-3-yl)-1H-benzimidazol-2-yl]methyl}spiro[cyclopropane-1,3'-pyrrolo[2,3-c]pyridin]-2'(1'H)-one

Step 1: Preparation of N-[(3R)-4-hydroxy-4-methyl-1-(methylsulfanyl)pentan-3-yl]benzamide

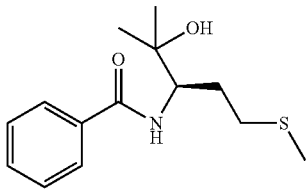 [SMILES: CSCC[C@@H](NC(=O)c1ccccc1)C(C)(C)O]

To a solution of (R)-3-amino-2-methyl-5-(methylthio)pentan-2-ol (10.0 g, 61.2 mmol, CAS No.: 1354942-48-5) in dichloromethane (200 mL) was added triethylamine (9.0 g, 89.1 mmol). The mixture was stirred for 15 minutes and then cooled to 0° C. To the cooled mixture was added benzoyl chloride (10.0 g, 71.1 mmol) and the resulting mixture was stirred at 0° C. for 1 hour. The resulting reaction mixture was washed with water (150 mL). The aqueous layer was extracted with dichloromethane (150 mL×3). The combined organic layer was washed with brine (200 mL), and then dried over sodium sulfate and concentrated in vacuo. The residue was purified by flash column (eluting with 0-90% ethyl acetate in petroleum ether) to afford 8.0 g of N-[(3R)-4-hydroxy-4-methyl-1-(methylsulfanyl)pentan-3-yl]benzamide as light yellow oil (yield was 48.9%).

Step 2: Preparation of (4R)-5,5-dimethyl-4-[2-(methylsulfanyl)ethyl]-2-phenyl-4,5-dihydro-1,3-oxazole

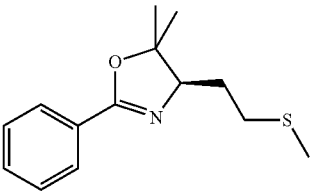 [SMILES: CSCC[C@H]1N=C(c2ccccc2)OC1(C)C]

To a solution of N-[(3R)-4-hydroxy-4-methyl-1-(methylsulfanyl)pentan-3-yl]benzamide (8.0 g, 29.9 mol) in dichloromethane (100 mL) was added 2,3,4,6,7,8,9,10-octahydropyrimido[1,2-a]azepine (10.8 g, 70.9 mol, CAS No.: 6674-22-2) and 1,1,2,2,3,3,4,4,4-nonafluorobutane-1-sulfonyl fluoride (7.2 g, 23.8 mmol, CAS No.: 375-72-4). The resulting mixture was stirred for 30 minutes at 0° C. The resulting reaction mixture was washed with water (50 mL) and the aqueous layer was extracted with dichloromethane (50 mL×3). The combined organic layer was washed with brine (50 mL), and then dried over sodium sulfate and concentrated in vacuo. The residue was purified by flash column (eluting with 0-90% ethyl acetate in petroleum ether) to afford 4.0 g of (4R)-5,5-dimethyl-4-[2-(methylsulfanyl)ethyl]-2-phenyl-4,5-dihydro-1,3-oxazole as light yellow oil (yield was 53.6%).

Step 3: Preparation of N-[(3R)-2,2-dimethyltetrahydrothiophen-3-yl]benzamide

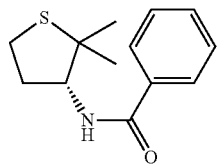 [SMILES: CC1(C)SCC[C@H]1NC(=O)c1ccccc1]

1.36 N hydrochloride in acetic acid was prepared by addition of acetyl chloride (110 mL) dropwise to a mixture of water (28 mL) and acetic acid (1 L) in an ice-water bath. To the solution of hydrochloride in acetic acid (200 mL) was added (4R)-5,5-dimethyl-4-[2-(methylsulfanyl)ethyl]-2-phenyl-4,5-dihydro-1,3-oxazole (4.0 g, 16.0 mmol). After being heated at 130° C. for 18 hours, the resulting mixture was cooled down and then poured into ice-water while the temperature was kept below 10° C. The precipitate was collected to afford 2.0 g of N-[(3R)-2,2-dimethyltetrahydrothiophen-3-yl]benzamide as a white solid (2.0 g, 53.2%).

Step 4: Preparation of N-[(3R)-2,2-dimethyl-1,1-dioxidotetrahydrothiophen-3-yl]benzamide

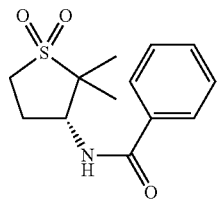 [SMILES: CC1(C)[C@H](NC(=O)c2ccccc2)CCS1(=O)=O]

To a solution of N-[(3R)-2,2-dimethyltetrahydrothiophen-3-yl]benzamide (2.0 g, 8.50 mmol) in ethyl acetate (300 mL), a saturated aqueous solution of sodium bicarbonate (200 mL) was added, and then 3-chloroperoxybenzoic acid (6.5 g, 32.0 mol, 85% purity) was added in portions during 30 minutes. The resulting mixture was stirred at room temperature for 2 hours. Then to the reaction mixture was added a saturated aqueous solution of sodium thiosulfate (500 mL) and a saturated aqueous solution of sodium bicarbonate (500 mL). After being stirred at room temperature for 1 hour, the resulting mixture was extracted with ethyl acetate (500 mL). The organic layer was washed with a saturated aqueous solution of sodium thiosulfate (500 mL), a saturated aqueous solution of sodium bicarbonate (500 mL) and brine (500 mL), and then dried over sodium sulfate and concentrated in vacuo to afford 2.0 g of N-[(3R)-2,2-dimethyl-1,1-dioxidotetrahydrothiophen-3-yl]benzamide as colorless oil (yield was 88.0%).

Step 5: Preparation of (3R)-2,2-Dimethyltetrahydrothiophen-3-amine 1,1-dioxide hydrochloride

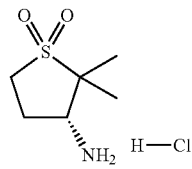

A mixture of N-[(3R)-2,2-dimethyl-1,1-dioxidotetrahydrothiophen-3-yl]benzamide (2.0 g, 7.48 mmol) and 6N hydrochloric acid (200 mL) was heated at 130° C. for 13 hours. After being cooled to room temperature, the mixture was washed with dichloromethane (200 mL×3) and the aqueous layer was concentrated in vacuo. The residue was stirred with 1,4-dioxane (100 mL). The suspension was filtered and the filter cake was washed with 1,4-dioxane and dried in vacuo to afford 1.0 g of hydrochloride salt of (3R)-2,2-dimethyltetrahydrothiophen-3-amine 1,1-dioxide hydrochloride (yield was 66.9%).

Step 6: Preparation of (3R)-N-(4-chloro-2-nitrophenyl)-2,2-dimethyltetrahydrothiophen-3-amine 1,1-dioxide

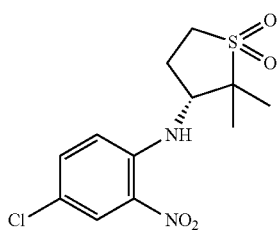 [SMILES: CC1(C)[C@H](Nc2ccc(Cl)cc2[N+](=O)[O-])CCS1(=O)=O]

A mixture of 4-chloro-1-fluoro-2-nitrobenzene (1.86 g, 10.6 mmol), (3R)-2,2-dimethyltetrahydrothiophen-3-amine 1,1-dioxide hydrochloride (1.00 g, 5.01 mmol), potassium carbonate (830 mg, 6.0 mmol) and triethylamine (1.20 g, 11.9 mmol) in N,N-dimethylformamide (10 mL) was heated at 140° C. for 30 minutes under microwave irradiation. The resulting reaction mixture was cooled and then poured into ice-water which was kept below 10° C. (20 mL). The precipitate was collected by filtration, and then washed with water and dried in vacuo. The crude product was purified by preparative TLC to afford 500 mg of (3R)-N-(4-chloro-2-nitrophenyl)-2,2-dimethyltetrahydrothiophen-3-amine 1,1-dioxide (yield was 31.3%).

Step 7: Preparation of 4-chloro-N¹-[(3R)-2,2-dimethyl-1,1-dioxidotetrahydrothiophen-3-yl]benzene-1,2-diamine

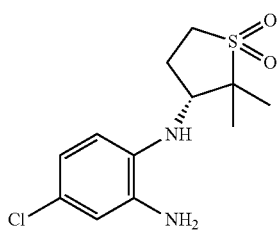

A solution of (3R)-N-(4-chloro-2-nitrophenyl)-2,2-dimethyltetrahydrothiophen-3-amine 1,1-dioxide (1.50 g, 4.68 mmol) in methanol (40 mL) was stirred with Raney nickel (300 mg) under hydrogen atmosphere overnight. The resulting mixture was filtered and the filtrate was concentrated in vacuo to afford the crude 4-chloro-N¹-[(3R)-2,2-dimethyl-1,1-dioxidotetrahydrothiophen-3-yl]benzene-1,2-diamine.

Step 8: Preparation of 5-chloro-2-(chloromethyl)-1-[(3R)-2,2-dimethyl-1,1-dioxidotetrahydrothiophen-3-yl]-1H-benzimidazole

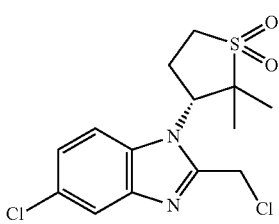 [SMILES: CC1(C)[C@H](n2c(CCl)nc3cc(Cl)ccc32)CCS1(=O)=O]

A mixture of 4-chloro-N¹-[(3R)-2,2-dimethyl-1,1-dioxidotetrahydrothiophen-3-yl]benzene-1,2-diamine (300 mg, 1.01 mmol), 2-chloro-1,1,1-trimethoxyethane (1.95 g, 12.6 mmol) and 4-methylbenzenesulfonic acid (480 mg, 2.18 mmol) was heated at 60° C. for 45 minutes under microwave irradiation. The reaction mixture was concentrated in vacuo and the residue was purified by preparative HPLC to afford 185 mg of 5-chloro-2-(chloromethyl)-1-[(3R)-2,2-dimethyl-1,1-dioxidotetrahydrothiophen-3-yl]-1H-benzimidazole (yield was 52.8%).

Step 9: Preparation of 1'-{[5-Chloro-1-(2,2-dimethyl-1,1-dioxidotetrahydrothiophen-3-yl)-1H-benzimidazol-2-yl]methyl}spiro[cyclopropane-1,3'-pyrrolo[2,3-c]pyridin]-2'(1'H)-one The title compound was prepared in analogy to Example 1-1 by using 5-chloro-2-(chloromethyl)-1-[(3R)-2,2-dimethyl-1,1-dioxidotetrahydrothiophen-3-yl]-1H-benzimidazole instead of 5-chloro-2-(chloromethyl)-1-[cis-3-(methylsulfonyl)cyclobutyl]-1H-benzimidazole.

Example 14-1 and Example 14-2

1'-{[5-Chloro-1-(cis-3-hydroxycyclobutyl)-1H-benzimidazol-2-yl]methyl}spiro[cyclopropane-1,3'-pyrrolo[2,3-c]pyridin]-2'(1'H)-one and 1'-{[5-Chloro-1-(trans-3-hydroxycyclobutyl)-1H-benzimidazol-2-yl]methyl}spiro[cyclopropane-1,3'-pyrrolo[2,3-c]pyridin]-2'(1'H)-one Step 1: Preparation of 1'-{[5-chloro-1-(3-hydroxycyclobutyl)-1H-benzimidazol-2-yl]methyl}spiro[cyclopropane-1,3'-pyrrolo[2,3-c]pyridin]-2'(1'H)-one

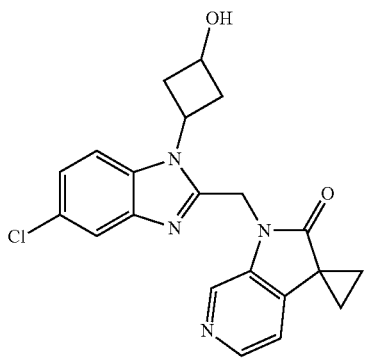 [SMILES: O=C1N(Cc2nc3cc(Cl)ccc3n2C2CC(O)C2)c2cnccc2C12CC2]

1'-{[5-Chloro-1-(3-hydroxycyclobutyl)-1H-benzimidazol-2-yl]methyl}spiro[cyclopropane-1,3'-pyrrolo[2,3-c]pyridin]-2'(1'H)-one was prepared in analogy to Example 2-1 by using 3-aminocyclobutanol (CAS No.: 4640-44-2) instead of 2-thiaspiro[3.3]heptan-6-amine 2,2-dioxide.

Step 2: Preparation of 1'-{[5-chloro-1-(cis-3-hydroxycyclobutyl)-1H-benzimidazol-2-yl]methyl}spiro[cyclopropane-1,3'-pyrrolo[2,3-c]pyridin]-2'(1'H)-one and 1'-{[5-Chloro-1-(trans-3-hydroxycyclobutyl)-1H-benzimidazol-2-yl]methyl}spiro[cyclopropane-1,3'-pyrrolo[2,3-c]pyridin]-2'(1'H)-one The title compounds were prepared by separation of 1'-{[5-chloro-1-(3-hydroxycyclobutyl)-1H-benzimidazol-2- yl]methyl}spiro[cyclopropane-1,3'-pyrrolo[2,3-c]pyridin]-2'(1'H)-one by preparative HPLC.

Example 15

1'-{[5-Chloro-1-(1,1-dioxido-1,2-thiazolidin-4-yl)-1H-benzimidazol-2-yl]methyl}spiro[cyclopropane-1,3'-pyrrolo[2,3-c]pyridin]-2'(1'H)-one Step 1: Preparation of N-benzylethenesulfonamide

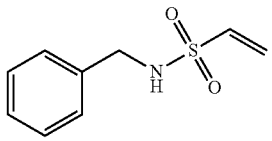

To a mixture of 2-chloroethanesulfonyl chloride (3.20 mL, 31.0 mmol, CAS No.: 1622-32-8) and 1-phenylmethanamine (3.38 mL, 31.0 mmol, CAS No.: 100-46-9) in dichloromethane (100 mL), which was cooled to 0° C., was added triethylamine (8.90 mL, 64.0 mmol) dropwise. The resulting mixture was warmed naturally to room temperature and stirred at the temperature overnight. The resulting mixture was concentrated in vacuo and the residue was purified by flash column (eluting with 0-40% ethyl acetate in petroleum ether) to afford 3.4 g of N-benzylethenesulfonamide as viscous oil (yield was 55.5%).

Step 2: Preparation of
N-benzyl-N-(prop-2-en-1-yl)ethenesulfonamide

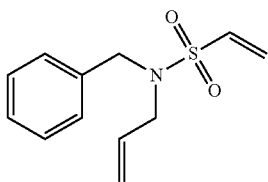 [SMILES: C=CCN(Cc1ccccc1)S(=O)(=O)C=C]

A mixture of N-benzylethenesulfonamide (3.40 g, 17.2 mmol), 3-bromoprop-1-ene (1.50 mL, 17.2 mmol, CAS No.: 106-95-6) and potassium carbonate (4.14 g, 30.0 mmol) in N,N-dimethylformamide (20 mL) was stirred at room temperature for 4 hours. The resulting mixture was diluted with ethyl acetate (50 mL) and then washed with brine (40 mL×3). The organic layer was dried over sodium sulfate and then concentrated in vacuo. The residue was purified by flash column ((eluting with 0-40% ethyl acetate in petroleum ether) to afford 3.02 g of N-benzyl-N-(prop-2-en-1-yl)ethenesulfonamide as viscous oil (yield was 74.0%).

Step 3: Preparation of
2-benzyl-2,3-dihydro-1,2-thiazole 1,1-dioxide

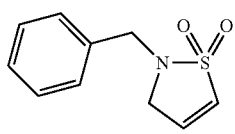 [SMILES: O=S1(=O)C=CCN1Cc1ccccc1]

A flask with a solution of N-benzyl-N-(prop-2-en-1-yl)ethenesulfonamide (3.00 g, 12.6 mmol) in anhydrous dichloromethane (20 mL) was degassed and backfilled with argon and heated at 45° C. Then [1,3-bis-(2,4,6-trimethylphenyl)-2-imidazolidinylidene]dichloro(phenylmethylene)(tricyclohexylphosphine)ruthenium ($2^{nd}$ generation Grubbs catalyst, 268 mg, 0.315 mmol, CAS No.: 246047-72-3) was added in 5 portions every 30 minutes. The resulting mixture was concentrated in vacuo and the residue was purified by flash column (eluting with 0-40% ethyl acetate in petroleum ether) to afford 1.88 g of 2-benzyl-2,3-dihydro-1,2-thiazole 1,1-dioxide as a pale solid (yield was 71.3%).

Step 4: Preparation of
N,2-dibenzyl-1,2-thiazolidin-4-amine 1,1-dioxide

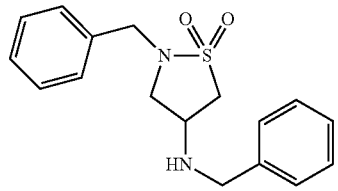 [SMILES: O=S1(=O)CC(NCc2ccccc2)CN1Cc1ccccc1]

A mixture of 2-benzyl-2,3-dihydro-1,2-thiazole 1,1-dioxide (1.46 g 6.98 mmol), 1-phenylmethanamine (0.91 mL, 8.4 mmol) and 2,3,4,6,7,8,9,10-octahydropyrimido[1,2-a]azepine (111 μL, 0.70 mmol) in anhydrous ethanol (10 mL) was stirred at room temperature overnight. The resulting mixture was concentrated in vacuo and the residue was purified by flash column (eluting with 0-40% ethyl acetate in petroleum ether) to afford 1.15 g of N,2-dibenzyl-1,2-thiazolidin-4-amine 1,1-dioxide as a semisolid (yield was 52.0%).

Step 5: Preparation of
2-benzyl-1,2-thiazolidin-4-amine 1,1-dioxide

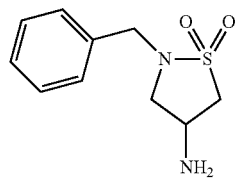 [SMILES: NC1CN(Cc2ccccc2)S(=O)(=O)C1]

A solution of N,2-dibenzyl-1,2-thiazolidin-4-amine 1,1-dioxide (1.15 g, 3.63 mmol) in ethanol was stirred with 10% palladium hydroxide on carbon (200 mg) in the presence of trifluoroacetic acid (20 μL) at room temperature overnight. The resulting mixture was basified by addition of 7N ammonia in methanol (0.5 mL) and then concentrated in vacuo. The residue was purified by flash column (eluting with 0-8% methanol in dichloromethane) to afford 680 mg of 2-benzyl-1,2-thiazolidin-4-amine 1,1-dioxide as viscous oil (yield was 84.4%).

Step 6: Preparation of 2-benzyl-N-(4-chloro-2-nitrophenyl)-1,2-thiazolidin-4-amine 1,1-dioxide

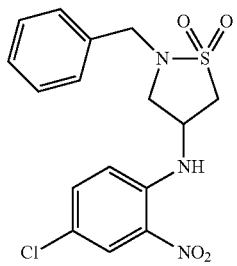 [SMILES: O=[N+]([O-])c1cc(Cl)ccc1NC1CN(Cc2ccccc2)S(=O)(=O)C1]

A mixture of 4-chloro-1-fluoro-2-nitrobenzene (525 mg, 3.00 mmol), 2-benzyl-1,2-thiazolidin-4-amine 1,1-dioxide (680 mg, 3.06 mmol) and potassium carbonate (621 mg, 4.50 mmol) was heated with stirring at 60° C. for 24 hours. The resulting mixture was diluted with ethyl acetate (100 mL) and then washed with brine (100 mL×3). The organic layer was dried over sodium sulfate and then concentrated in vacuo. The residue was purified by flash column ((eluting with 0-10% methanol in dichloromethane) to afford 660 mg of 2-benzyl-N-(4-chloro-2-nitrophenyl)-1,2-thiazolidin-4-amine 1,1-dioxide as an orange solid (yield was 57.6%).

Step 7: Preparation of N-(4-chloro-2-nitrophenyl)-1,2-thiazolidin-4-amine 1,1-dioxide

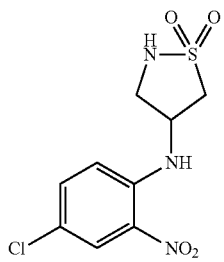 [SMILES: O=[N+]([O-])c1cc(Cl)ccc1NC1CNS(=O)(=O)C1]

A mixture of 2-benzyl-N-(4-chloro-2-nitrophenyl)-1,2-thiazolidin-4-amine 1,1-dioxide (570 mg, 1.49 mmol) and concentrated sulfuric acid (12 mL) was stirred at room temperature for 2 hours. The resulting mixture was basified with saturated aqueous solution of sodium carbonate. The aqueous layer was concentrated in vacuo to remove water. The residue was stirred with methanol (50 mL) and the mixture was filtered. The filtrate was concentrated in vacuo. The residue was purified by flash column ((eluting with 0-10% methanol in dichloromethane) to afford 250 mg of N-(4-chloro-2-nitrophenyl)-1,2-thiazolidin-4-amine 1,1-dioxide as an orange solid.

Step 8: Preparation of 1'-{[5-chloro-1-(1,1-dioxido-1,2-thiazolidin-4-yl)-1H-benzimidazol-2-yl]methyl}spiro[cyclopropane-1,3'-pyrrolo[2,3-c]pyridin]-2'(1'H)-one The title compound was prepared in analogy to Example 2-1 by using N-(4-chloro-2-nitrophenyl)-1,2-thiazolidin-4-amine 1,1-dioxide instead of N-(4-chloro-2-nitrophenyl)-2-thiaspiro[3.3]heptan-6-amine 2,2-dioxide.

Example 16

1'-{[5-Chloro-1-(2-oxa-5-azaspiro[3.4]oct-7-yl)-1H-benzimidazol-2-yl]methyl}spiro[cyclopropane-1,3'-pyrrolo[2,3-c]pyridin]-2'(1'H)-one

Step 1: Preparation of 3-(benzyl-trimethylsilanylmethyl-amino)-oxetane-3-carbonitrile

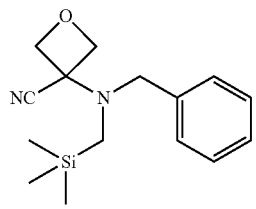 [SMILES: C[Si](C)(C)CN(Cc1ccccc1)C1(C#N)COC1]

To acetic acid (140 mL) was added benzyl-trimethylsilanylmethyl-amine (26.8 g, 138.6 mmol, CAS No.: 53215-95-5) and oxetan-3-one (5.0 g, 69.4 mmol, CAS No.: 6704-31-0) successively at 10~20° C. and then followed by the addition of trimethylsilyl cyanide (7.57 g, 76.3 mmol, CAS No.: 7677-24-9) dropwise at 0° C. The resulting mixture was stirred at room temperature for 3 days. The resulting mixture was diluted with ether, and then washed with water, 3 times of 5% acetic acid and 5 times of brine. The organic layer was dried over sodium sulfate, and then concentrated in vacuo. The residue was purified by column chromatography (eluting with 0-40% ethyl acetate in petroleum ether) to give 5.0 g of 3-(benzyl-trimethylsilanylmethyl-amino)-oxetane-3-carbonitrile as colorless oil.

Step 2: Preparation of ethyl 5-benzyl-2-oxa-5-azaspiro[3.4]octane-7-carboxylate

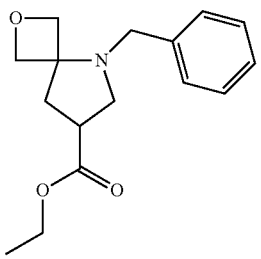 [SMILES: CCOC(=O)C1CN(Cc2ccccc2)C2(COC2)C1]

A mixture of 3-(benzyl-trimethylsilanylmethyl-amino)-oxetane-3-carbonitrile (5.0 g, 18.2 mmol), ethyl prop-2-enoate (9.12 g, 91.1 mmol, CAS No.: 9003-32-1) and silver fluoride (6.9 g, 54.7 mmol) in acetonitrile (100 mL) was stirred in dark for 3 days. The solid was removed by filtration, the filtrate was concentrated in vacuo and the residue was purified by column chromatography (eluting with 0-40% ethyl acetate in petroleum ether) to give 1.76 g of ethyl 5-benzyl-2-oxa-5-azaspiro[3.4]octane-7-carboxylate as colorless oil.

Step 3: Preparation of ethyl 2-oxa-5-azaspiro[3.4]octane-7-carboxylate

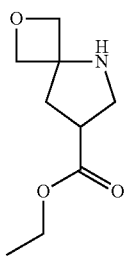

A solution of ethyl 5-benzyl-2-oxa-5-azaspiro[3.4]octane-7-carboxylate (550 mg, 2.00 mmol) in ethanol was stirred with 10% palladium hydroxide on carbon (105 mg) in the presence of trifluoroacetic acid (20 μL) at room temperature overnight. The resulting mixture was concentrated in vacuo. The residue was dissolved in dichloromethane (20 mL) and then washed with a saturated aqueous solution of sodium carbonate (20 mL). The organic layer was dried over sodium sulfate and concentrated in vacuo to afford 390 mg of ethyl 2-oxa-5-azaspiro[3.4]octane-7-carboxylate as viscous oil.

Step 4: Preparation of 5-tert-butyl 7-ethyl 2-oxa-5-azaspiro[3.4]octane-5,7-dicarboxylate

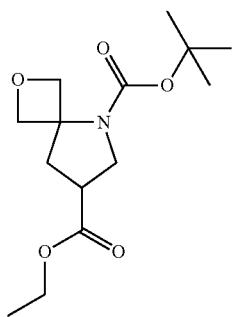 [SMILES: CCOC(=O)C1CN(C(=O)OC(C)(C)C)C2(COC2)C1]

A mixture of ethyl 2-oxa-5-azaspiro[3.4]octane-7-carboxylate (333 mg, 1.80 mmol), di-tert-butyl Bicarbonate (972 mg, 4.50 mmol, CAS No.: 24424-99-5) and triethylamine (0.30 mL, 2.16 mmol) in dichloromethane (10 mL) was stirred at room temperature for 3 hours. The resulting mixture was concentrated in vacuo. The residue was purified by flash column (eluting with 0-5% methanol in dichloromethane) to afford 514 mg of 5-tert-butyl 7-ethyl 2-oxa-5-azaspiro[3.4]octane-5,7-dicarboxylate as light viscous oil.

Step 5: Preparation of 5-(tert-butoxycarbonyl)-2-oxa-5-azaspiro[3.4]octane-7-carboxylic acid

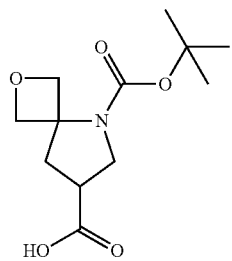 [SMILES: CC(C)(C)OC(=O)N1CC(C(=O)O)CC12COC2]

A mixture of 5-tert-butyl 7-ethyl 2-oxa-5-azaspiro[3.4] octane-5,7-dicarboxylate (514 mg, 1.80 mmol) and lithium hydroxide monohydrate (378 mg, 9.0 mmol) in water (1 mL) and methanol (10 mL) was stirred at room temperature overnight. The resulting mixture was concentrated in vacuo. The residue was stirred with a saturated aqueous solution of 2-hydroxypropane-1,2,3-tricarboxylic acid (15 mL) and then extracted with dichloromethane (15 mL×2). The combined organic layer was dried over sodium sulfate and then concentrated in vacuo to afford 444 mg of 5-(tert-butoxycarbonyl)-2-oxa-5-azaspiro[3.4]octane-7-carboxylic acid as a white solid (yield was 95.9%).

Step 6: Preparation of tert-butyl 7-{[(benzyloxy)carbonyl]amino}-2-oxa-5-azaspiro[3.4]octane-5-carboxylate

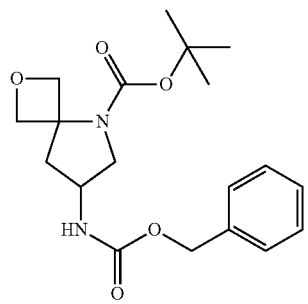 [SMILES: CC(C)(C)OC(=O)N1CC(NC(=O)OCc2ccccc2)CC12COC2]

To a solution of 5-(tert-butoxycarbonyl)-2-oxa-5-azaspiro[3.4]octane-7-carboxylic acid (444 mg, 1.72 mmol) in anhydrous toluene (5 mL) was added diphenyl phosphorazidate (407 μL, 1.89 mmol, CAS No.: 2638-88-9) and triethylamine (275 μL, 1.89 mmol). The mixture was heated at 80° C. for 3 hours. Then to the mixture was added phenylmethanol (0.5 mL). The resulting mixture was then heated at 90° C. overnight. The reaction mixture was concentrated in vacuo. The residue was purified by flash column (eluting with 0-30% ethyl acetate in petroleum ether) to afford 577 mg of tert-butyl 7-{[(benzyloxy)carbonyl] amino}-2-oxa-5-azaspiro[3.4]octane-5-carboxylate as light viscous oil (yield was 92.6%).

Step 7: Preparation of tert-butyl 7-amino-2-oxa-5-azaspiro[3.4]octane-5-carboxylate

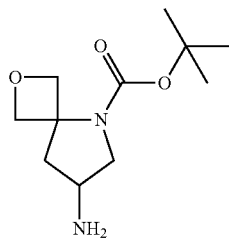 [SMILES: CC(C)(C)OC(=O)N1CC(N)CC12COC2]

A solution of tert-butyl 7-{[(benzyloxy)carbonyl]amino}-2-oxa-5-azaspiro[3.4]octane-5-carboxylate (566 mg, 1.56 mmol) in methanol was stirred with 10% palladium on carbon (100 mg) under hydrogen atmosphere at room temperature for 50 minutes. The resulting mixture was filtered and then concentrated in vacuo to afford 343 mg of tert-butyl 7-amino-2-oxa-5-azaspiro[3.4]octane-5-carboxylate as light viscous oil (yield was 96.3%).

Step 8: Preparation of tert-butyl 7-[(4-chloro-2-nitrophenyl)amino]-2-oxa-5-azaspiro[3.4]octane-5-carboxylate

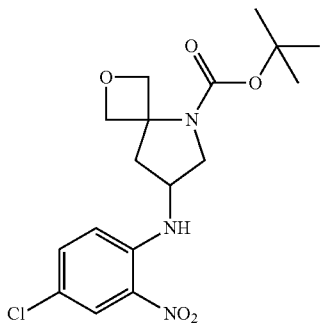 [SMILES: CC(C)(C)OC(=O)N1CC(Nc2ccc(Cl)cc2[N+](=O)[O-])CC12COC2]

A mixture of 4-chloro-1-fluoro-2-nitrobenzene (264 mg, 1.50 mmol), tert-butyl 7-amino-2-oxa-5-azaspiro[3.4]octane-5-carboxylate (343 mg, 1.50 mmol) and triethylamine (0.44 mL, 3.12 mmol) in tetrahydrofuran was stirred at room temperature overnight and then heated under reflux for 5 hours. The resulting mixture was concentrated in vacuo and the residue was purified by flash column (eluting with 0-5% methanol in dichloromethane) to afford 438 mg of tert-butyl 7-[(4-chloro-2-nitrophenyl)amino]-2-oxa-5-azaspiro[3.4]octane-5-carboxylate as an orange solid (yield was 76.1%).

Step 9: Preparation of tert-butyl 3-{5-chloro-2-[(2'-oxospiro[cyclopropane-1,3'-pyrrolo[2,3-c]pyridin]-1'(2'H)-yl)methyl]-1H-benzimidazol-1-yl}-2-oxa-5-azaspiro[3.4]octane-5-carboxylate

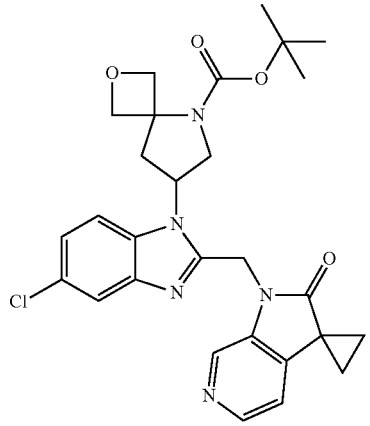 [SMILES: CC(C)(C)OC(=O)N1CC(n2c(CN3C(=O)C4(CC4)c4ccncc43)nc3cc(Cl)ccc32)CC12COC2]

tert-Butyl 3-{5-chloro-2-[(2'-oxospiro[cyclopropane-1,3'-pyrrolo[2,3-c]pyridin]-1'(2'H)-yl)methyl]-1H-benzimidazol-1-yl}-2-oxa-5-azaspiro[3.4]octane-5-carboxylate was prepared in analogy to Example 2-1 by using tert-butyl 7-[(4-chloro-2-nitrophenyl)amino]-2-oxa-5-azaspiro[3.4]octane-5-carboxylate instead of N-(4-chloro-2-nitrophenyl)-2-thiaspiro[3.3]heptan-6-amine 2,2-dioxide.

Step 10: Preparation of 1'-{[5-chloro-1-(2-oxa-5-azaspiro[3.4]oct-7-yl)-1H-benzimidazol-2-yl]methyl}spiro[cyclopropane-1,3'-pyrrolo[2,3-c]pyridin]-2'(1'H)-one To a cooled solution of tert-butyl 3-{5-chloro-2-[(2'-oxospiro[cyclopropane-1,3'-pyrrolo[2,3-c]pyridin]-1'(2'H)-yl)methyl]-1H-benzimidazol-1-yl}-2-oxa-5-azaspiro[3.4]octane-5-carboxylate (97.7 mg, 0.182 mmol) in dichloromethane (4.0 mL) was added trifluoroacetic acid (1.0 mL) dropwise at 0° C. The resulting mixture was warmed naturally to room temperature and then stirred at the temperature for 1.5 hours. The reaction mixture was diluted with dichloromethane (20 mL) and then washed with a saturated solution of sodium carbonate (20 mL). The aqueous layer was extracted with dichloromethane (20 mL). The combined organic layer was dried over sodium sulfate and then concentrated in vacuo. The residue was purified by preparative HPLC to afford 31.2 mg of the title product as a white solid.

Example 17

1'-{[5-Chloro-1-(1,1-dioxidotetrahydrothiophen-3-yl)-7-fluoro-1H-indol-2-yl]methyl}spiro[cyclopropane-1,3'-pyrrolo[2,3-c]pyridin]-2'(1'H)-one

Step 1: Preparation of (5-chloro-7-fluoro-1H-indol-2-yl)methanol

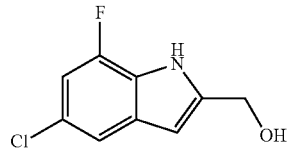 [SMILES: OCc1cc2cc(Cl)cc(F)c2[nH]1]

To a cooled solution of ethyl 5-chloro-7-fluoro-1H-indole-2-carboxylate (4.56 g, 20.0 mmol, CAS No.: 887578-55-4) in tetrahydrofuran (40 mL) in an ice-water bath was added lithium aluminium hydride solution in tetrahydrofuran (2 M, 10 mL) dropwise at 0° C. The resulting mixture was stirred at 0° C. for 2 hours. The reaction was quenched by addition of water (1 mL). After being stirred for 30 minutes, the mixture was filtered and the filtrate was concentrated in vacuo. The residue was dissolved in dichloromethane (50 mL) and washed with brine (50 mL). The separated aqueous layer was extracted with dichloromethane (50 mL). The combined organic layer was dried over sodium sulfate and then concentrated in vacuo to afford 3.56 g of the crude (5-chloro-7-fluoro-1H-indol-2-yl)methanol (yield was 89.2%).

Step 2: Preparation of 2-(([tert-butyl(dimethyl)silyl]oxy}methyl)-5-chloro-7-fluoro-1H-indole

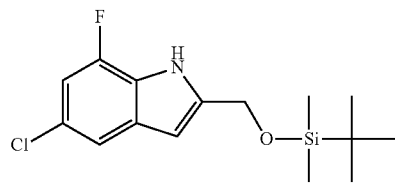 [SMILES: CC(C)(C)[Si](C)(C)OCc1cc2cc(Cl)cc(F)c2[nH]1]

A mixture of (5-chloro-7-fluoro-1H-indol-2-yl)methanol (3.56 g, 17.8 mmol), tert-butyl-chloro-dimethylsilane (3.67 g, 24.0 mmol, CAS No.: 187979-91-5) and imidazole (2.04 g, 30.0 mmol) in N,N-dimethylformamide (30 mL) was stirred at room temperature for 1 hour. The mixture was diluted with ethyl acetate (50 mL), and then washed with brine (30 mL×2), then dried over sodium sulfate and concentrated in vacuo. The residue was purified by flash column (eluting with 0-50% of ethyl acetate in petroleum) to afford 5.44 g of 2-({[tert-butyl(dimethyl)silyl]oxy}methyl)-5-chloro-7-fluoro-1H-indole as viscous oil (yield was 97.4%).

Step 3: Preparation of 2-({[tert-butyl(dimethyl)silyl]oxy}methyl)-5-chloro-1-(1,1-dioxidotetrahydrothiophen-3-yl)-7-fluoro-1H-indole

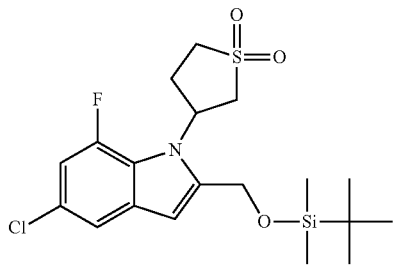 [SMILES: CC(C)(C)[Si](C)(C)OCc1cc2cc(Cl)cc(F)c2n1C1CCS(=O)(=O)C1]

To a solution of 2-({[tert-butyl(dimethyl)silyl]oxy}methyl)-5-chloro-7-fluoro-1H-indole (2.50 g, 8.0 mmol) in N,N-dimethylformamide (20 mL) was added sodium hydride (960 mg, 24.0 mmol, 60% purity) in portions. The mixture was then stirred at room temperature for 10 minutes. To the resulting mixture was added 2,5-dihydrothiophene 1,1-dioxide (9.44 g, 80.0 mmol). After being stirred at room temperature for 2 days, the reaction mixture was diluted with water (30 mL) and then extracted with ethyl acetate (30 mL×2). The combined organic layer was washed with brine (25 mL×2), and then dried over sodium sulfate and concentrated in vacuo. The residue was purified by flash column (eluting with 20-50% of ethyl acetate in petroleum) to afford 230 mg of 2-({[tert-butyl(dimethyl)silyl]oxy}methyl)-5-chloro-1-(1,1-dioxidotetrahydrothiophen-3-yl)-7-fluoro-1H-indole.

Step 4: Preparation of [5-chloro-1-(1,1-dioxidotetrahydrothiophen-3-yl)-7-fluoro-1H-indol-2-yl]methanol

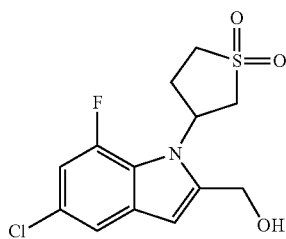 [SMILES: O=S1(=O)CCC(n2c(CO)cc3cc(Cl)cc(F)c32)C1]

A mixture of 2-({[tert-butyl (dim ethyl)silyl]oxy}methyl)-5-chloro-1-(1,1-dioxidotetrahydrothiophen-3-yl)-7-fluoro-1H-indole (230 mg, 0.53 mmol) and tetrabutyl ammonium fluoride solution in tetrahydrofuran (1 M, 0.5 mL) in tetrahydrofuran (4 mL) was stirred at room temperature overnight. The mixture was then concentrated in vacuo and the residue was purified by flash column (eluting with 0-50% of ethyl acetate in petroleum) to afford 118 mg of [5-chloro-1-(1,1-dioxidotetrahydrothiophen-3-yl)-7-fluoro-1H-indol-2-yl]methanol.

Step 5: Preparation of 1'-{[5-chloro-1-(1,1-dioxidotetrahydrothiophen-3-yl)-7-fluoro-1H-indol-2-yl]methyl}spiro[cyclopropane-1,3'-pyrrolo[2,3-c]pyridin]-2'(1'H)-one To a cooled solution of [5-chloro-1-(1,1-dioxidotetrahydrothiophen-3-yl)-7-fluoro-1H-indol-2-yl]methanol (118 mg, 0.37 mmol) in dichloromethane (20 mL) was added triethylamine (154 μL, 1.11 mmol) and methanesulfonyl chloride (39 μL, 0.50 mmol) at 0° C. After being stirred at 0° C. for 2 hours, the resulting mixture was washed with brine (25 mL×2), and then dried over sodium sulfate and concentrated in vacuo. The residue and spiro[cyclopropane-1,3'-pyrrolo[2,3-c]pyridin]-2'(1'H)-one (56 mg, 0.35 mmol) and sodium 2-methylpropan-2-olate (50.9 mg, 0.53 mmol) in N,N-dimethylformamide (5 mL) was stirred at room temperature overnight. The resulting mixture was purified by preparative HPLC to afford 30.2 mg of the title product.

Example 18

1'-{[5-Chloro-1-(1,1-dioxidotetrahydrothiophen-3-yl)-1H-indol-2-yl]methyl}spiro[cyclopropane-1,3'-pyrrolo[2,3-c]pyridin]-2'(1'H)-one Step 1: Preparation of methyl 5-chloro-1-(phenylsulfonyl)-1H-indole-2-carboxylate

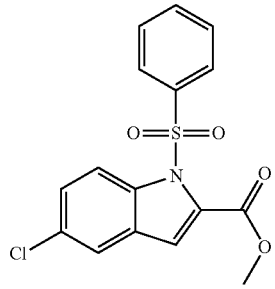 [SMILES: COC(=O)c1cc2cc(Cl)ccc2n1S(=O)(=O)c1ccccc1]

To a suspension of methyl 5-chloro-1H-indole-2-carboxylate (7.56 g, 36.0 mmol, CAS No.: 10517-21-2) and sodium hydride (1.70 g, 43.0 mmol, 60% purity in mineral oil) in N,N-dimethylformamide (100 mL) was added benzenesulfonyl chloride (6.1 mL, 47.0 mmol) dropwise in an ice-water bath. After being stirred at room temperature for 2 hours, the mixture was then poured into ice water (100 mL). The precipitate was collected by filtration, which was washed with petroleum ether (50 mL), and then dried in vacuo to afford 11.6 g of methyl 5-chloro-1-(phenylsulfonyl)-1H-indole-2-carboxylate as a pale white solid (yield was 92%).

Step 2: Preparation of [5-chloro-1-(phenylsulfonyl)-1H-indol-2-yl]methanol

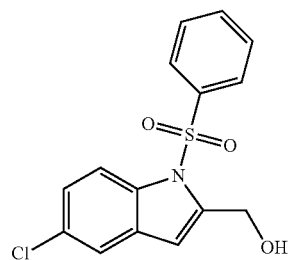 [SMILES: O=S(=O)(c1ccccc1)n1c(CO)cc2cc(Cl)ccc21]

To a suspension of lithium aluminium hydride (1.9 g, 50 mmol) in tetrahydrofuran (150 mL) at 0° C. was added methyl 5-chloro-1-(phenylsulfonyl)-1H-indole-2-carboxylate (11.6 g, 33 mmol) in portions. After being stirred at room temperature for 3 hours, the resulting mixture was quenched with methanol, then filtered through a celite pad. The celite pad was washed with dichloromethane (100 mL).

The filtrate was concentrated in vacuo to afford 9.7 g of [5-chloro-1-(phenylsulfonyl)-1H-indol-2-yl]methanol as brown oil (yield was 91%).

Step 3: Preparation of 5-chloro-2-(chloromethyl)-1-(phenylsulfonyl)-1H-indole

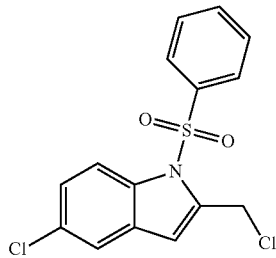 [SMILES: O=S(=O)(c1ccccc1)n1c(CCl)cc2cc(Cl)ccc21]

To a solution of [5-chloro-1-(phenylsulfonyl)-1H-indol-2-yl]methanol (1.93 g, 6.0 mmol) in dichloromethane (150 mL) was added a solution of thionyl chloride (2.7 mL, 37 mmol) in dichloromethane (10 mL) in an ice water bath. After being stirred at room temperature for 4 hours, the mixture was concentrated in vacuo to afford a light brown solid which was used for next step without further purification.

Step 4: Preparation of 1'-{[5-chloro-1-(phenylsulfonyl)-1H-indol-2-yl]methyl}spiro[cyclopropane-1,3'-pyrrolo[2,3-c]pyridin]-2'(1'H)-one

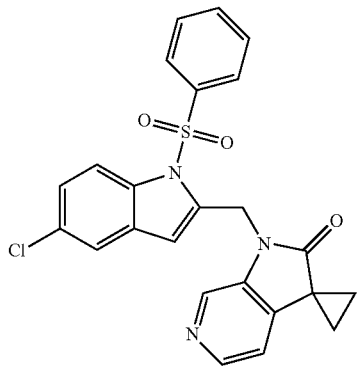 [SMILES: O=C1N(Cc2cc3cc(Cl)ccc3n2S(=O)(=O)c2ccccc2)c2cnccc2C12CC2]

To a suspension of spiro[cyclopropane-1,3'-pyrrolo[2,3-c]pyridin]-2'(1'H)-one (960 mg, 6.0 mmol) and sodium hydride (0.72 g, 18 mmol) in N,N-dimethylformamide (10 mL) was added a solution of 5-chloro-2-(chloromethyl)-1-(phenyl sulfonyl)-1H-indole (2.04 g, 6.0 mmol) in N,N-dimethylformamide (5 mL) dropwise in an ice-water bath. After being stirred at room temperature for 1 hour, the reaction mixture was poured into ice water (20 mL) and then extracted with dichloromethane (30 mL×2). The combined organic layer was dried over anhydrous sodium sulfate, and then concentrated in vacuo. The residue was purified by flash silica gel chromatography (eluting with 0-5% methanol in dichloromethane) to afford 600 mg of 1'-{[5-chloro-1-(phenylsulfonyl)-1H-indol-2-yl]methyl}spiro[cyclopropane-1,3'-pyrrolo[2,3-c]pyridin]-2'(1'H)-one as a brown solid (yield was 21.5%).

Step 5: Preparation of 1'-[(5-chloro-1H-indol-2-yl)methyl]spiro[cyclopropane-1,3'-pyrrolo[2,3-c]pyridin]-2'(1'H)-one

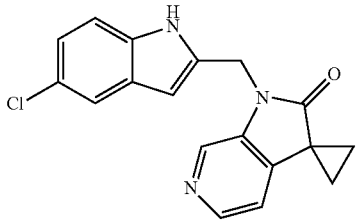 [SMILES: O=C1N(Cc2cc3cc(Cl)ccc3[nH]2)c2cnccc2C12CC2]

A mixture of 1'-{[5-chloro-1-(phenyl sulfonyl)-1H-indol-2-yl]methyl}spiro[cyclopropane-1,3'-pyrrolo[2,3-c]pyridin]-2'(1'H)-one (167 mg, 0.36 mmol) and tetrabutylammonium fluoride in tetrahydrofuran (1 mL, 1.0 M) in tetrahydrofuran (2 mL) was stirred at room temperature for 16 hours. The resulting mixture was concentrated in vacuo and the residue was extracted with ethyl acetate (20 mL×2), and then washed with a saturated aqueous solution of ammonium chloride (20 mL×2) and water (20 mL×2), then dried over anhydrous sodium sulfate and concentrated in vacuo. The residue was used for next step without further purification.

Step 6: Preparation of 1'-{[5-chloro-1-(1,1-dioxido-tetrahydrothiophen-3-yl)-1H-indol-2-yl]methyl}spiro[cyclopropane-1,3'-pyrrolo[2,3-c]pyridin]-2'(1'H)-one To a solution of 1'-[(5-chloro-1H-indol-2-yl)methyl]spiro[cyclopropane-1,3'-pyrrolo[2,3-c]pyridin]-2'(1'H)-one (65.0 mg, 0.20 mmol) and 2,5-dihydrothiophene 1,1-dioxide (236 mg, 2.0 mmol) in N,N-dimethylformamide (2 mL) was added sodium hydride (40 mg, 1.0 mmol, 60% dispersion in mineral oil). After being stirred at room temperature overnight, the resulting mixture was purified by preparative HPLC to afford the title product.

Example 19

1'-{[5-Chloro-1-(1,1-dioxidotetrahydrothiophen-3-yl)-1H-pyrrolo[2,3-b]pyridin-2-yl]methyl}spiro[cyclopropane-1,3'-pyrrolo[2,3-c]pyridin]-2'(1'H)-one Step 1: Preparation of 1'-{[5-chloro-1H-pyrrolo[2,3-b]pyridin-2-yl]methyl}spiro[cyclopropane-1,3'-pyrrolo[2,3-c]pyridin]-2'(1'H)-one

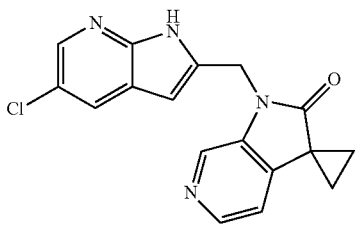 [SMILES: O=C1N(Cc2cc3cc(Cl)cnc3[nH]2)c2cnccc2C12CC2]

1'-{[5-Chloro-1H-pyrrolo[2,3-b]pyridin-2-yl]methyl}spiro[cyclopropane-1,3'-pyrrolo[2,3-c]pyridin]-2'

(1'H)-one was prepared in analogy to 1'-[(5-chloro-1H-indol-2-yl)methyl]spiro[cyclopropane-1,3'-pyrrolo[2,3-c]pyridin]-2'(1'H)-one in Example 18 by using methyl 5-chloro-1H-pyrrolo[2,3-b]pyridine-2-carboxylate (CAS No.: 952182-19-3) instead of methyl 5-chloro-1H-indole-2-carboxylate.

Step 2: Preparation of 1'-{[5-chloro-1-(1,1-dioxido-tetrahydrothiophen-3-yl)-1H-pyrrolo[2,3-b]pyridin-2-yl]methyl}spiro[cyclopropane-1,3'-pyrrolo[2,3-c]pyridin]-2'(1'H)-one To a solution of 1'-{[5-chloro-1H-pyrrolo[2,3-b]pyridin-2-yl]methyl}spiro[cyclopropane-1,3'-pyrrolo[2,3-c]pyridin]-2'(1'H)-one (97.8 mg, 0.30 mmol) and 2,5-dihydrothiophene 1,1-dioxide (1.18 g, 10.0 mmol) in acetonitrile (5 mL) was added cesium carbonate (700 mg, 2.15 mmol). After being heated with stirring at 80° C. overnight, the mixture was diluted with dichloromethane and then filtered. The filtrate was concentrated in vacuo and the residue was purified by preparative HPLC to afford the title product.

BIOLOGICAL EXAMPLES

Example 20

Viral Cytopathic Effect (CPE) Assay

To measure anti-RSV activity of compounds, 96-well plates are seeded with $6 \times 10^3$ cells per well in Dulbecco's modified Eagle's medium (DMEM) containing 10% fetal bovine serum (FBS). Cells are infected the next day with sufficient RSV Long strain (ATCC) to produce an approximately 80-90% cytopathic effect after 6 days, in the presence of serial half-log diluted compound in a total volume of 200 μL per well. The viability of cells is assessed after 6 days using Cell Counting kit-8 (Dojindo Molecular Technologies). The absorbance at 450 nm and referenced at 630 nm is measured to determine 50% effective concentration ($EC_{50}$).

The compounds of the present invention were tested for their anti-RSV activity, and the activation as described herein. The Examples were tested in the above assay and found to have $EC_{50}$ of about 0.0001 μM to about 10 μM. Particular compound of formula (I) were found to have $EC_{50}$ of about 0.0001 μM to about 1 μM. Further particular compound of formula (I) were found to have $EC_{50}$ of about 0.0001 μM to about 0.1 μM.

Results of CPE assays are given in Table 1.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. Compounds of formula (I)

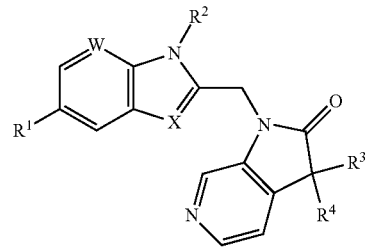

wherein
$R^1$ is halogen;
$R^2$ is azetidinyl, which is unsubstituted or substituted by $C_{1-6}$alkylsulfonyl; $C_{1-6}$alkoxycarbonylpyrrolidinyl; $C_{1-6}$alkylcarbonylpyrrolidinyl; cycloalkyl, which is unsubstituted or substituted by $C_{1-6}$alkyl, $C_{1-6}$alkylsulfonyl, carboxy, halogen or hydroxy; dioxo-tetrahydrothiophenyl, which is unsubstituted or substituted by $C_{1-6}$alkyl; dioxo-tetrahydrothiopyranyl; dioxo-thietanyl; oxo-thietanyl; oxo-pyrrolidinyl, which is unsubstituted or substituted by $C_{1-6}$alkyl; oxetanyl; oxopiperidinyl; piperidinyl; tetrahydrofuranyl; tetrahydropyranyl;

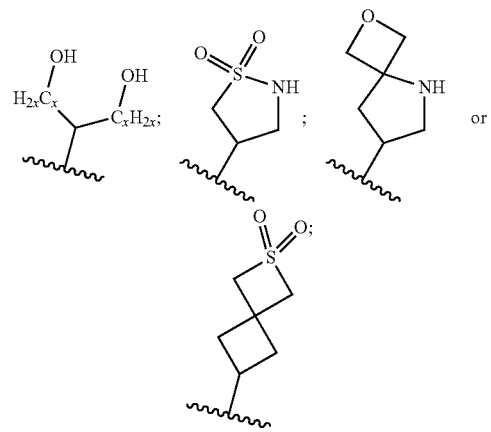

wherein x is 1-6;
$R^3$ is $C_{1-6}$alkyl;
$R^4$ is $C_{1-6}$alkyl;

or R³ and R⁴, with the carbon atom to which they are attached, form cycloalkyl;

W is nitrogen or —CR⁵, wherein R⁵ is hydrogen or halogen;

X is —CH or nitrogen;

or pharmaceutically acceptable salts thereof.

2. A compound according to claim 1, wherein

R¹ is chloro;

R² is azetidin-3-yl, methylsulfonylazetidin-3-yl, tert-butoxycarbonylpyrrolidinyl, isopropylcarbonylpyrrolidinyl, cyclopentyl, difluorocyclobutyl, difluorocyclopentyl, carboxycyclohexyl, hydroxycyclobutyl, hydroxycyclohexyl, hydroxycyclopentyl, methylsulfonylcyclobutyl, oxetan-3-yl, piperidin-4-yl, tetrahydrofuranyl, tetrahydropyranyl, R³ is methyl or ethyl;

R⁴ is methyl or ethyl;

or R³ and R⁴, with the carbon atom to which they are attached, form cyclopropyl;

W is nitrogen, —CH or —CF;

X is —CH or nitrogen;

or pharmaceutically acceptable salts thereof.

3. A compound according to claim 1 or a pharmaceutically acceptable salt thereof, wherein R¹ is halogen;

R² is azetidinyl, which is unsubstituted or substituted by $C_{1-6}$alkylsulfonyl; $C_{1-6}$alkoxycarbonylpyrrolidinyl; $C_{1-6}$alkylcarbonylpyrrolidinyl; cycloalkyl, which is unsubstituted or substituted by $C_{1-6}$alkyl, $C_{1-6}$alkylsulfonyl, carboxy, halogen or hydroxy; dioxo-tetrahydrothiophenyl, which is unsubstituted or substituted by $C_{1-6}$alkyl; dioxo-tetrahydrothiopyranyl; dioxo-thietanyl; oxo-thietanyl; oxo-pyrrolidinyl, which is unsubstituted or substituted by $C_{1-6}$alkyl; oxetanyl; oxopiperidinyl; piperidinyl; tetrahydrofuranyl; tetrahydropyranyl;

wherein x is 1-6;

R³ is $C_{1-6}$alkyl;

R⁴ is $C_{1-6}$alkyl;

or R³ and R⁴, with the carbon atom to which they are attached, form cycloalkyl;

W is —CR⁵, wherein R⁵ is hydrogen or halogen;

X is nitrogen.

4. A compound according to claim 1 or a pharmaceutically acceptable salt thereof, wherein R¹ is chloro;

R² is azetidin-3-yl, methylsulfonylazetidin-3-yl, tert-butoxycarbonylpyrrolidinyl, isopropylcarbonylpyrrolidinyl, cyclopentyl, difluorocyclobutyl, difluorocyclopentyl, carboxycyclohexyl, hydroxycyclobutyl, hydroxycyclohexyl, hydroxycyclopentyl, methylsulfonylcyclobutyl, oxetan-3-yl, piperidin-4-yl, tetrahydrofuranyl, tetrahydropyranyl,

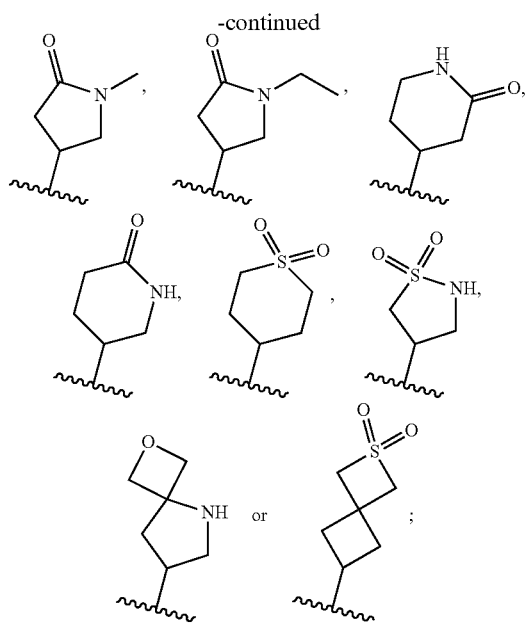

R³ is methyl or ethyl;
R⁴ is methyl or ethyl;
or R³ and R⁴, with the carbon atom to which they are attached, form cyclopropyl;
W is —CH or —CF;
X is nitrogen.

5. A compound according to claim 1 or a pharmaceutically acceptable salt thereof,
wherein
R¹ is halogen;
R² is dioxo-tetrahydrothiophenyl;
R³ and R⁴, with the carbon atom to which they are attached, form cycloalkyl;
W is nitrogen;
X is nitrogen.

6. A compound according to claim 1 or a pharmaceutically acceptable salt thereof,
wherein
R¹ is halogen;
R² is dioxo-tetrahydrothiophenyl;
R³ and R⁴, with the carbon atom to which they are attached, form cycloalkyl;
W is nitrogen or —CR⁵, wherein R⁵ is hydrogen or halogen;
X is —CH.

7. A compound according to claim 1, selected from
1'-({5-Chloro-1-[cis-3-(methylsulfonyl)cyclobutyl]-1H-benzimidazol-2-yl}methyl)spiro[cyclopropane-1,3'-pyrrolo[2,3-c]pyridin]-2'(1'H)-one;
1'-({5-Chloro-1-[trans-3-(methylsulfonyl)cyclobutyl]-1H-benzimidazol-2-yl}methyl)spiro[cyclopropane-1, 3'-pyrrolo[2,3-c]pyridin]-2'(1'H)-one;
1'-{[5-Chloro-1-(2,2-dioxido-2-thiaspiro[3.3]hept-6-yl)-1H-benzimidazol-2-yl]methyl}spiro[cyclopropane-1, 3'-pyrrolo[2,3-c]pyridin]-2'(1'H)-one;
1'-{[5-Chloro-1-(1,1-dioxidotetrahydro-2H-thiopyran-4-yl)-1H-benzimidazol-2-yl]methyl}spiro[cyclopropane-1,3'-pyrrolo[2,3-c]pyridin]-2'(1'H)-one;
1'-[(5-Chloro-1-cyclopentyl-1H-benzimidazol-2-yl)methyl]spiro[cyclopropane-1,3'-pyrrolo[2,3-c]pyridin]-2'(1'H)-one;
1'-{[5-Chloro-1-(oxetan-3-yl)-1H-benzimidazol-2-yl]methyl}spiro[cyclopropane-1,3'-pyrrolo[2,3-c]pyridin]-2'(1'H)-one;
1'-{[5-Chloro-1-(3,3-difluorocyclobutyl)-1H-benzimidazol-2-yl]methyl}spiro[cyclopropane-1,3'-pyrrolo[2,3-c]pyridin]-2'(1'H)-one;
1'-{[5-Chloro-1-(tetrahydro-2H-pyran-4-yl)-1H-benzimidazol-2-yl]methyl}spiro[cyclopropane-1,3'-pyrrolo[2,3-c]pyridin]-2'(1'H)-one;
1'-{[5-Chloro-1-(4-hydroxycyclohexyl)-1H-benzimidazol-2-yl]methyl}spiro[cyclopropane-1,3'-pyrrolo[2,3-c]pyridin]-2'(1'H)-one;
1'-{[5-Chloro-1-(3-hydroxycyclopentyl)-1H-benzimidazol-2-yl]methyl}spiro[cyclopropane-1,3'-pyrrolo[2,3-c]pyridin]-2'(1'H)-one;
1'-{[5-Chloro-1-(2-oxopyrrolidin-3-yl)-1H-benzimidazol-2-yl]methyl}spiro[cyclopropane-1,3'-pyrrolo[2,3-c]pyridin]-2'(1'H)-one;
1'-{[5-Chloro-1-(2-oxopiperidin-4-yl)-1H-benzimidazol-2-yl]methyl}spiro[cyclopropane-1,3'-pyrrolo[2,3-c]pyridin]-2'(1'H)-one;
1'-{[5-Chloro-1-(3 3-difluorocyclopentyl)-1H-benzimidazol-2-yl]methyl}spiro[cyclopropane-1,3'-pyrrolo[2, 3-c]pyridin]-2'(1'H)-one;
cis-4-{5-Chloro-2-[(2'-oxospiro[cyclopropane-1,3'-pyrrolo[2,3-c]pyridin]-1'(2'H)-yl)methyl]-1H-benzimidazol-1-yl}cyclohexanecarboxylic acid;
1'-{[6-Chloro-3-(1,1-dioxidotetrahydrothiophen-3-yl)-3H-imidazo[4,5-b ]pyridin-2-yl]methyl}spiro[cyclopropane-1,3'-pyrrolo[2,3-c]pyridin]-2'(1'H)-one;
1'-{[5-Chloro-1-(tetrahydrofuran-3-yl)-1H-benzimidazol-2-yl]methyl}spiro[cyclopropane-1,3'-pyrrolo[2,3-c]pyridin]-2'(1'H)-one;
tert-Butyl 3-{5-chloro-2-[(2'-oxospiro[cyclopropane-1,3'-pyrrolo[2,3-c]pyridin]-1'(2'H)-yl)methyl]-1H-benzimidazol-1-yl}pyrrolidine-1-carboxylate;
1'-{[5-Chloro-1-(1,3-dihydroxypropan-2-yl)-1H-benzimidazol-2-yl]methyl}spiro[cyclopropane-1,3'-pyrrolo[2,3-c]pyridin]-2'(1'H)-one;
1'-{[5-Chloro-1-(trans-3-hydroxy-3-methylcyclobutyl)-1H-benzimidazol-2-yl]methyl}spiro[cyclopropane-1, 3'-pyrrolo[2,3-c]pyridin]-2'(1'H)-one;
1'-{[5-Chloro-1-(1,1-dioxidotetrahydrothiophen-3-yl)-1H-benzimidazol-2-yl]methyl}spiro[cyclopropane-1, 3'-pyrrolo[2,3-c]pyridin]-2'(1'H)-one;
1'-({5-Chloro-1-[(3S)-1,1-dioxidotetrahydrothiophen-3-yl]-1H-benzimidazol-2-yl}methyl)spiro[cyclopropane-1,3'-pyrrolo[2,3-c]pyridin]-2'(1'H)-one;
1'-({5-Chloro-1-[(3R)-1,1-dioxidotetrahydrothiophen-3-yl]-1H-benzimidazol-2-yl}methyl)spiro[cyclopropane-1,3'-pyrrolo[2,3-c]pyridin]-2'(1'H)-one;
1'-{[5-Chloro-1-(1,1-dioxidothietan-3-yl)-1H-benzimidazol-2-yl]methyl}spiro[cyclopropane-1,3'-pyrrolo[2,3-c]pyridin]-2'(1'H)-one;
1-{[5-Chloro-1-(1,1-dioxidothietan-3-yl)-1H-benzimidazol-2-yl]methyl}-3,3-dimethyl-1,3-dihydro-2H-pyrrolo[2,3-c]pyridin-2-one;
1-{[5-Chloro-1-(1,1-dioxidothietan-3-yl)-1H-benzimidazol-2-yl]methyl}-3,3-diethyl-1,3-dihydro-2H-pyrrolo[2,3-c]pyridin-2-one;
1'-{[5-Chloro-1-(1-oxidothietan-3-yl)-1H-benzimidazol-2-yl]methyl}spiro[cyclopropane-1,3'-pyrrolo[2,3-c]pyridin]-2'(1'H)-one;
1'-{[5-Chloro-1-(1,1-dioxidothietan-3-yl)-7-fluoro-1H-benzimidazol-2-yl]methyl}spiro[cyclopropane-1,3'-pyrrolo[2,3-c]pyridin]-2'(1'H)-one;

1'-{[5-Chloro-1-(6-oxopiperidin-3-yl)-1H-benzimidazol-2-yl]methyl}spiro[cyclopropane-1,3'-pyrrolo[2,3-c]pyridin]-2'(1'H)-one;
1'-{[5-Chloro-1-(5-oxopyrrolidin-3-yl)-1H-benzimidazol-2-yl]methyl}spiro[cyclopropane-1,3'-pyrrolo[2,3-c]pyridin]-2'(1'H)-one;
1'-{[5-Chloro-1-(1-methyl-5-oxopyrrolidin-3-yl)-1H-benzimidazol-2-yl]methyl}spiro[cyclopropane-1,3'-pyrrolo[2,3-c]pyridin]-2'(1'H)-one;
1'-{[5-Chloro-1-(1-ethyl-5-oxopyrrolidin-3-yl)-1H-benzimidazol-2-yl]methyl}spiro[cyclopropane-1,3'-pyrrolo[2,3-c]pyridin]-2'(1'H)-one;
1'-({5-Chloro-1-[(3S)-1,1-dioxidotetrahydrothiophen-3-yl]-7-fluoro-1H-benzimidazol-2-yl}methyl)spiro[cyclopropane-1,3'-pyrrolo[2,3-c]pyridin]-2'(1'H)-one;
1'-({5-Chloro-1-[(3R)-1,1-dioxidotetrahydrothiophen-3-yl]-7-fluoro-1H-benzimidazol-2-yl}methyl)spiro[cyclopropane-1,3'-pyrrolo[2,3-c]pyridin]-2'(1'H)-one;
1'-{[5-Chloro-1-(piperidin-4-yl)-1H-benzimidazol-2-yl]methyl}spiro[cyclopropane-1,3'-pyrrolo[2,3-c]pyridin]-2'(1'H)-one;
1'-{[1-(Azetidin-3-yl)-5-chloro-1H-benzimidazol-2-yl]methyl}spiro[cyclopropane-1,3'-pyrrolo[2,3-c]pyridin]-2'(1'H)-one;
1'-({5-Chloro-1-[(3R)-1-(2-methylpropanoyl)pyrrolidin-3-yl]-1H-benzimidazol-2-yl}methyl)spiro[cyclopropane-1,3'-pyrrolo[2,3-c]pyridin]-2'(1'H)-one;
1'-({5-Chloro-1-[1-(methylsulfonyl)azetidin-3-yl]-1H-benzimidazol-2-yl}methyl)spiro[cyclopropane-1,3'-pyrrolo[2,3-c]pyridin]-2'(1'H)-one;
1'-{[5-Chloro-1-(2,2-dimethyl-1,1-dioxidotetrahydrothiophen-3-yl)-1H-benzimidazol-2-yl]methyl}spiro[cyclopropane-1,3'-pyrrolo[2,3-c]pyridin]-2'(1'H)-one;
1'-{[5-Chloro-1-(cis-3-hydroxycyclobutyl)-1H-benzimidazol-2-yl]methyl}spiro[cyclopropane-1,3'-pyrrolo[2,3-c]pyridin]-2'(1'H)-one;
1'-{[5-Chloro-1-(trans-3-hydroxycyclobutyl)-1H-benzimidazol-2-yl]methyl}spiro[cyclopropane-1,3'-pyrrolo[2,3-c]pyridin]-2'(1'H)-one;
1'-{[5-Chloro-1-(1,1-dioxido-1,2-thiazolidin-4-yl)-1H-benzimidazol-2-yl]methyl}spiro[cyclopropane-1,3'-pyrrolo[2,3-c]pyridin]-2'(1'H)-one;
1'-{[5-Chloro-1-(2-oxa-5-azaspiro[3.4]oct-7-yl)-1H-benzimidazol-2-yl]methyl}spiro[cyclopropane-1,3'-pyrrolo[2,3-c]pyridin]-2'(1'H)-one;
1'-{[5-Chloro-1-(1,1-dioxidotetrahydrothiophen-3-yl)-7-fluoro-1H-indol-2-yl]methyl}spiro[cyclopropane-1,3'-pyrrolo[2,3-c]pyridin]-2'(1'H)-one;
1'-{[5-Chloro-1-(1,1-dioxidotetrahydrothiophen-3-yl)-1H-indol-2-yl]methyl}spiro[cyclopropane-1,3'-pyrrolo[2,3-c]pyridin]-2'(1'H)-one; and
1'-{[5-Chloro-1-(1,1-dioxidotetrahydrothiophen-3-yl)-1H-pyrrolo[2,3-b]pyridin-2-yl]methyl}spiro[cyclopropane-1,3'-pyrrolo[2,3-c]pyridin]-2'(1'H)-one.

8. A process for the preparation of a compound of claim 1, the method comprising:
(a) contacting a compound of formula (A)

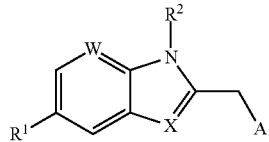

(A)

with

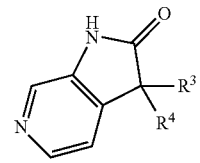

in the presence of a base;
wherein $R^1$ to $R^4$, W and X are defined as in claim 1 and A is methanesulfonate or chloro, to prepare a compound of claim 1;
or
(b) contacting a compound of formula (B)

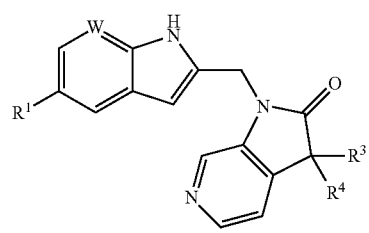

(B)

with Y—$R^2$ in the presence of a base;
wherein $R^1$ to $R^4$ and W are defined as in claim 1; and Y is trifluoromethanesulfonate or bromo, to prepare a compound of claim 1.

9. A pharmaceutical composition comprising a compound in accordance with claim 1 and a therapeutically inert carrier.

10. A method for the treatment or prophylaxis of respiratory syncytial virus infection, which method comprises administering an effective amount of a compound as defined in claim 1.

* * * * *